(12) United States Patent
Scaboo et al.

(10) Patent No.: US 12,169,184 B2
(45) Date of Patent: *Dec. 17, 2024

(54) WIRELESSLY SENSING PROPERTIES OF A CLOSED ENVIRONMENT AND DEVICES THEREOF

(71) Applicant: Gate Scientific, Inc., Milpitas, CA (US)

(72) Inventors: Kristian Michael Scaboo, Castro Valley, CA (US); Morten Juel Jensen, Saratoga, CA (US); George Pontis, Redwood City, CA (US); Paul Reynolds, Palo Alto, CA (US); Ethan Romander, San Jose, CA (US)

(73) Assignee: Gate Scientific, Inc., Milpitas, CA (US)

(*) Notice: Subject to any disclaimer, the term of this patent is extended or adjusted under 35 U.S.C. 154(b) by 988 days.

This patent is subject to a terminal disclaimer.

(21) Appl. No.: 17/089,431

(22) Filed: Nov. 4, 2020

(65) Prior Publication Data
US 2021/0096098 A1 Apr. 1, 2021

Related U.S. Application Data

(63) Continuation of application No. PCT/US2019/033615, filed on May 22, 2019.
(Continued)

(51) Int. Cl.
*G01N 27/416* (2006.01)
*C12M 1/34* (2006.01)
(Continued)

(52) U.S. Cl.
CPC ......... *G01N 27/4167* (2013.01); *C12M 41/12* (2013.01); *C12M 41/26* (2013.01);
(Continued)

(58) Field of Classification Search
CPC ... G01N 27/4167; C12M 41/12; C12M 41/26; C12M 41/48; G08C 17/02; G01K 13/026
See application file for complete search history.

(56) References Cited

U.S. PATENT DOCUMENTS

| | | | |
|---|---|---|---|
| 4,498,785 A | 2/1985 | De Bruyne | |
| 6,057,773 A | 5/2000 | Shukla et al. | |

(Continued)

FOREIGN PATENT DOCUMENTS

| | | |
|---|---|---|
| CN | 112533691 | 3/2021 |
| DE | 10 2012 008611 | 10/2013 |

(Continued)

OTHER PUBLICATIONS

Zangl, Hubert, et al. "Passive Wireless Devices Using Extremely Low to High Frequency Load Modulation." Mobile and Wireless Communications: Network Layer and Circuit Level Design. In-Teh, 2010. 93-107. (Year: 2010).*

*Primary Examiner* — Robert J Eom
(74) *Attorney, Agent, or Firm* — Levine Bagade Han LLP

(57) ABSTRACT

A wireless sensor that can measure properties of a substance and transmits the properties to a remote wireless receiver is disclosed. The wireless sensor can be fully enclosed within a container containing the substance, for example, allowing remote monitoring of the properties of the substance without compromising the integrity of the closed system.

18 Claims, 44 Drawing Sheets

Related U.S. Application Data

(60) Provisional application No. 62/810,371, filed on Feb. 25, 2019, provisional application No. 62/674,814, filed on May 22, 2018.

(51) Int. Cl.
  *C12M 1/36* (2006.01)
  *G01K 13/02* (2021.01)
  *G08C 17/02* (2006.01)

(52) U.S. Cl.
  CPC .............. *C12M 41/48* (2013.01); *G08C 17/02* (2013.01); *G01K 13/026* (2021.01)

(56) References Cited

U.S. PATENT DOCUMENTS

| | | |
|---|---|---|
| 6,616,821 B2 | 9/2003 | Broadley et al. |
| 2002/0154570 A1 | 10/2002 | Gebrian |
| 2004/0050836 A1 | 3/2004 | Nesbitt et al. |
| 2007/0298487 A1* | 12/2007 | Bachur .............. G06K 19/0723 600/315 |
| 2012/0091950 A1 | 4/2012 | Campanella et al. |
| 2014/0056325 A1 | 2/2014 | Guerra et al. |
| 2014/0263287 A1 | 9/2014 | Widitora et al. |
| 2014/0299471 A1 | 10/2014 | Mosley et al. |
| 2015/0117136 A1 | 4/2015 | Eble et al. |
| 2016/0151751 A1 | 6/2016 | Eble et al. |

FOREIGN PATENT DOCUMENTS

| | | |
|---|---|---|
| JP | 2011-20024 | 2/2011 |
| WO | WO 2011/117450 | 9/2011 |
| WO | WO 2019/226831 | 11/2019 |

* cited by examiner

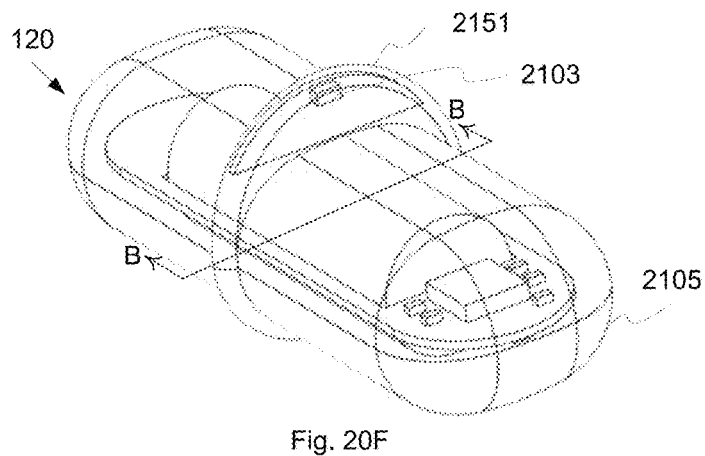
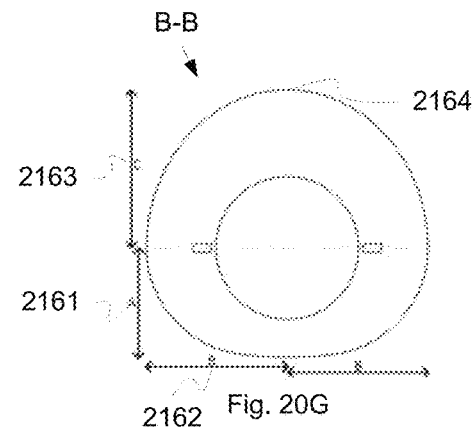
Fig. 20F
Fig. 20G
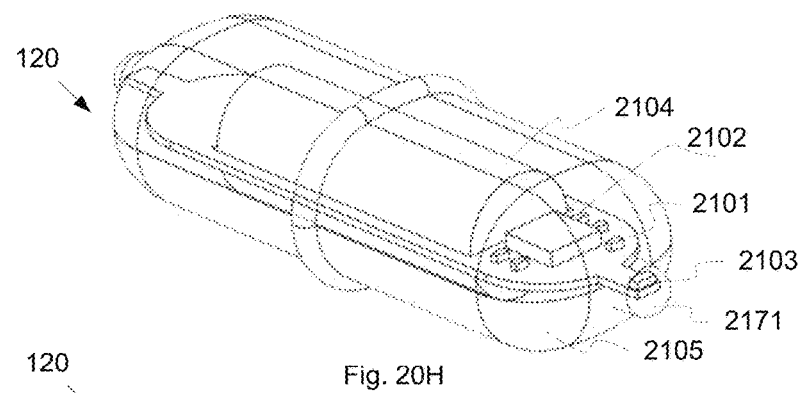
Fig. 20H
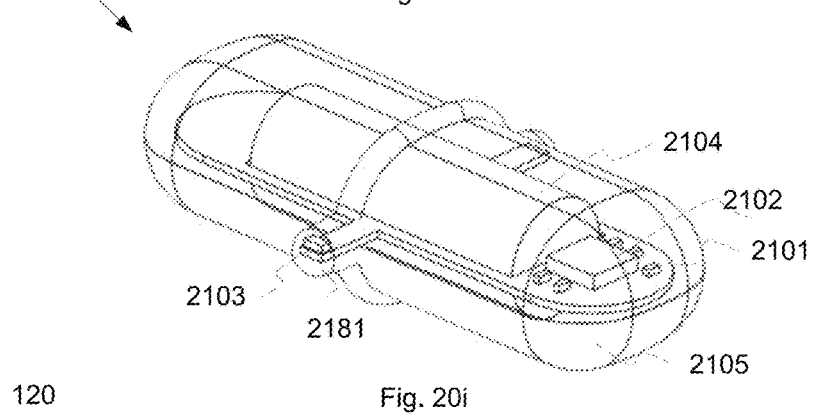
Fig. 20i
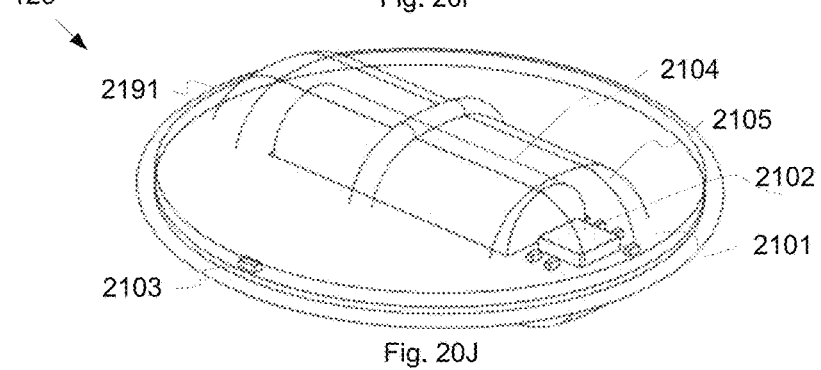
Fig. 20J

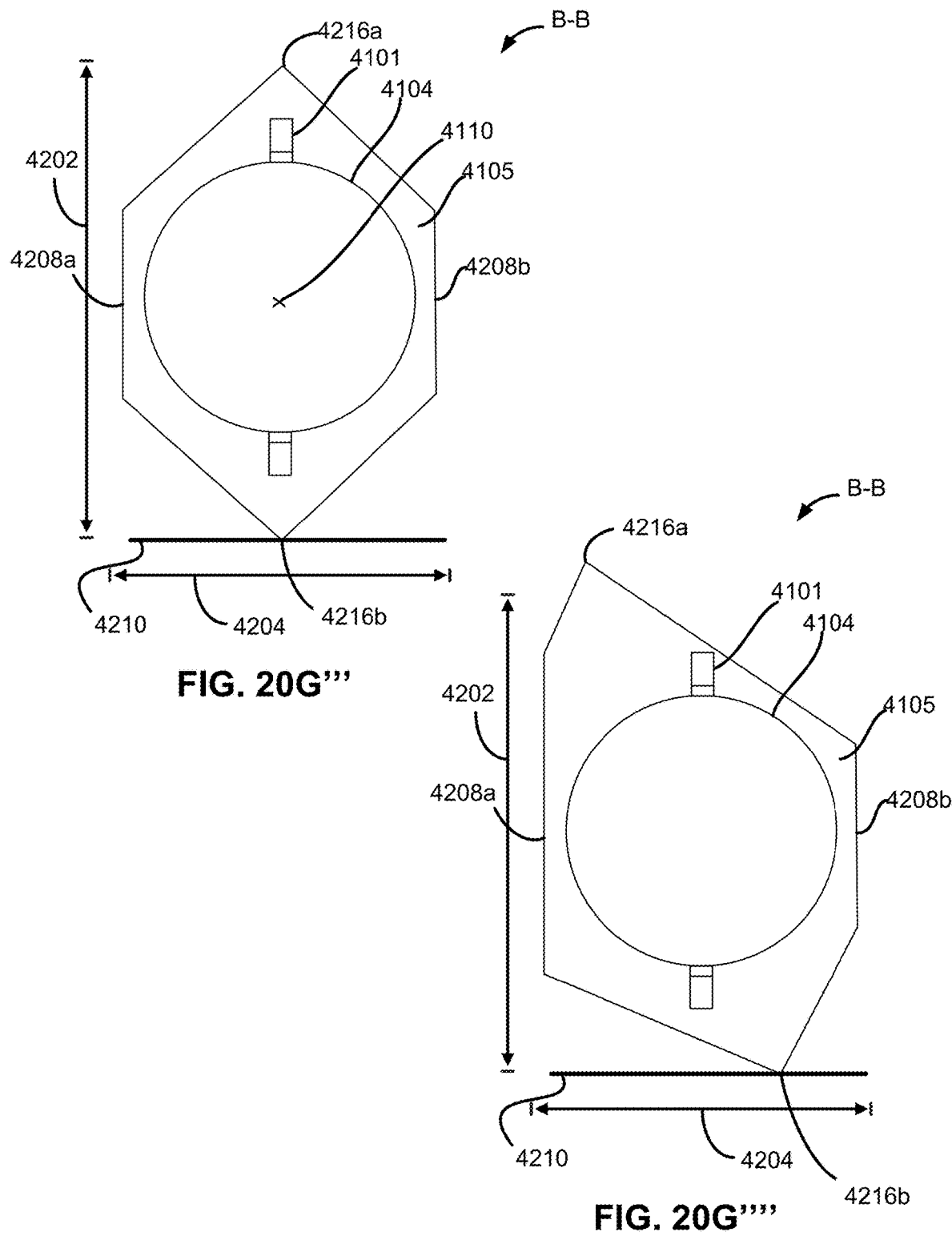

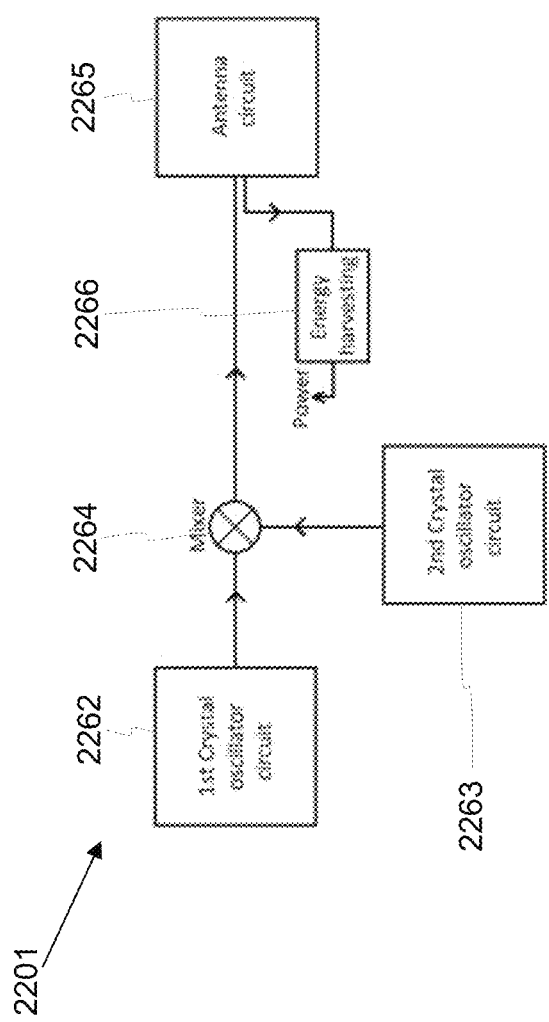
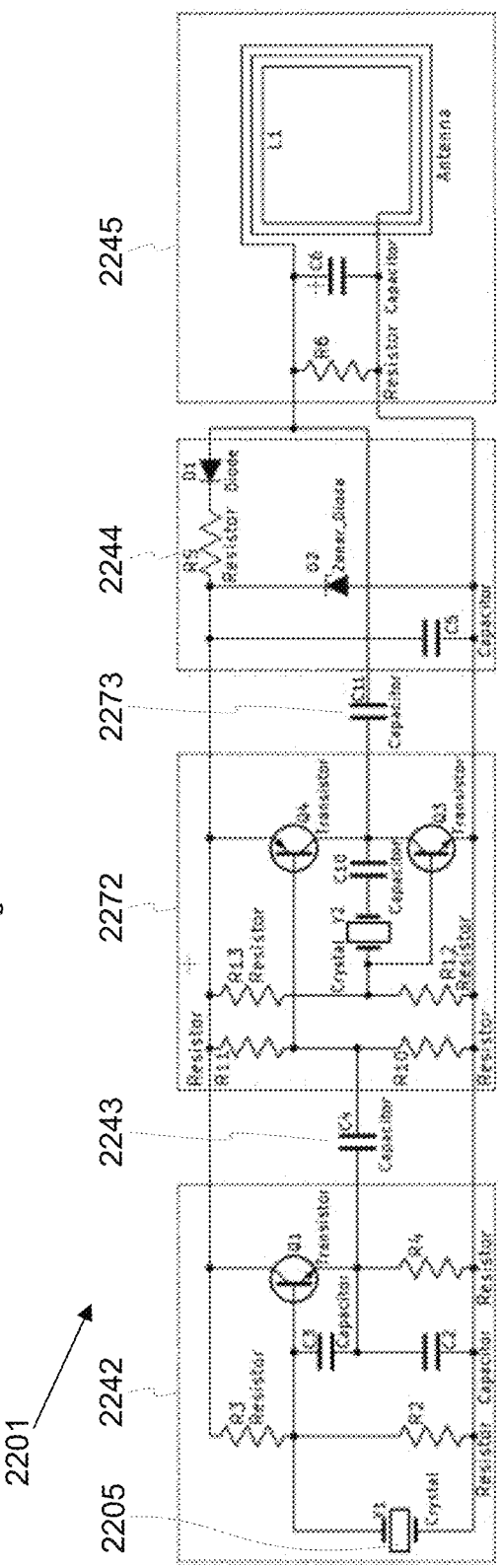
Fig. 21H
Fig. 21i

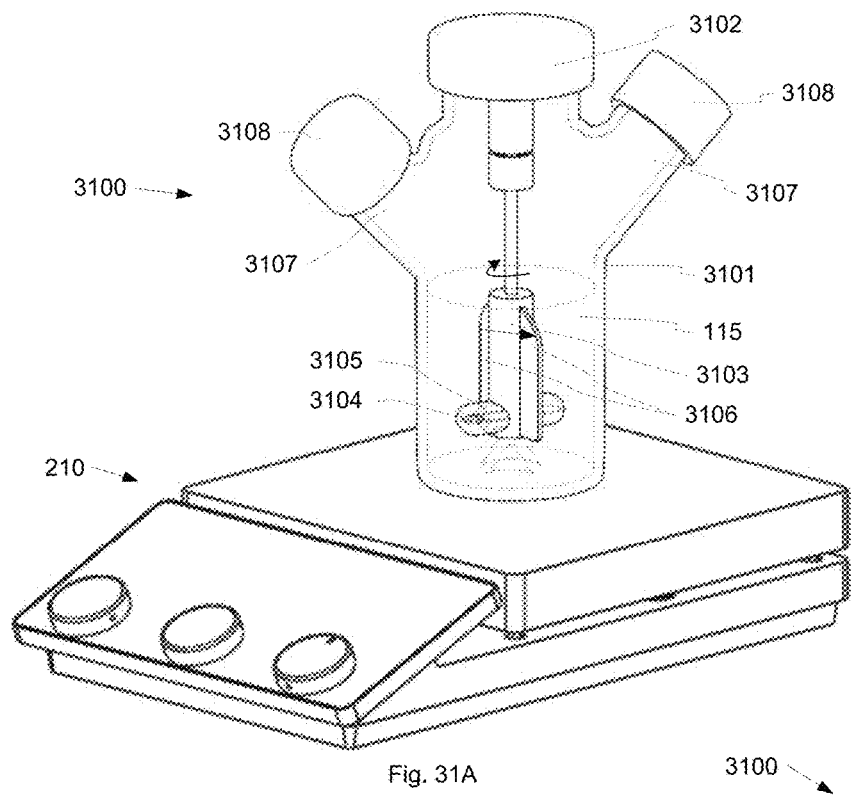
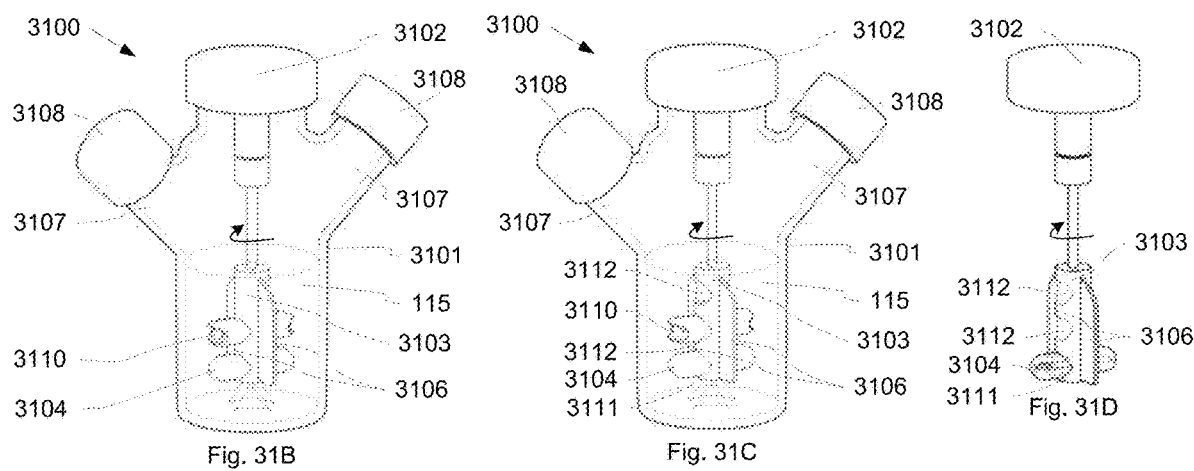
Fig. 31A
Fig. 31B
Fig. 31C
Fig. 31D

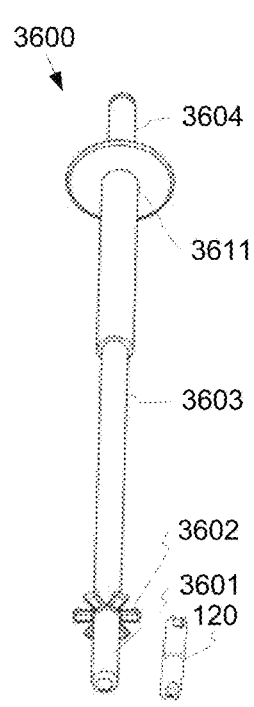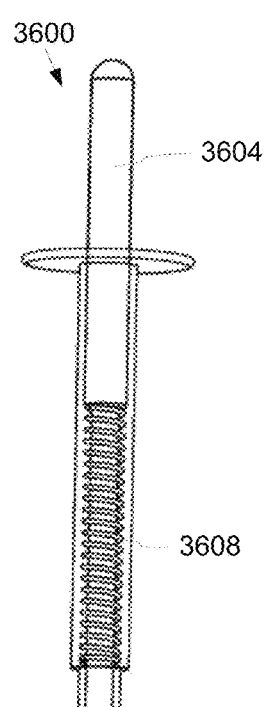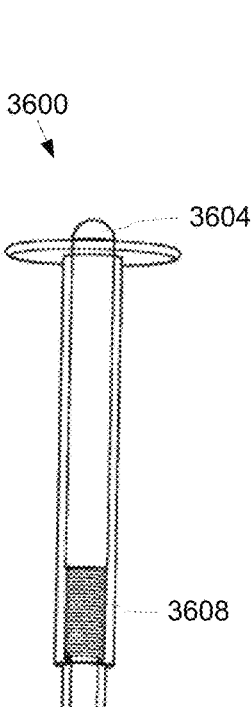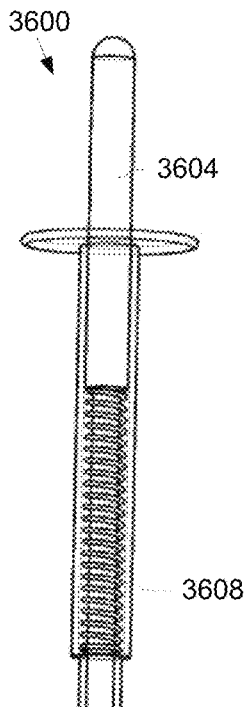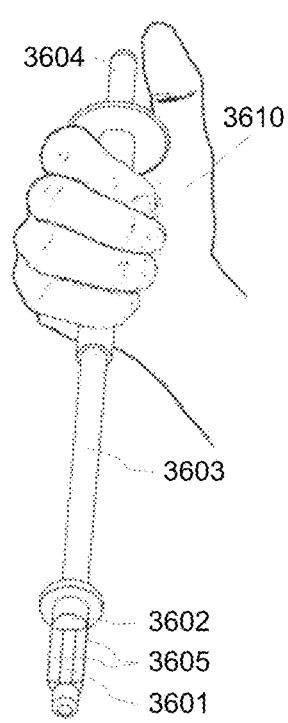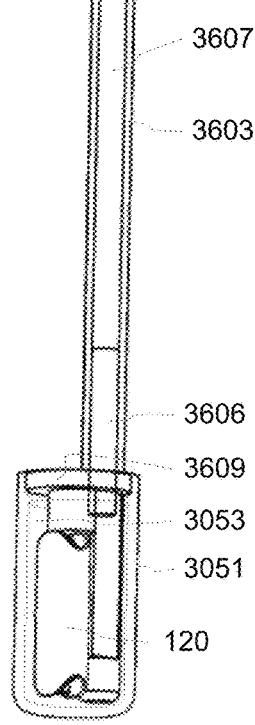
Fig. 36A
Fig. 36B
Fig. 36C
Fig. 36D
Fig. 36E

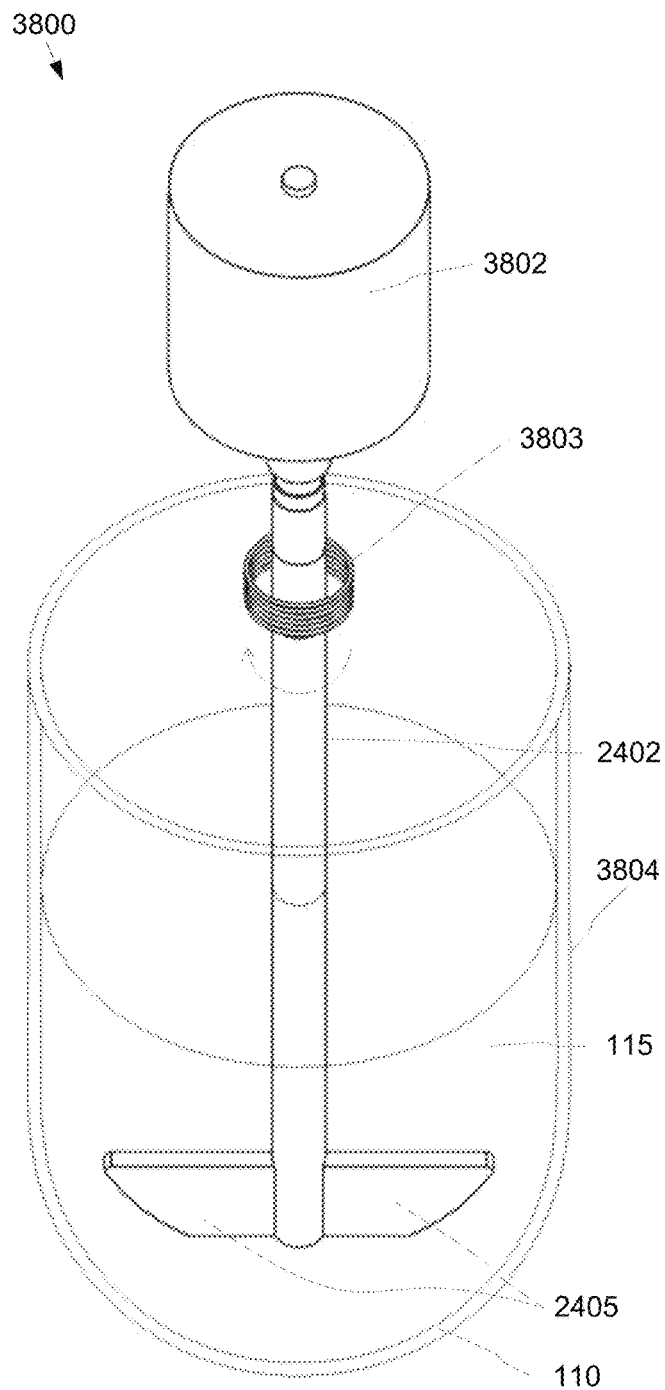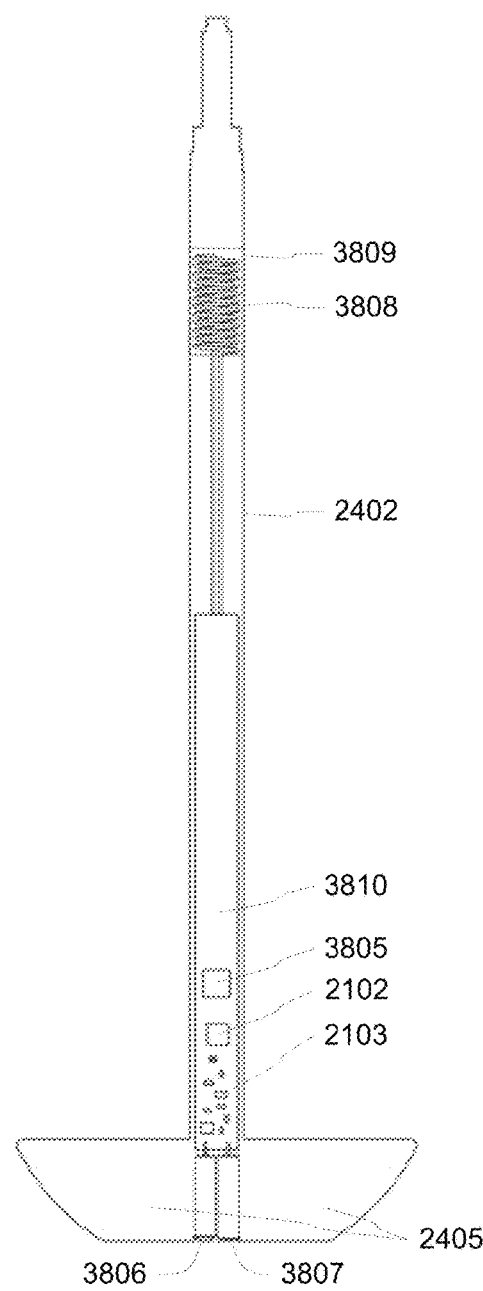
Fig. 38A
Fig. 38B

WIRELESSLY SENSING PROPERTIES OF A CLOSED ENVIRONMENT AND DEVICES THEREOF

CROSS-REFERENCE TO RELATED APPLICATIONS

This application is a continuation of International Application No. PCT/US2019/033615, filed May 22, 2019, which claims priority to U.S. Provisional Application No. 62/674,814, filed May 22, 2018, and U.S. Provisional Application No. 62/810,371, filed Feb. 25, 2019, all of which are incorporated by reference herein in their entireties.

BACKGROUND

(1) Technical Field

This disclosure relates to measuring and regulating properties of contents of a closed environment.

(2) Description of the Related Art

Numerous processes rely upon observation of contents of a closed environment in order to monitor and control the processes. For example, in a laboratory setting, a substance may be heated in a closed container to facilitate a desired chemical reaction or physical change. These closed containers may be heated using a hotplate stirrer, which can mix substances or keep them homogeneous while holding them at a certain temperature. Maintaining the temperature in these substances as they are mixed can be complicated by factors such as inconsistent transfer of heat from the hotplate to the substance as well as fluctuations in room temperature or hotplate power. Users of a hotplate may therefore use an external temperature probe to monitor the temperature of the substance. Some hotplates have temperature probes built into the plate that can measure the temperature of the heating plate surface. However, due to inconsistent thermal contact between the plate and the container, as well as inconsistent heat transfer to the substance inside the container, the built-in temperature probes typically have low accuracy. Other methods for measuring temperature include lowering a temperature probe into the sample, using a support structure external to the container, to directly measure the temperature of the substance. However, ensuring the probe remains in contact with the substance can be difficult, especially as the substance is mixed or agitated. Furthermore, if the container holding the substance needs to be closed during the heating and mixing process, lowering an external probe into the container can compromise the integrity of the process.

Other closed systems can similarly complicate measurement of properties of the system. There is therefore a need for a method to detect properties of a closed system, without compromising the integrity of the system.

SUMMARY

A wireless sensor that can measure properties of a substance and transmit the properties to a remote wireless receiver is disclosed. The wireless sensor can be fully enclosed within a container containing the substance, allowing remote monitoring of the properties of the substance without compromising integrity of a closed system.

The wireless sensor can be incorporated into a stir bar device, which can be magnetically manipulated by an instrument to agitate a fluid in a container. The instrument can heat the fluid in the container. As the stir bar device agitates the fluid, the device can measure properties of the fluid and transmit the properties to a control system of the instrument. The control system can regulate outputs of the instrument, such as an amount of heat or a rate of rotation of the stir bar device, based on feedback received from the wireless sensor in the stir bar device. Because the stir bar device wirelessly transmits data to the control system, the container can be sealed.

A wireless sensor can be used in systems to remotely monitor and control properties of substances.

An instrument is disclosed that can have an agitator, a temperature sensor and a controller. The agitator can be configured to agitate a liquid in a container. The temperature sensor can be immersible in the liquid. The temperature sensor can be configured to measure a temperature of the liquid. The temperature sensor can wirelessly transmit feedback indicating the temperature of the liquid to a wireless receiver. The controller can be configured to regulate the temperature of the liquid based on the feedback.

An instrument is disclosed that can have a wireless sensor and a wireless receiver. The wireless sensor can be enclosed within a closed container containing a substance. The wireless sensor can have a wireless transmitter. The wireless sensor can have a sensor configured to measure a property of the substance. The wireless receiver can be in electronic communication with the wireless transmitter. The wireless transmitter can transmit data describing the property of the substance to the wireless receiver.

A wireless temperature measurement device is disclosed. The wireless temperature measurement device can be configured to work as an agitator that can be dropped into liquid. The liquid can be heated or cooled by an instrument. The instrument can communicate with and power the measurement device wirelessly. The device can measure the temperature of the liquid.

The wireless temperature measurement device can have a wireless temperature sensor device configured to communicate with a receiver via wireless communication. The sensor device can have at least one of the following properties: a) the sensor device is powered with wireless energy; b) the sensor device agitates liquid by use of magnetic action; c) the sensor device has at least 2 different temperature measurement elements that can be compared and if they do not track then the device is considered broken or out of calibration; d) at least one of the temperature measurement elements is configured to operate by measuring the resistance change in a thermistor; and/or e) at least one of the temperature measurement elements is configured to operate by measuring the change in voltage of a semiconductor device.

The device can be completely immersed into the liquid. The measurement device may not require any wires to function. The wireless temperature measurement device can have at least one of the following properties: a) the measurement device communicates with the instrument via wireless signals and the measurement device is powered with wireless energy; b) the liquid to be heated is contained in a separate container that can be placed on or at the instrument; c) the measurement device can function as an agitator of the liquid to be heated and the instrument activates the agitator function via a magnetic field; and/or d) the measurement device can measure at least one other liquid characteristic, said at least one other characteristic being any of pH, sodium, ammonia, lithium, potassium, calcium, dissolved oxygen, $CO_2$, Specific gravity, refractive index, viscosity, salinity, conductance, color, absorbance, fluorescence, pressure, electrochemical, conductivity, chemiluminescence, liquid level, rotation, acceleration or velocity.

The measurement device can be completely immersed into the liquid. The measurement device can measure the temperature of the liquid. The wireless measurement device can have at least one of the following properties: a) the measurement device communicates with the instrument via radio waves and the measurement device is powered with radio waves; b) the liquid to be agitated is contained in a separate container that can be placed on or at the instrument; c) the measurement device can function as an agitator of the liquid to be heated and where the instrument can activate the agitator function via a magnetic field; d) the measurement device can measure other liquid characteristics such as any of pH or fluid velocity; e) the measurement device can measure at least one other characteristic of the fluid, said at least one other characteristic being any of pH, sodium, ammonia, lithium, potassium, calcium, dissolved oxygen, $CO_2$, specific gravity, refractive index, viscosity, salinity, conductance, color, absorbance, fluorescence, pressure, electrochemical, conductivity, chemiluminescence, liquid level, rotation or velocity.

A system is disclosed where a fluid disposed inside of a sealed container is automatically measured remotely for at least one measurement without direct electrical connection. The system can have at least one of: a) the at least one measurement is done using wireless communication and wireless powering of the sensor, at least one measurement being any of temperature, electrochemical, pH, sodium, ammonia, lithium, potassium, calcium, dissolved oxygen, $CO_2$, specific gravity, refractive index, viscosity, conductance, salinity, color, absorbance, fluorescence, pressure, conductivity, chemiluminescence, liquid level, rotation, velocity and acceleration; and/or b) the at least one measurement is done using wireless or optical communication to a wirelessly or optically powered sensor, said at least one measurement being any of temperature, electrochemical, pH, sodium, ammonia, lithium, potassium, calcium, dissolved oxygen, $CO_2$, specific gravity, refractive index, viscosity, conductance, salinity, color, absorbance, fluorescence, pressure, conductivity, chemiluminescence, liquid level, rotation, velocity and acceleration.

A system for manipulating a liquid compound based on the feedback from a wireless sensor element that can measure one or more parameters in the liquid is disclosed. The liquid manipulation can be by heating, cooling, agitation, mechanical homogenization, electrolysis, adding another compound exposing to electromagnetic waves comprising any of light or radio waves or x-rays, exposing to radiation, exposing to pressure or vacuum exposing to sound waves or ultrasound waves, exposing to centrifugal force, exposing to an electric field, exposing to a magnetic field, removing selective constituents by filtering or density separation of certain compounds, removing bulk liquid, degassing, desalination; and wherein said feedback is obtained from at least one wireless measurement, said at least one wireless measurement being any of temperature, electrochemical, pH, sodium, ammonia, lithium, potassium, calcium, dissolved oxygen, $CO_2$, specific gravity, refractive index, viscosity, conductance, salinity, color, absorbance, fluorescence, pressure, conductivity, chemiluminescence, liquid level, rotation, velocity, acceleration, or combinations thereof.

A system is disclosed that can have a container that can have an embedded wireless temperature sensor and a separate communication device that can communicate with the wireless temperature sensor. The system can have any of: a) the embedded wireless temperature sensor can be powered with wireless power; b) the communication device is configured to heat the container; c) the communication device can be set to heat the container based on the temperature feedback transmitted wirelessly; d) the container has built in mechanical blades for homogenization or heating the material in the container and where the communication device has an activation element configured to activate the mechanical blades; e) the communication device can be set to activate the blades in the container based on the temperature feedback transmitted wirelessly.

A system is disclosed where a substance disposed inside of a sealed container can be automatically measured remotely with a wireless sensor for at least one measurement without direct electrical connection. The system can have at least one of: a) the at least one measurement is done using wireless communication and wireless powering of the sensor, at least one measurement being any of temperature, electrochemical, pH, sodium, ammonia, lithium, potassium, calcium, dissolved oxygen, $CO_2$, specific gravity, refractive index, viscosity, conductance, salinity, color, absorbance, fluorescence, pressure, conductivity, chemiluminescence, fill level, rotation, velocity and acceleration; b) the at least one measurement is done using wireless or optical communication to a wirelessly or optically powered sensor, said at least one measurement being any of temperature, electrochemical, pH, specific gravity, refractive index, viscosity, conductance, salinity, color, absorbance, fluorescence, pressure, conductivity, chemiluminescence, fill level, rotation, velocity and acceleration; c) the at least one measurement is done using wireless or optical communication to a sensor, said at least one measurement being temperature and specific gravity of the fluid; or combinations thereof. The disclosed system can have: a wireless sensor that contains a wireless transmitter for transmitting sensor data to a wireless receiver and where the wireless receiver is a computing device such as a smart phone; and where the wireless sensor can measure temperature and specific gravity of the substance in the container. The system can have any of the following: A) the wireless receiver computing device that receives the wireless sensor data can emit a notification if the temperature of the substance is outside specified limits; B) the wireless receiver computing device that receives the wireless sensor data can emit a notification if the specific gravity of the substance is outside specified limits; C) the wireless receiver computing device has pre-select profiles that sets parameters for durations and specified temperature limits for the substance and where the wireless receiver computing device emits a notification if the substance parameters are outside the profile parameters; D) the wireless receiver computing device has pre-select profiles that sets parameters for durations and specified temperature limits and specified specific gravity limits for the substance and where the wireless receiver computing device emits a notification if the substance parameters are outside the profile parameters; E) the wireless sensor data is presented to the wireless receiver computing device in the form of a web page using standard web language such as HTML; F) the wireless receiver computing device processes an application program that interpret and presents the wireless sensor data; G) the wireless sensor transmits sensor data through one or more wireless routers to the wireless receiver computing device; H) the wireless sensor is made to float on or at the top of the substance in the container; or combinations thereof.

An instrument device is disclosed for cooling or heating and agitating a liquid in a separate container and a wireless measurement device that can be dropped into the liquid to be cooled or heated and where the instrument communicates with and powers the measurement device wirelessly and can thereby measure at least one property of the liquid, wherein the liquid is agitated by magnetic action by a separate encapsulated magnet that is dropped into the liquid, and wherein the measurement device can float near or at the top of the liquid, and wherein the measurement device measures at least one property of the liquid, said at least one property of the liquid being any of pH, sodium, ammonia, lithium, potassium, calcium, dissolved oxygen, $CO_2$, specific gravity, refractive index, viscosity, salinity, conductance, color, absorbance, fluorescence, pressure, electrochemical, conductivity, chemiluminescence, liquid level, rotation or velocity.

A wireless sensor that can measure properties of a substance and transmit the properties to a remote wireless receiver is disclosed. The wireless sensor can be fully enclosed within a container containing a substance, allowing remote monitoring of the properties of the substance without compromising integrity of a closed system. The wireless sensor communicates and is powered by RFID wireless communication at a frequency that is in a range that does not significantly gets absorbed by the substance. Such a frequency is 13.56 MHz which is a standard RFID transmission frequency that does not significantly gets absorbed by aqueous liquid substances and which can have a significantly high bandwidth to be able to send both sensor data, calibration data, identification data and security info data many times per second. The RFID protocol can be ISO/IEC 15693 or ISO/IEC 14443 or FeliCa. The advantage of using a RFID protocol is that it contains features for data communication and for uniquely identification of a device as well as communication error handling and other relevant features. Since the RFID communication protocols have been developed it makes for a quicker development cycle by using standard protocols rather than developing a proprietary protocol. There are integrated communication circuits available that operates at this frequency and therefore allows the wireless sensor a high level of integration and reduced size. Example of such an integrated circuit is Texas Instrument RF430FRL152H which is a RFID communication circuit that operates at 13.56 MHz.

A wireless sensor that can measure properties of a substance and transmit the properties to a remote wireless receiver is disclosed. The wireless sensor can be fully enclosed within a container containing a substance, allowing remote monitoring of the properties of the substance without compromising integrity of a closed system. The wireless sensor is powered wireless energy and communicates at a frequency that is in a range that does not significantly gets absorbed by the substance. Below 100 MHz radio waves do not significantly gets absorbed in aqueous liquid substances. There are several frequencies that are regularly used in RFID systems such as 125 kHz, 134 kHz and 13.56 MHz. The communication and/or powering of the wireless sensor can happen without using an established RFID protocol.

A unique identification code in the wireless sensing device can be used to uniquely identifying a specific wireless sensing device. This can be useful in the case where usage data or calibration data or expiration time need to be tracked by a reader device or where the location of a wireless sensing device can provide information about the wireless sensing device or the substance or container in which the wireless sensing device is located.

A type identification code in the wireless sensing device can be used by the reading device to identify the type of wireless sensing device that a reader device is communicating with and can configure the reading device to present specific data to a user in a specific manner depending on the type of wireless sensing device. For example if the wireless sensing device is identified to be a temperature sensing device by the type identification information in the wireless sensing device then the reader device can acquire and display temperature readings to a user whereas if the wireless sensing device is identified to be a combined pH and temperature sensing device by the type identification information in the wireless sensing device then the reader device can acquire and display pH readings and temperature readings to a user.

The reading device can communicate with an external computing device over WiFi or Ethernet or USB and thereby transmit data from the wireless sensing device to an external computing device as well as allow an external computing device to control temperature and rotation of the reading device.

A wireless sensing device that can measure a property of a substance and where the sensing surface of the sensing device such as a glass membrane for sensing pH is protected from damage by having mechanical features that prevent the sensing surface from coming in direct contact with a surface or where the sensing surface is recessed into the body of the sensing device.

A wireless sensing device that can measure pH in a closed container and transmit the measurement wirelessly. The pH measurement can be done using a H+ selective glass surface. The sensing device can be powered by a battery or by wireless power such as from 13.56 MHz RFID wireless signal. Where the wireless sensing device can have a magnetically effected member such that the sensing device can be rotated or moved by an external magnetic field and whereby the measurement of pH can stabilize fast due to the movement of the pH sensing surface relative to substance to be measured. The wireless sensing device can function as a stirrer of a substance. The wireless sensing device can measure temperature whereby the pH measurement can be compensated by the effect of temperature.

A wireless sensing device that can measure a parameter of a substance in a closed container and transmit the measurement wirelessly. The measurement can be done using clark type sensor element. The sensing device can be powered by a battery or by wireless power such as from 13.56 MHz RFID wireless signal. Where the wireless sensing device can have a magnetically effected member such that the sensing device can be rotated or moved by an external magnetic field and whereby the measurement of a substance can stabilize fast due to the movement of the sensing element relative to substance to be measured. For example, for measuring dissolved oxygen the moving of the sensor in the liquid can provide a better measurement. The wireless sensing device can function as a stirrer of a substance. The wireless sensing device can measure temperature whereby the measurement can be compensated by the effect of temperature.

A wireless sensing device that can measure a property of a substance in a container and transmit the result wirelessly to a receiver, where the receiver can be a scale that can measure the weight of the container and substance A container for growing cells where the container has built in sensors for measuring parameters of the cells or of the substance in which the cells grows and transmit the measurements wirelessly to a receiver or where the container has attached a display for showing the measurement results.

A hollow rod magnet or tube-shaped magnet that makes up the magnetically activated member of a device such that electrical circuit and or electrical components can be located fully or partially inside the outline of the magnet. The magnet can be made of neodymium or other magnetic components. The hollow magnet can be the magnetically activated component of a wireless sensing device that can be moved by applying an external magnetic field. This construction of the magnetic member can make the construction of wireless sensing devices more compact which may be needed for certain applications.

A method is described for determining pH of a first liquid in a container and agitating the same first liquid. The method can include positioning the container on a receiver instrument. The receiver instrument can include a wireless receiver. The method can include positioning a submersible device in the first liquid. The submersible device can include a pH sensor, a reference sensor, a temperature sensor, and a wireless transmitter. The wireless transmitter can be in communication with the wireless receiver. The method can include measuring pH of the first liquid by determining the voltage potential difference between the pH sensor and the reference sensor; measuring a temperature of the first liquid with the first temperature measurement element; communicating data to the receiver instrument; and agitating the first liquid. The submersible device can include a first magnet. The receiving instrument can include a magnetic field creator. The magnetic field creator can create and alter a magnetic field exerting a magnetic force on the first magnet. The agitating of the first liquid can include moving the submersible device in the first liquid with the magnetic force on the first magnet.

A magnetic field creator can include a permanent magnet and a motor. The motor can be mechanically attached to the permanent magnet. The method can include rotating the permanent magnet with the motor.

A magnetic field creator can comprise one or more electromagnets.

A method is described of achieving a certain pH of a first liquid by dispensing an amount of a second liquid into the first liquid comprising setting a target pH of the first liquid with one or more controls on the receiving instrument; where the receiving instrument controls the introduction of a second liquid into the first liquid until a specified pH level of the first liquid is reached by means of a pump; displaying to the user the amount of second liquid pumped into the first liquid.

A submersible device that is powered by wireless energy and where the submersible device does not contain a battery.

A submersible device communicates with a receiving instrument using RFID communication and where the RFID communication powers the submersible device.

A submersible device communicates with a receiving instrument using 13.56 MHz frequency.

A method where pH is calculated based on the voltage potential difference between the pH sensor and the reference sensor and where the pH calculation is compensated based on the first liquid temperature from the first temperature measurement element, where the calculation of the pH is performed in the receiving instrument.

A method where the pH is calculated based on the voltage potential difference between the pH sensor and the reference sensor and where the pH calculation is compensated based on the first liquid temperature from the first temperature measurement element, where the calculation of the pH is performed in the submersible device.

A method where a submersible device comprises a pH sensor and a reference sensor and a temperature sensor and a magnet and a circuit board and where the circuit board comprises an antenna embedded in the circuit board and where the circuit board has at least one integrated circuit for measuring the voltage potential difference between the pH sensor and the reference sensor and where the same or an additional integrated circuit can measure a temperature measurement element and where the same or an additional integrated circuit has a wireless transmitter.

The submersible device can include a hollow magnet.

The submersible device can contain a pH sensor that can include a glass electrode that is sensitive to hydrogen ions.

A submersible device where the reference sensor comprises one of the following:
  a porous frit with a potassium chloride gel electrolyte and a gel electrolyte containing silver and silver chloride in contact with a silver electrode;
  a porous frit with a potassium chloride and silver and silver chloride electrolyte in contact with the porous frit and silver electrode;
  a potassium chloride hard gel electrolyte in contact with a silver and silver chloride electrolyte which is in contact with a silver electrode;
  a porous frit in contact with an electrolyte which is in contact with an electrode;
  a porous frit in contact with a first electrolyte which is in contact with a second electrolyte which is in contact with an electrode;
  a PTFE membrane in contact with an electrolyte which is in contact with an electrode;
  a PTFE membrane in contact with a first electrolyte which is in contact with a second electrolyte which is in contact with an electrode.

The method can include a submersible device that can be completely immersed into a first liquid. The submersible device can require no wires to function. The submersible device can measures at least one liquid characteristic, said at least one characteristic being any of temperature, pH, sodium, ammonia, lithium, potassium, calcium, dissolved oxygen, $CO_2$, specific gravity, refractive index, viscosity, salinity, conductance, color, absorbance, fluorescence, pressure, electrochemical, conductivity, chemiluminescence, liquid level, rotation, acceleration, velocity or combinations thereof.

A receiver instrument can also heat the first liquid.

A method for determining pH of a first liquid in a container is disclosed. The method can include positioning the container at a receiver instrument, wherein the receiver instrument comprises a wireless receiver; positioning a submersible device in the first liquid, wherein the submersible device comprises a pH sensor and a reference sensor and a temperature sensor and a wireless transmitter, and wherein the wireless transmitter is in communication with the wireless receiver; measuring pH of the first liquid by determining the voltage potential difference between the pH sensor and the reference sensor, where the pH sensor comprises a glass electrode that is sensitive to hydrogen ions and where the reference sensor comprises a porous frit with gel electrolyte in and an electrode; measuring a temperature of the first liquid with the first temperature measurement element; communicating data to the receiver instrument; powering the submersible device with wireless energy such that the submersible device does not contain a battery; calculating the pH based on the voltage potential difference between the pH sensor and the reference sensor and compensating the pH calculation based on the first liquid temperature from the first temperature measurement element.

A method can include that a first liquid is agitated by a submersible device and wherein the submersible device comprises a first magnet, and wherein a receiving instrument comprises a magnetic field creator, and wherein the magnetic field creator creates and alters a magnetic field exerting a magnetic force on the first magnet, and wherein the agitating the first liquid comprises moving the submersible device in the first liquid with the magnetic force on the first magnet.

The method can include a submersible device communicating with a receiving instrument using RFID communication at 13.56 MHz frequency and where the RFID communication powers the submersible device.

A method for determining a parameter of a first liquid in a container and agitating the same first liquid is disclosed. The method can include positioning the container on a receiver instrument, wherein the receiver instrument comprises a wireless receiver; positioning a submersible device in the first liquid, wherein the submersible device comprises a sensor and a wireless transmitter, and wherein the wireless transmitter is in communication with the wireless receiver; measuring a parameter of the first liquid with the sensor where the parameter can be any of temperature, pH, sodium, ammonia, lithium, potassium, calcium, dissolved oxygen, $CO_2$, Specific gravity, refractive index, viscosity, salinity, conductance, color, absorbance, fluorescence, pressure, electrochemical, conductivity, chemiluminescence, liquid level, rotation, acceleration or velocity; communicating data to the receiver instrument; agitating the first liquid, wherein the submersible device comprises a first magnet, and wherein the receiving instrument comprises a magnetic field creator, and wherein the magnetic field creator creates and alters a magnetic field exerting a magnetic force on the first magnet, and wherein the agitating the first liquid comprises moving the submersible device in the first liquid with the magnetic force on the first magnet.

The submersible device can communicate with a receiving instrument using RFID communication at 13.56 MHz frequency and where the RFID communication powers the submersible device.

BRIEF DESCRIPTION OF THE DRAWINGS

FIGS. 20C through 20F are partial see-through perspective views of variations of the sensing device.

FIGS. 20H through 20N are partial see-through perspective views of variations of the sensing device.

FIGS. 21F through 21i illustrate variations of sensor circuits for the sensing device.

FIG. 31A through 31D illustrates an example container for wireless sensing of properties of substances.

FIG. 36A through 36H illustrates variation of systems for transferring a wireless sensing device from one environment to another environment.

FIG. 38A illustrates a wireless sensing system implemented as part of a mixing system.

FIG. 38B is a variation of a cross-sectional view of the stirrer of FIG. 38A.

DETAILED DESCRIPTION

Figure 1:
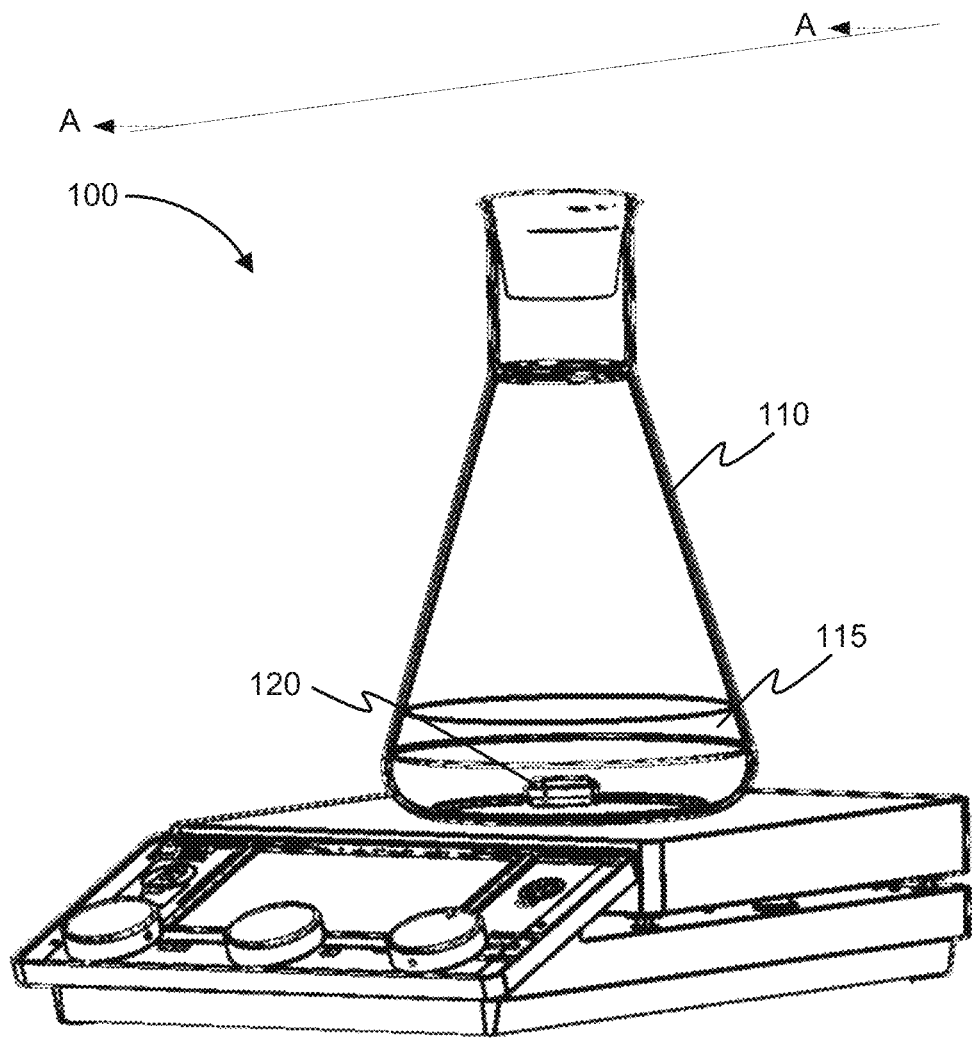
FIG. 1 is a perspective view a system for measuring and regulating properties of contents of a closed container.

FIG. 1 illustrates that a system 100 for measuring and regulating properties of contents of a closed container can have a container 110 containing a substance 115 and a sensing device 120. The container 110 can be a closed or partially closed environment. For example, the container 110 can be a flask, vial, or pot that can contain the substance 115 and can be closed via a stopper or lid to form an airtight environment. The container 110 may be closable with a stopper or lid to form an environment that is not airtight or may be open to the ambient environment. Other examples of the container 110 include a blender pitcher, a fermenting vessel, a bottle, a well plate, or any other container suitable to contain the substance 115.

The substance 115 can include any liquid, solid, gel, gas, or combination of materials. Properties of the substance 115 can be changed and controlled by the system 100 based on data detected by the sensing device 120. Data describing properties of the substance 115 can be wirelessly transmitted by the sensing device 120 to a wireless receiver outside the container 110.

The sensing device 120 can be fully enclosed in the container 110, and some configurations of the sensing device 120 can be fully or partially immersible in the substance 115. The sensing device 120 can be supported by and fully contained within the container 110 or may cross through the container 110 without compromising the integrity of a closed environment in the container 110. The sensing device 120 may be wirelessly powered by an external wireless receiver, enabling the sensing device 120 to function without a battery. Because a battery requires periodic charging, can wear out after a number of charges, and typically operates most effectively within a limited temperature range, omitting a battery from the sensing device 120 can improve the longevity of the device and can be used for applications that may expose the device 120 to extreme temperatures. The sensing device 120 can include a battery.

Figure 2:
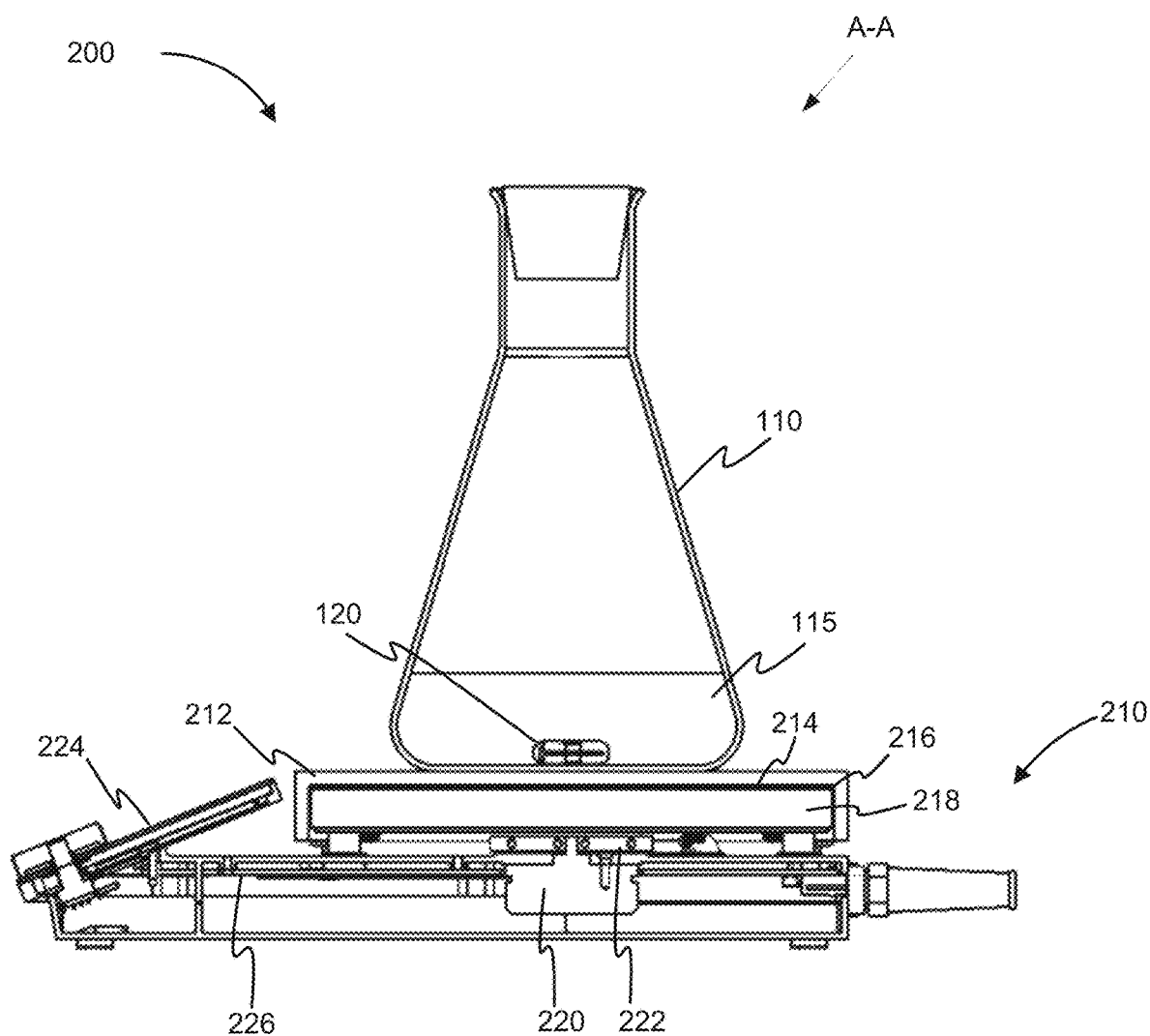
FIG. 2 is a variation of cross-section A-A of FIG. 1.

FIG. 2 shows an example configuration 200 of the system 100, along cross-section A-A shown in FIG. 1. The system 200 can be a system for heating and agitating a substance 115 in a container 110, and can include an instrument 210, such as a hot plate, and the sensing device 120.

The instrument 210 can include a heating surface 212 for supporting the container 110 and transferring heat from a heating element 216 to the container 110 and substance 115. A wireless receiver 214 can be positioned under the heating surface 212 and electrically and thermally insulated from the heating element 216 or the heating element 216 can be combined with the wireless receiver 214. Under the heating element 216 can be an insulating layer 218. The instrument 210 can include a magnet 222 rotatable by a motor 220.

The magnet 222 can cause a magnetic object placed on or near the heated surface 212 to rotate as the magnet 222 is rotated by the motor 220. Accordingly, a magnetic object placed in the container 110 can agitate or mix the substance 115 as it is rotated by the magnet 222. The sensing device 120 can include a corresponding magnet, enabling the sensing device 120 to function as an agitator of the substance 115, or a magnet separate from or coupled to the sensing device 120 may be placed into the container 110. The magnetic action can be accomplished by electromagnets placed under or near the heating surface 212.

The instrument 210 can include a control panel 224 configured to receive user inputs and display information to the user. For example, the control panel 224 can receive user inputs to increase or decrease a temperature of the heating element 216 and increase or decrease a rate of rotation of the magnet 222. The control panel 224 can include a display, such as an LCD screen or electronic ink (E Ink) screen or one or more LEDs, that can display temperature, magnet rotation, or other information to the user. The control panel 224 can additionally or alternatively include buttons, knobs, or other input devices enabling a user to provide input into the instrument 210.

A controller 226 in the instrument 210 can control the instrument 210, processing inputs received from a user and feedback received from the wireless receiver 214. Outputs of the instrument 210, such as the thermal energy emitted by the heating element 216 and a rate of rotation of the motor 220, can be controlled by the controller 226 based on feedback received from the sensing device 120 and/or other sensing devices in the instrument 210.

The wireless receiver 214 can be configured to receive data transmitted wirelessly from the sensing device 120. The wireless receiver 214 can be, for example, a radio frequency identification (RFID) receiver, a near field communication (NFC) receiver, a Bluetooth receiver, a Bluetooth Low Energy receiver, a ZigBee receiver, a Z-Wave receiver or a Wi-Fi receiver or a receiver of any other wireless protocol. Data received by the wireless receiver 214 can be stored in a memory or received by a processor for controlling outputs of the instrument 210 based on the received data. The wireless receiver 214 can wirelessly power the sensing device 120 via radio signals or inductive charging. Properties of the substance 115, such as temperature, pH, sodium, ammonia, lithium, potassium, calcium, dissolved oxygen, $CO_2$, specific gravity, refractive index, viscosity, salinity, conductance, absorbance, fluorescence, or pressure, can be measured by the sensing device 120 and transmitted to the wireless receiver 214.

Figure 3A:
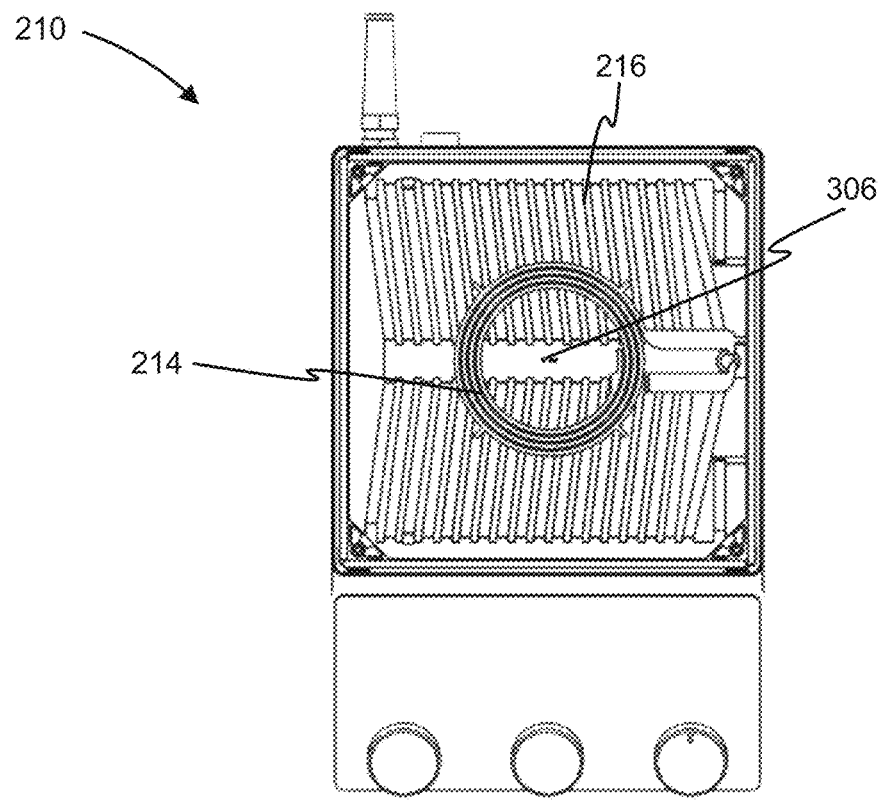
FIG. 3A is a partial see-through top view of a variation of an instrument in the system.

FIG. 3A illustrates an example top view of the instrument 210 with the heating surface 212 removed. As shown in FIG.

3A, the wireless receiver 214 can be placed between the heating element 216 and the heating surface 212. One or more temperature sensors 306 can measure the temperature of the heating element 216 or the heating surface 212. The temperature sensors 306 can use multiple different sensor types to verify calibration or ensure accuracy of the temperature measurements of the heating surface 212. For example, one temperature sensor 306 can be a platinum resistance temperature detector (RTD), and the other temperature sensor 306 can be a thermocouple.

The antenna 214 can function as a temperature sensor by having the antenna constructed of a material that changes resistance due to temperature such as nickel or platinum or titanium or stainless steel or other metals.

The heating element 216 and the antenna 214 can be combined into one mechanical member, for example a spiral shaped member that functions both as a heater and as an antenna. Other shapes can be used for such a combined member.

The heating element 216 and the temperature sensor 306 can be combined into one mechanical member that functions both as a heater and as a temperature sensor.

The heating element 216, the antenna 214, and the temperature sensor 306 can be combined into one mechanical member, for example a spiral shaped member that functions both as a heater and as an antenna and as a temperature sensor. Other shapes can be used for such a combined member.

Figure 3B:
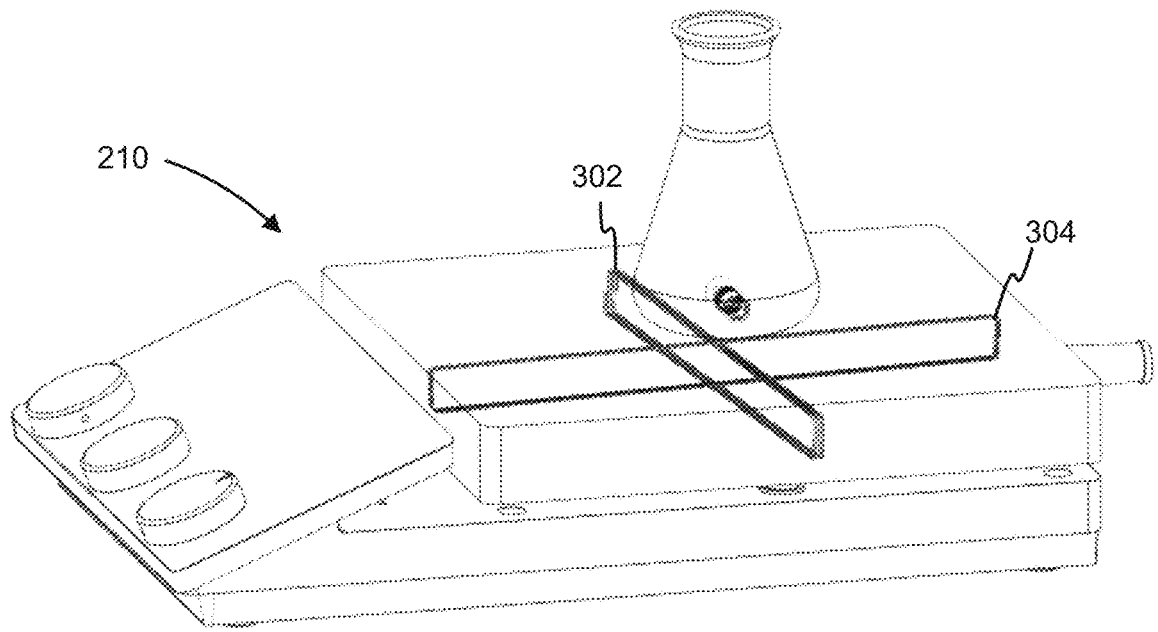
FIG. 3B is a partial see-through perspective view of a variation of an instrument in the system.

FIG. 3B illustrates that the wireless receiver 214 can include a first antenna 302 and a second antenna 304 configured to receive data from, and optionally to transmit data to, the sensing device 120. The first and second antennas 302 and 304 can have different orientations to detect signals from the sensing device 120 in any rotational position of the sensing device 120. Additional or fewer antennas may be included in the instrument 210. The antenna can be made from high temperature Ceramawire or other materials that can withstand the temperature near at the antenna.

Figure 4:
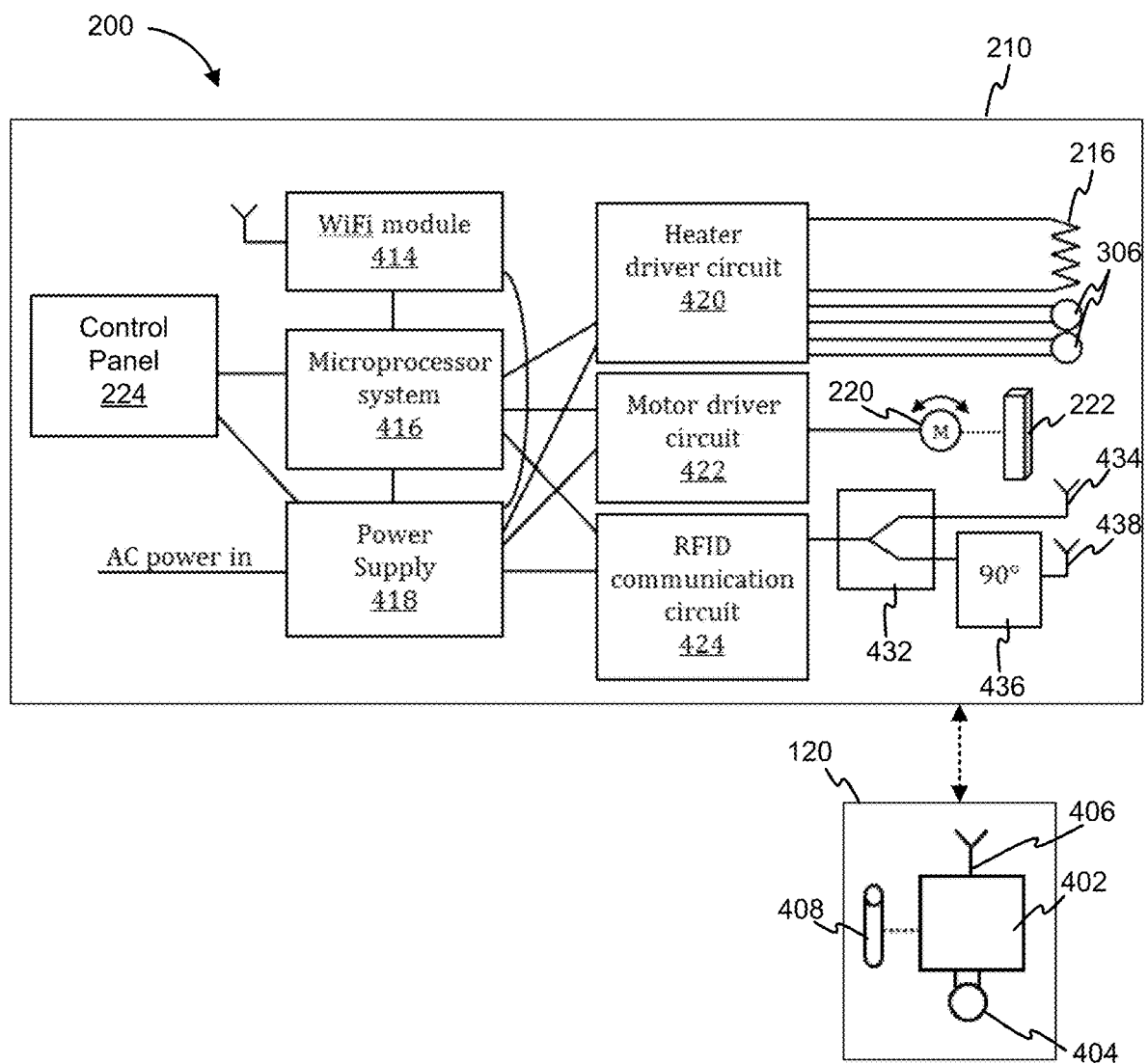
FIG. 4 is a schematic diagram illustrating an example electronic configuration of a system for measuring and regulating properties of contents of a closed container.

FIG. 4 is a schematic diagram illustrating that the sensing device 120 can include an integrated circuit 402 that can read output from a sensor 404 and communicate with an antenna 406. The integrated circuit 402 can contain an internal temperature sensor such as a semiconductor junction. The integrated circuit 402 can include an Analog to Digital converter to convert the signals from the sensors to data for wireless transmission. A magnet 408 can be mechanically coupled to the integrated circuit 402, for example by a housing enclosing the magnet 408 and the integrated circuit 402.

The instrument 210 can include a control panel 224, a WiFi module 414, a microprocessor system 416, a power supply 418, a heater driver circuit 420, a motor driver circuit 422, and a communication circuit 424. Other variations can include additional, fewer, or different components. The microprocessor system 416, WiFi module 414, heater driver circuit 420, motor driver circuit 422, and RFID communication circuit 424 can collectively form the controller 226 described with respect to FIG. 2.

The power supply 418 receives power from an input, such as an AC power source, and provides power to other components of the instrument 210.

Functions of the instrument 210 can be controlled by the microprocessor system 416. The microprocessor system 416 can be, for example, an ARM-based microprocessor system with random access memory, flash memory as well as clock source and other circuits needed to create a microprocessor system, and can include a microprocessor as well as a volatile or non-volatile memory. The microprocessor system 416 can communicate with the control panel 224 to display information or receive user inputs, and can control the heater driver circuit 420 and the motor driver circuit 422. The microprocessor system 416 can communicate with the RFID communication circuit 424 and the WiFi module 414 to receive data transmitted to the WiFi module 414 or the RFID communication circuit 424, or to transmit data from the WiFi module 414 or the RFID communication circuit 424.

The heater driver circuit 420 drives the heating element 216 to provide heat to the heating surface 212. The heater driver circuit 420 can regulate the temperature of the heating element 216 based on inputs received from the one or more temperature sensors 306. The heater driver circuit 420 can regulate the temperature of the heating element 216 based on data received from the microprocessor system 416, such as a temperature of the substance 115 detected by the sensing device 120.

The motor driver circuit 422 drives the motor 220, which in turn rotates the magnet 222 at various speeds and in both directions. A rate of rotation of the magnet 222 can be communicated to the motor driver circuit 222 by the microprocessor system 416, based on a user input received at the control panel 224.

The RFID communication circuit 424 can receive a signal from and transmit a signal to a remote wireless device, such as the sensing device 120. The RFID communication circuit 424 can provide an electronic signal to the sensing device 120 to power the sensing device 120. A signal output by the RFID communication circuit 424 can pass through a splitter 432, which passes the split signal to a first antenna 434 and a 90-degree phase shifter 436 and second antenna 438. The 90-degree phase shift can enable the RFID communication circuit 424 to communicate with the sensing device 120 when the sensing device 120 is in any rotational position. Alternatively, if there is only one antenna in the system, the output from the RFID communication circuit 424 can go directly to the one antenna eliminating the need for a splitter 432 and a 90-degree phase shift 436 and second antenna 438.

Sensing Device

Figure 5A:
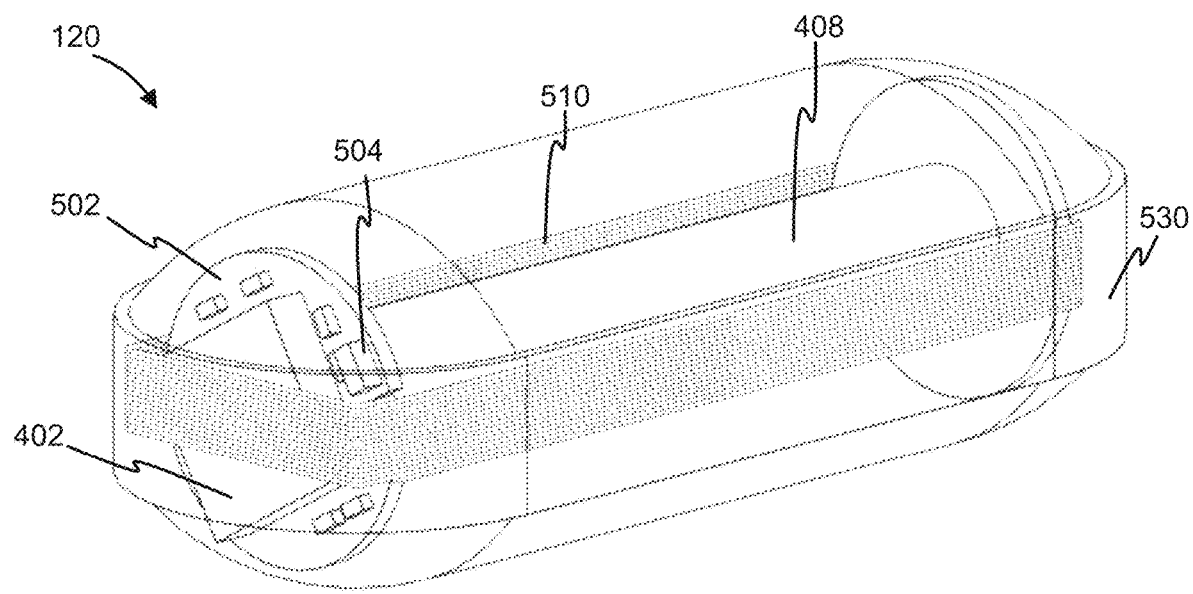
FIGS. 5A-5B illustrate example configurations of sensing devices configured to measure temperature.
Figure 5B:
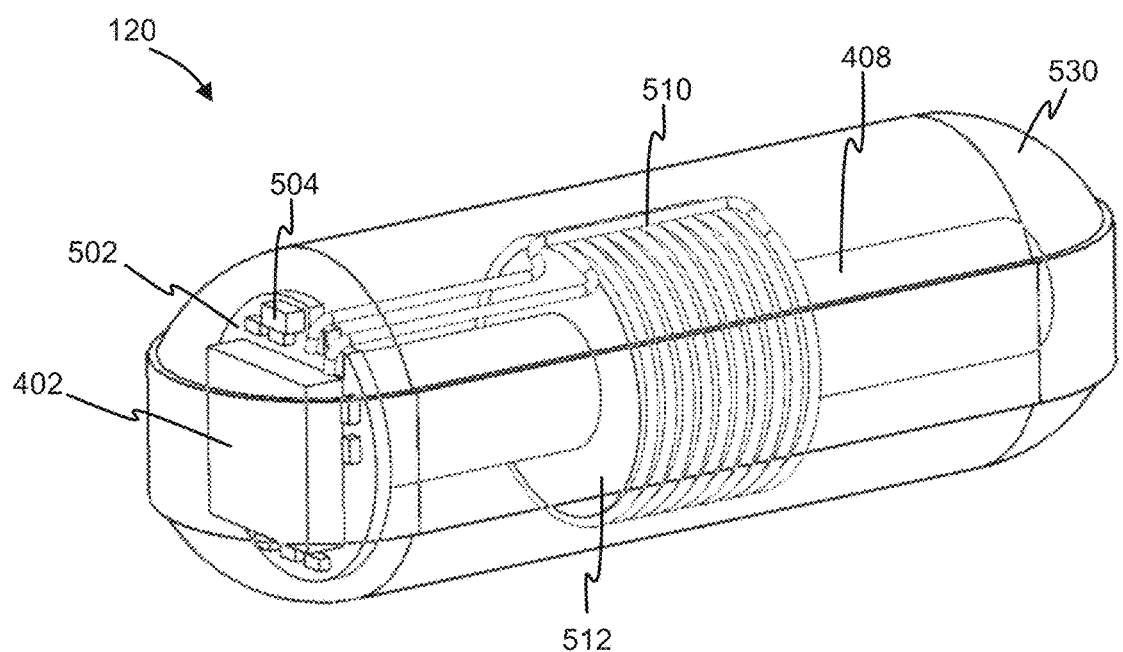

FIGS. 5A-5B illustrate examples of the sensing device 120 configured to measure the temperature of the substance 115. The sensing device 120 can include a circuit board 502 supporting the integrated circuit 402 and a thermistor 504 readable by the integrated circuit 402. A resistance of the thermistor 504 can change in response to a temperature in the substance 115, and the integrated circuit 402 can determine the temperature of the substance 115 by measuring the resistance. The integrated circuit 402 may have an internal temperature sensor like a semiconductor junction, to which the temperature measured by the thermistor 504 can be compared. By having temperature being measured by two different temperature sensor types, aging, calibration, and other reliability issues can be determined because the effect of these reliability issues can be different on the two different temperature sensor types. An internal coil 510, comprising for example 40 AWG copper wire, can form an antenna for the sensing device 120. As shown in FIG. 5A, the internal coil 510 can be wound longitudinally within the sensing device 120. FIG. 5B illustrates that the internal coil 510 can be wound around a ferrite tube 512 concentric to a longitudinal axis of the sensing device 120.

The sensing device 120 can further include the magnet 408, enabling the sensing device 120 to agitate or mix the substance 115 in the container 110. A casing 530 can encapsulate the circuit board 502, internal coil 510, and magnet 408. Many types of encapsulations may be used for the casing 530, such as plastics, glass, rubber, or other materials that can provide a barrier between the substance 115 and electronics internal to the sensing device 120. For example, the casing 530 can be constructed from EFEP from Daikon™, which is a fluoropolymer with a relatively low processing temperature point around 230° C.

The sensing device 120 shown in FIG. 5B can be used to measure viscosity of the substance 115, in addition to measuring the temperature. A wireless receiver, such as the antenna 302 and antenna 304 of the instrument 210, can be oriented perpendicularly to the internal coil 510. As the sensing device 120 is rotated via the magnet 408, the wireless receiver can detect an orientation of the internal coil 510. A rate of the sensing device's rotation can be calculated based on the orientations, and a torque on the motor 220 can be measured. Based on the rate of rotation and the torque on the motor 220, viscosity of the substance 115 can be determined. The rate of rotation of the sensing device 120 can be measured in other manners, such as with a gyroscope or accelerometer.

Figure 6A:
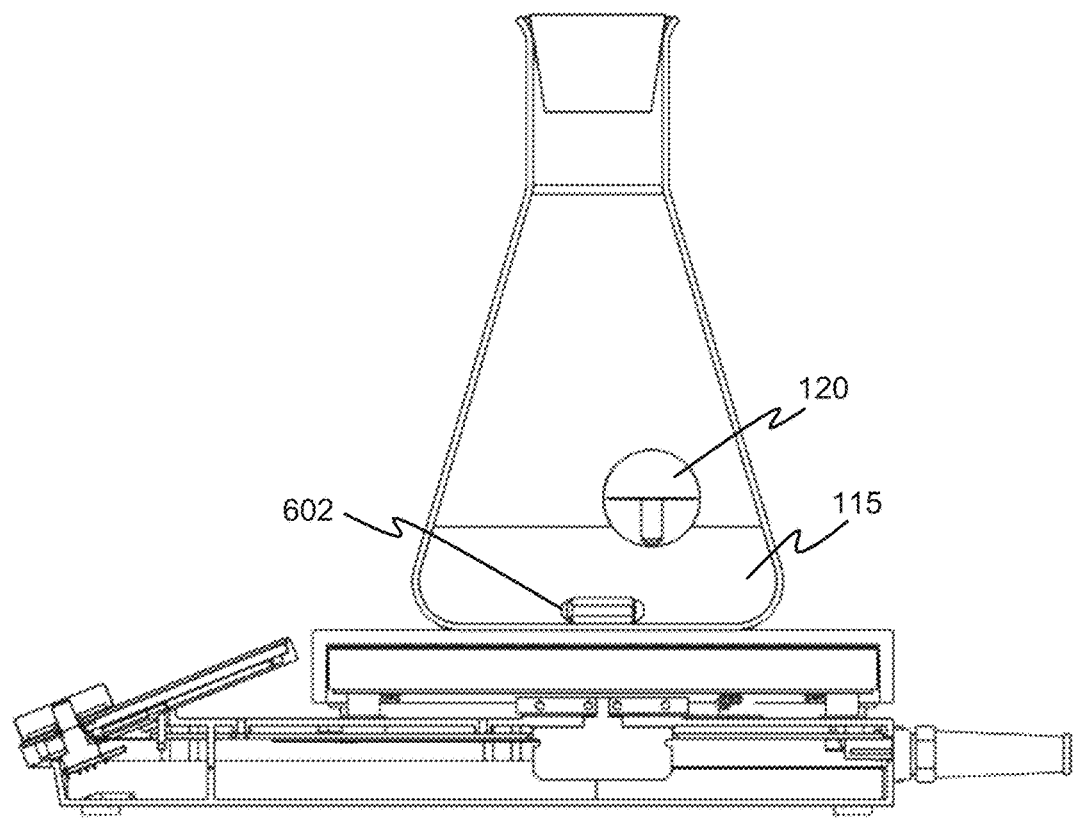
FIGS. 6A-6B illustrate an example floatable sensing device.
Figure 6B:
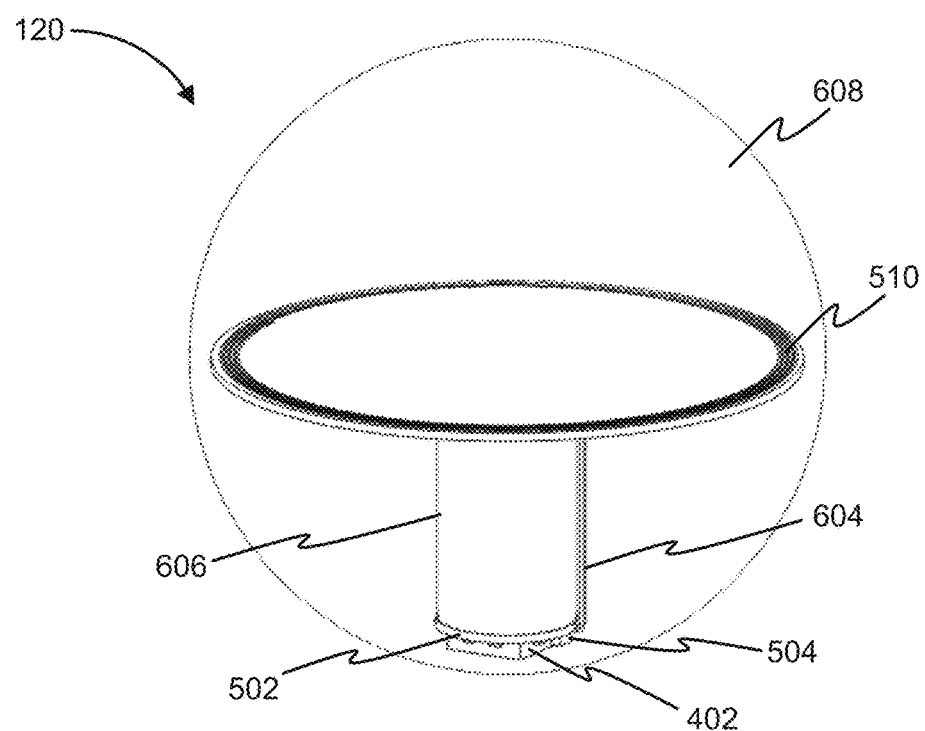

FIG. 6A illustrates another example of the sensing device 120 that is configured to float on the substance 115. An agitator 602 separate from the sensing device 120, such as a magnetic stir bar, can be used to agitate the substance 115 as described above. FIG. 6B illustrates components of the floatable sensing device 120 configured to sense temperature of the substance 115. As shown in FIG. 6B, the floatable sensing device 120 can include the antenna coil 510, the circuit board 502, the thermistor 504, and the integrated circuit 402. Antenna wires 604 can couple the antenna coil 510 to the integrated circuit 402. A ballast 606 stabilizes the sensing device 120, and a plastic overmold 608 encapsulates the electronics and ballast 606. The floatable sensing device 120 can measure the temperature of the substance 115 and transmit the detected temperature to a wireless receiver via the antenna coil 510. Although the floatable sensing device 120 shown in FIG. 6B is a temperature sensor, sensors measuring other properties of the substance 115 can be provided in the floatable sensing device 120 instead of, or in addition to, the temperature sensing components.

Figure 7:
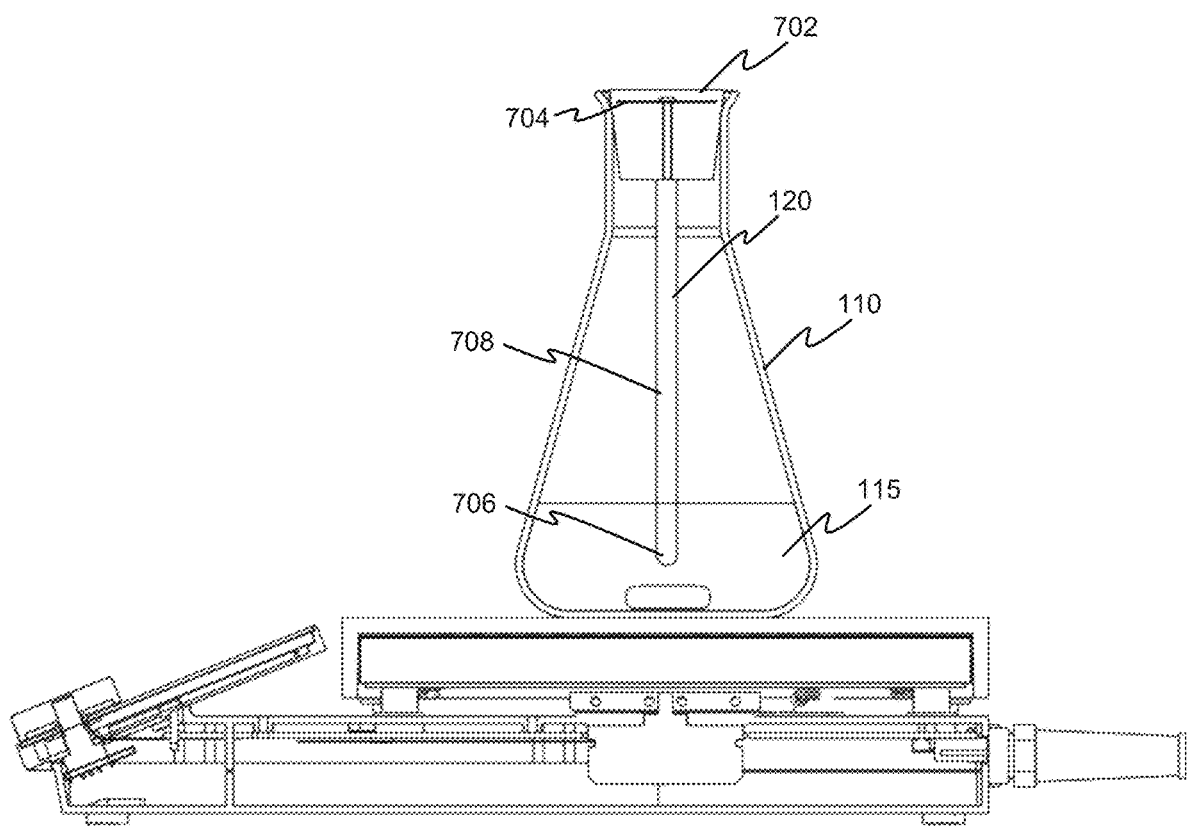
FIG. 7 illustrates an example sensing device coupled to a stopper of the closed container.

FIG. 7 illustrates an example sensing device 120 that is coupled to a stopper 702 closing or sealing a top opening of the container 110. A wireless circuit and antenna 704 can be housed in the stopper 702, and can be coupled to a sensor 706 in contact with the substance 115 by a shaft 708. The sensor 706 can measure properties of the substance 115 and communicate the properties to the wireless circuit and antenna 704, which in turn can transmit data describing the properties to an external receiver. Similar configurations of the sensing device 120 may be provided in a lid or other enclosure, or the container 110 itself, rather than in a stopper 702.

Figure 8:
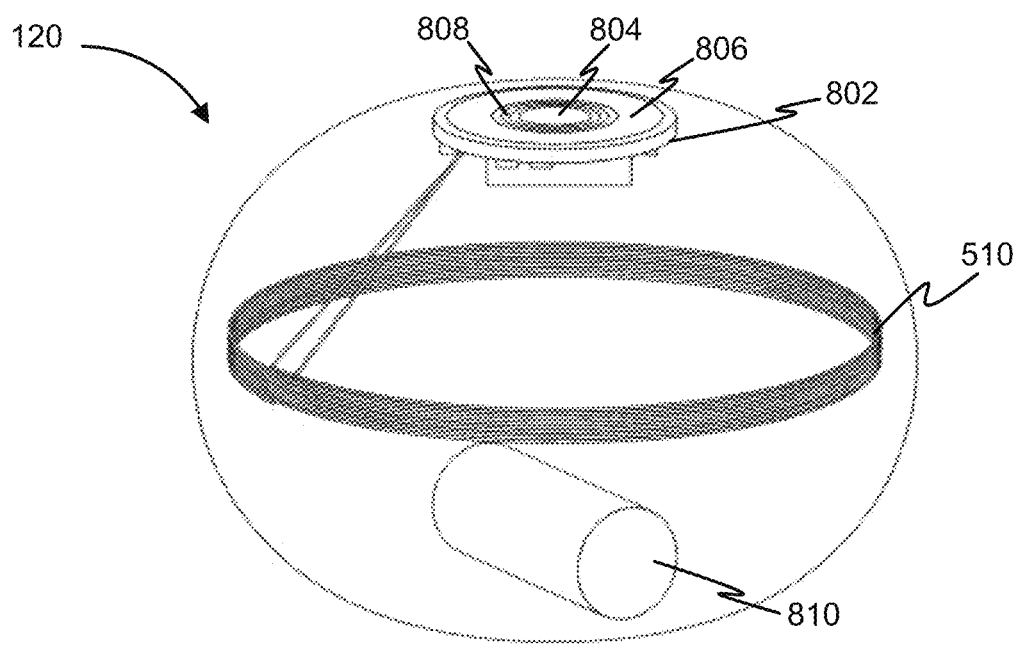
FIG. 8 illustrates an example sensing device configured as a wireless electrochemical sensor.

FIG. 8 illustrates an example sensing device 120 configured as a wireless electrochemical sensor. As shown in FIG. 8, the electrochemical sensor can include a wireless communication circuit 802, a measuring electrode 804, a counter electrode 806, and a reference electrode 808. The wireless communication circuit 802 can receive a voltage difference between the measuring electrode 804 and the counter electrode 806, and report the voltage difference to a wireless receiver via the antenna 510. Based on the voltage data, the wireless communication circuit 802 or a remote system can determine an electrochemical property of the substance 115, which can indicate properties such as a concentration of glucose or alcohol in the substance. The wireless communication circuit 802 can maintain a stable voltage at the measuring electrode 804 using the reference electrode 808 and a potentiostat embedded in the wireless communication circuit 802 (not shown in FIG. 8). The sensing device 120 can further include a magnet and/or ballast 810 allowing the sensing device 120 to function as an agitator and/or stabilizing the sensing device 120. The device in FIG. 8 can be used for conductivity measurement of substance 115 by measuring the conductivity between two electrodes when a specific voltage is applied across them.

Figure 9:
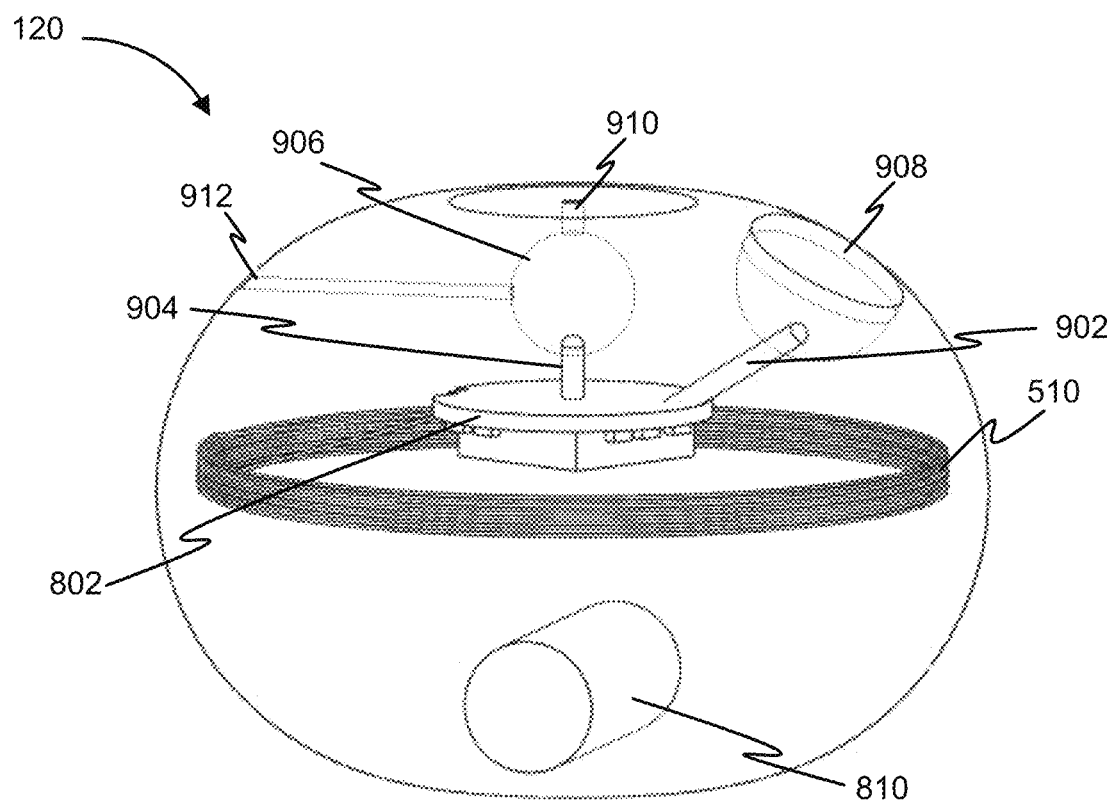
FIG. 9 illustrates an example sensing device configured as a wireless pH sensor.

FIG. 9 illustrates an example sensing device 120 configured as a wireless pH sensor. As shown in FIG. 9, the pH sensor can include the wireless communication circuit 802, a first electrode 902, a second electrode 904, a reference electrolyte 906, H+ selective glass 908, and a porous junction 910. The H+ selective glass 908 is sensitive to hydrogen ions in the substance 115, producing a charge on the first electrode 902. The reference electrolyte 906 produces a charge at the second electrode 904. The wireless communication circuit 802 can measure a voltage difference between the first electrode 902 and the second electrode 904, determine the pH of the substance 115 based on the voltage difference, and report the pH to a wireless receiver via the antenna 510. The porous junction 910 can facilitate slow permeation of the reference electrolyte 906 into the substance 115, creating electrical contact between the reference electrolyte 906 and the substance 115. The reference electrolyte 906 can be periodically refilled via a fill hole 912 in the sensing device 120. The sensing device 120 can further include a magnet and/or ballast 810 allowing the sensing device 120 to function as an agitator and/or stabilizing the sensing device 120.

Figure 10:
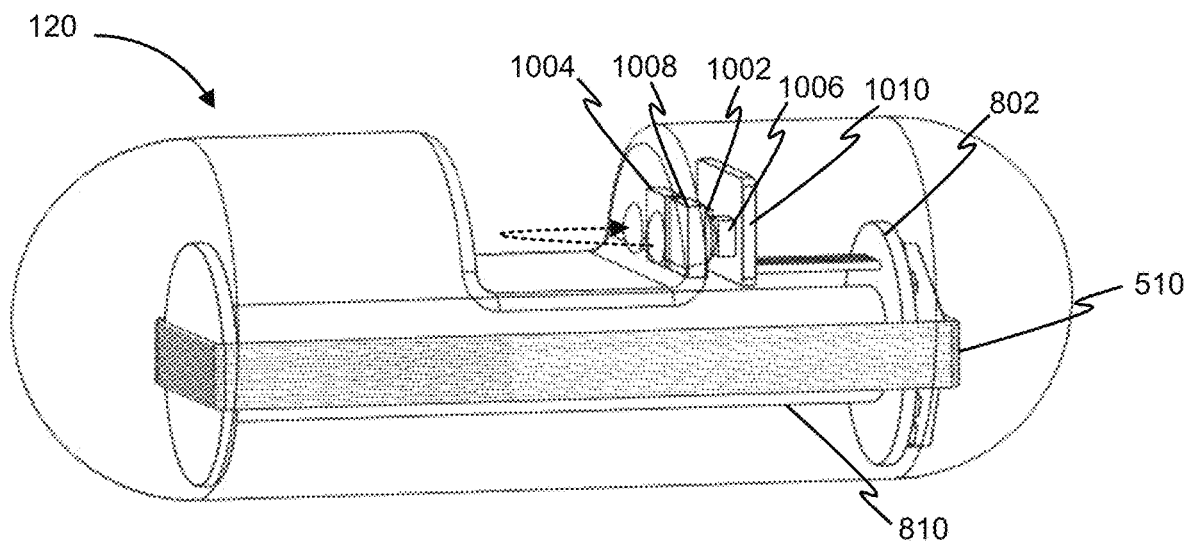
FIG. 10 illustrates an example sensing device configured as a wireless fluorescence sensor.

FIG. 10 illustrates an example sensing device 120 configured as a wireless fluorescence sensor. As shown in FIG. 10, the fluorescence sensor can include the wireless communication circuit 802, a LED light source 1006, an emission filter 1008, a light sensor 1002, a detection filter 1004, and an optics board 1010. A light signal passes from the LED light source 1006 through the emission filter 1008 into the substance 115. The substance 115 can fluoresce in proportion to concentrations of various compounds in the substance 115. The light signal emitted by the fluorescence passes through the detection filter 1004 and onto the light sensor 1002 to the optics board 1010, where the fluorescence can be measured. The optics board 1010 can communicate signals relating to fluorescence to the wireless communication circuit 802, which can transmit the data to a wireless receiver via the antenna 510. Based on the measured fluorescence, the wireless communication circuit 802 or an external device can determine the concentration of an analyte in the substance 115. The LED light source 1006 may be modulated to reduce interference from ambient light. The sensing device 120 can further include a magnet and/or ballast 810 allowing the sensing device 120 to function as an agitator and/or stabilizing the sensing device 120. A version of the sensing device 120 can function as a chemiluminescence sensor by using the light sensor 1002 and the detection filter 1004 to sense luminescence from the substance 115 and communicating the chemiluminescence value with the communication circuit 802 via the antenna 510.

Figure 11:
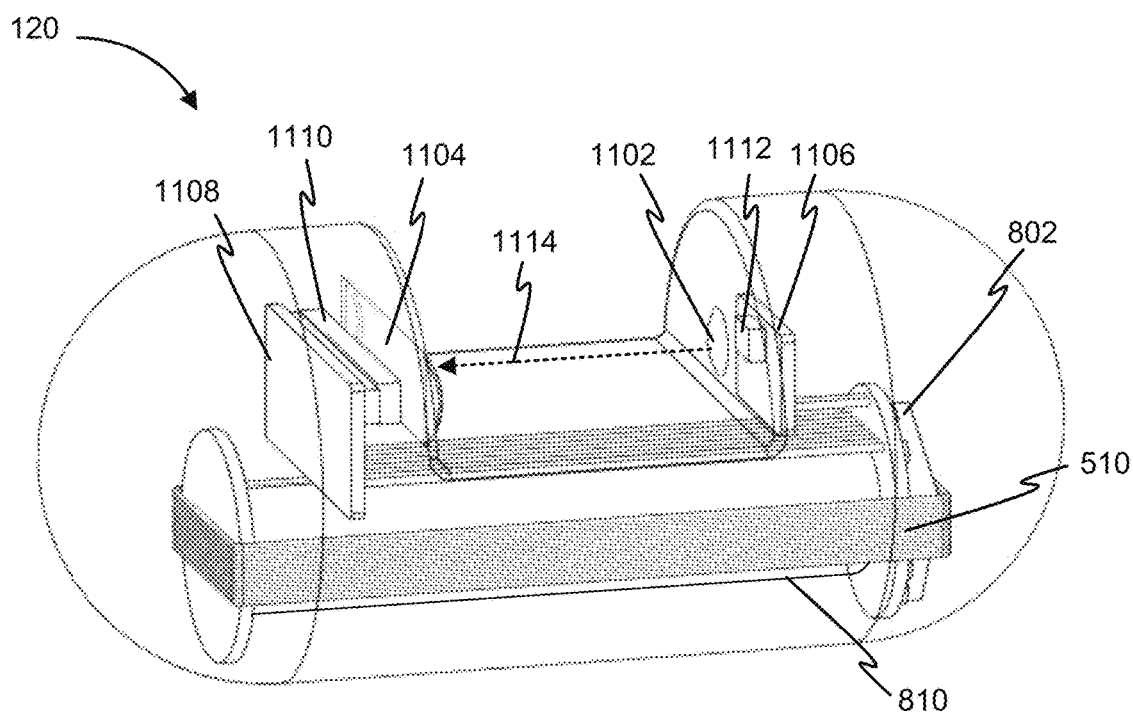
FIG. 11 illustrates an example sensing device configured as a wireless absorbance sensor.

FIG. 11 illustrates an example sensing device 120 configured as a wireless absorbance sensor. As shown in FIG. 11, the absorbance sensor can include the wireless communication circuit 802, a first lens 1102, a second lens 1104, a first optics board 1106, a second optics board 1108, and a linear variable filter 1110. The first optics board 1106 can include a white LED emitter 1112, which emits white light that passes through the first lens 1102 to the second lens 1104 along a light path 1114 through substance 115. The light can pass through the second lens 1104 to the linear variable filter 1110. After passing through the linear variable filter 1110, where the light is filtered, the second optics board 1108 can detect a magnitude of the signal and determine an amount of absorbance of the substance 115 based on the detected light by incorporating a photo diode array or a linear CMOS optical sensor. The second optics board 1108 can communicate signals relating to the absorbance to the wireless communication circuit 802, which can transmit the data to a wireless receiver via the antenna 510. Based on the measured absorbance, the wireless communication circuit 802 or an external device can determine the concentration of an analyte in the substance 115. The LED emitter 1112 may be modulated to reduce interference from ambient light. The sensing device 120 can further include a magnet and/or ballast 810 allowing the sensing device 120 to function as an agitator and/or stabilizing the sensing device 120.

Figure 12:
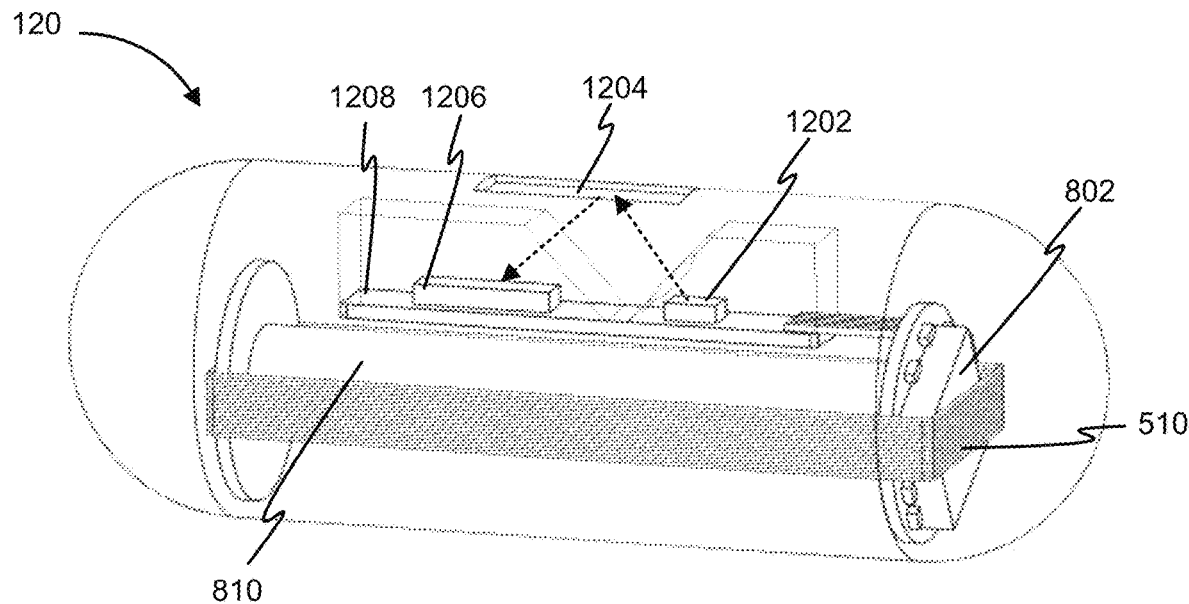
FIG. 12 illustrates an example sensing device configured as a wireless refractometer.

FIG. 12 illustrates an example sensing device 120 configured as a wireless refractometer. As shown in FIG. 12, the refractometer can include the wireless communication circuit 802, an LED light source 1202, a measurement window 1204, a linear array sensor 1206, and a circuit board 1208. The LED light source 1202 can emit a light signal toward the measurement window 1204, which can be a clear window allowing the light signal to reach the substance 115. The light signal can be refracted by the substance 115 and reflected towards the linear array sensor 1206. Based on where the reflected light hits the linear array sensor 1206, the circuit board 1208 can determine an index of refraction of the substance 115. The circuit board 1208 can send signals relating to the index of refraction to the wireless communication circuit 802, which transmits the index of refraction signals to a wireless receiver via the antenna 510. The LED light source 1202 may be modulated to reduce interference from ambient light. There may be an optical filter after the LED light source 1202 to reduce the wavelength projected onto the measurement window 1204 to a limited wavelength range. The sensing device 120 can further include a magnet and/or ballast 810 allowing the sensing device 120 to function as an agitator and/or stabilizing the sensing device 120.

Figure 13:
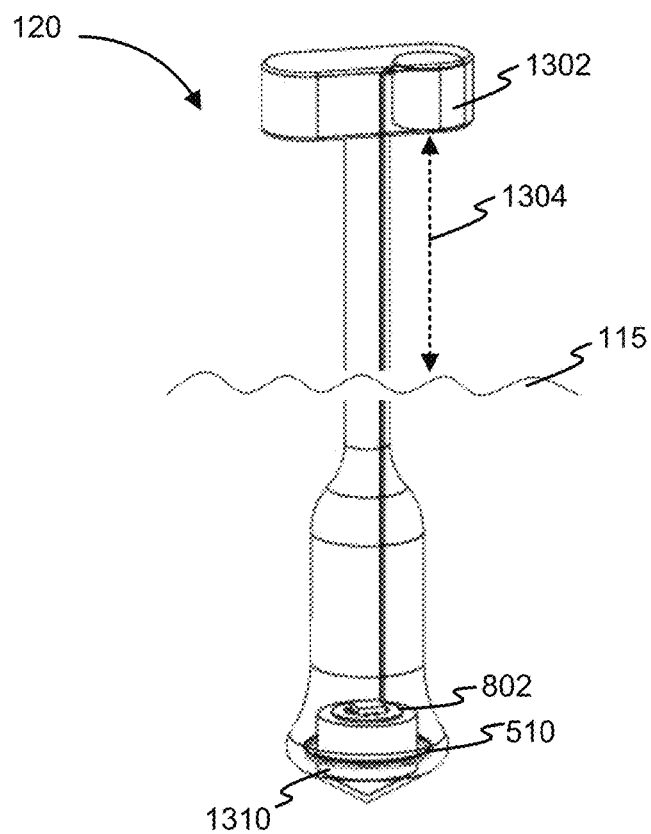
FIG. 13 illustrates an example sensing device configured as a wireless hydrometer.

FIG. 13 illustrates an example sensing device 120 configured as a wireless hydrometer. As shown in FIG. 13, the hydrometer can include the wireless communication circuit 802 and an ultrasonic sensor 1302. The sensing device 120 shown in FIG. 13 can float on the substance 115 at a height proportional to the specific gravity of the substance 115. The ultrasonic sensor 1302 can emit an ultrasound wave toward the surface of the substance 115 and detect a reflection of the emitted wave. The wireless communication circuit 802 can determine a distance 1304 between the ultrasonic sensor 1302 and the surface of the substance 115 based on the detected reflection and calculate the specific gravity of the substance 115 based on the determined distance. The wireless communication circuit 802 can transmit the specific gravity to a wireless receiver via the antenna 510. The sensing device 120 can further include a ballast 1310 to stabilize the sensing device 120. The distance to the liquid can be measured optically, alternatively, the level to which the sensing device is immerged into the liquid can be measured using resistive sensing pads or by optical means.

Regulating Properties Based on Feedback

Figure 14:
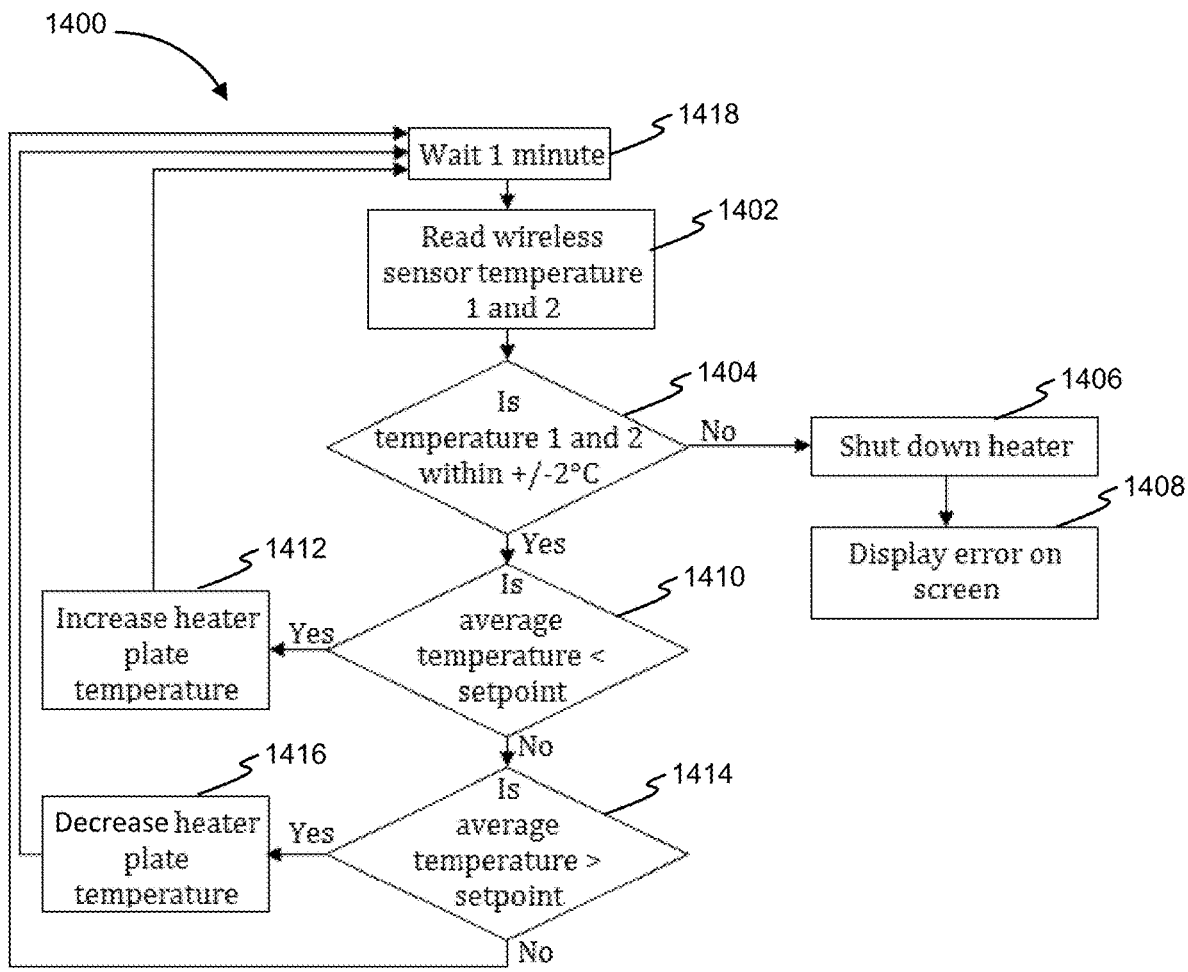
FIG. 14 is a flowchart illustrating an example process for regulating temperature of a substance based on feedback received from a wireless sensing device.

FIG. 14 is a flowchart illustrating an example process 1400 for regulating the temperature of the substance 115 based on feedback received from the wireless sensing device 120. The process 1400 is described with respect to the hot plate system 200, but a similar process can be used to regulate temperature in any other system. The process 1400 can be performed by the controller 226.

As shown in FIG. 14, the controller 226 can read 1402 the temperature from two sensors in the sensing device 120, such as the thermistor 504 and a temperature sensor in the integrated circuit 402. The controller 226 can determine 1404 whether a difference between the temperatures detected by the two sensors is within a threshold difference (e.g., +/−2° C.). If the difference is greater than the threshold difference, the controller 226 can shut down 1406 the heating element 216 and display 1408 an error on the control panel 224. If the difference is less than the threshold difference, the controller 226 can calculate an average of the two temperatures and determine 1410 whether the average is less than a setpoint. The controller 226 can compare a different temperature to the setpoint, such as the temperature output by one of the two sensors.

If the average temperature is less than the setpoint, the controller 226 can increase 1412 the heating element 216 temperature. If the controller 226 determines 1414 the average temperature is greater than the setpoint, the controller 226 can decrease 1416 the heating element 216 temperature. The controller 226 can compare the average temperature to two or more different setpoints. For example, the controller 226 can determine in step 1410 whether the average temperature is less than a lower setpoint and determine in step 1414 whether the average temperature is greater than an upper setpoint. The controller 226 can then wait 1418 a specified amount of time, such as one minute, before repeating process 1400 to continue regulating the temperature of the substance 115. The wait time 1418 can be less than 1 minute.

Figure 15:
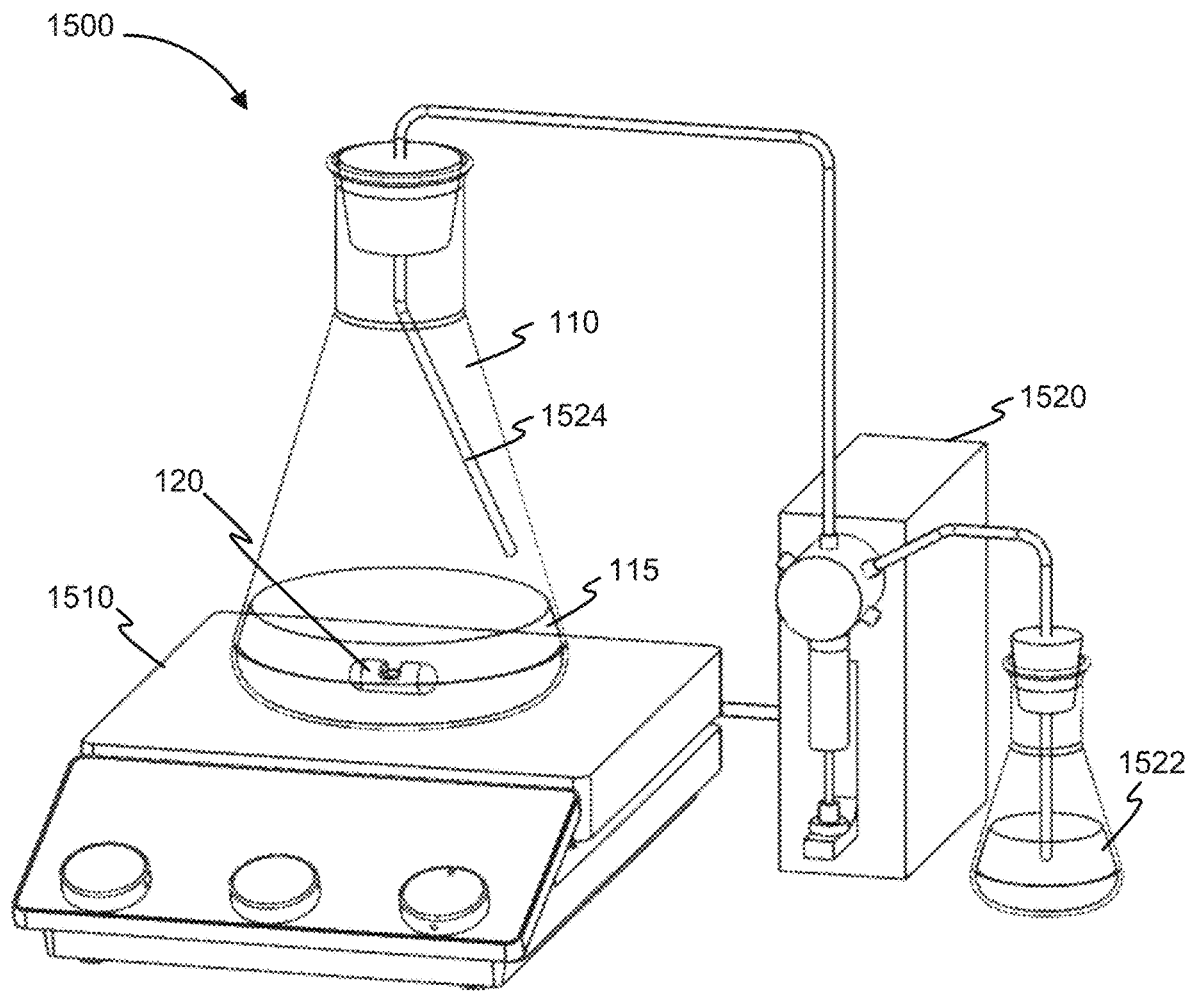
FIG. 15 illustrates an example system for controlling reagent delivery based on feedback received from a wireless sensing device.

FIG. 15 illustrates a system 1500 for controlling reagent delivery based on feedback received from the sensing device 120. As shown in FIG. 15, the system 1500 can include a control unit 1510 and a syringe dispenser pump 1520 configured to pump specified quantities of a reagent 1522 into the container 110 via the dispensing nozzle 1524. The sensing device 120 positioned in the substance 115 can measure one or more properties of the substance, such as fluorescence, absorbance, index of refraction, pH, an electrochemical signal, fluid level, or specific gravity, and wirelessly transmits data describing the measured properties to the control unit 1510. The control unit 1510 can be programmed with a desired setpoint for the measured property and can be configured to control the syringe dispenser pump 1520 to deliver the reagent 1522 to the container 110 to achieve the desired setpoint.

For example, the setpoint can be a desired pH for the substance 115 and the reagent 1522 can be an acid or base. The control unit 1510 receives the pH measured by the sensing device 120 and compares the measured pH to the desired pH. If the measured pH is different from the desired pH, the control unit 1510 can cause the syringe dispenser pump 1520 to dispense a specified volume of the reagent 1522 into the container 110 until the desired pH is achieved. As another example, the setpoint can be a desired absorbance, fluorescence, or electrochemical signal, corresponding to a desired concentration of a particular compound in the substance 115 that can be altered by adding the reagent 1522. The control unit 1510 receives the absorbance, fluorescence, or electrochemical signal measured by the sensing device 120, and compares the received data to the setpoint. If the received data is different from the setpoint, the control unit 1510 can cause the syringe dispenser pump 1520 to dispense a specified volume of the reagent 1522 into the container 110 until the desired property is achieved.

The control unit 1510 and syringe dispenser pump 1520 can be incorporated into a single device instead of the two devices shown in FIG. 15. Furthermore, the control unit 1510 may control multiple syringe dispenser pumps 1520 to deliver multiple reagents 1522 to the substance 115. The system can be configured to remove some or all of substance 115 from container 110, for example when a specific property of substance 115 has been achieved or to control the level of substance 115.

Methods for Use

Figure 16:
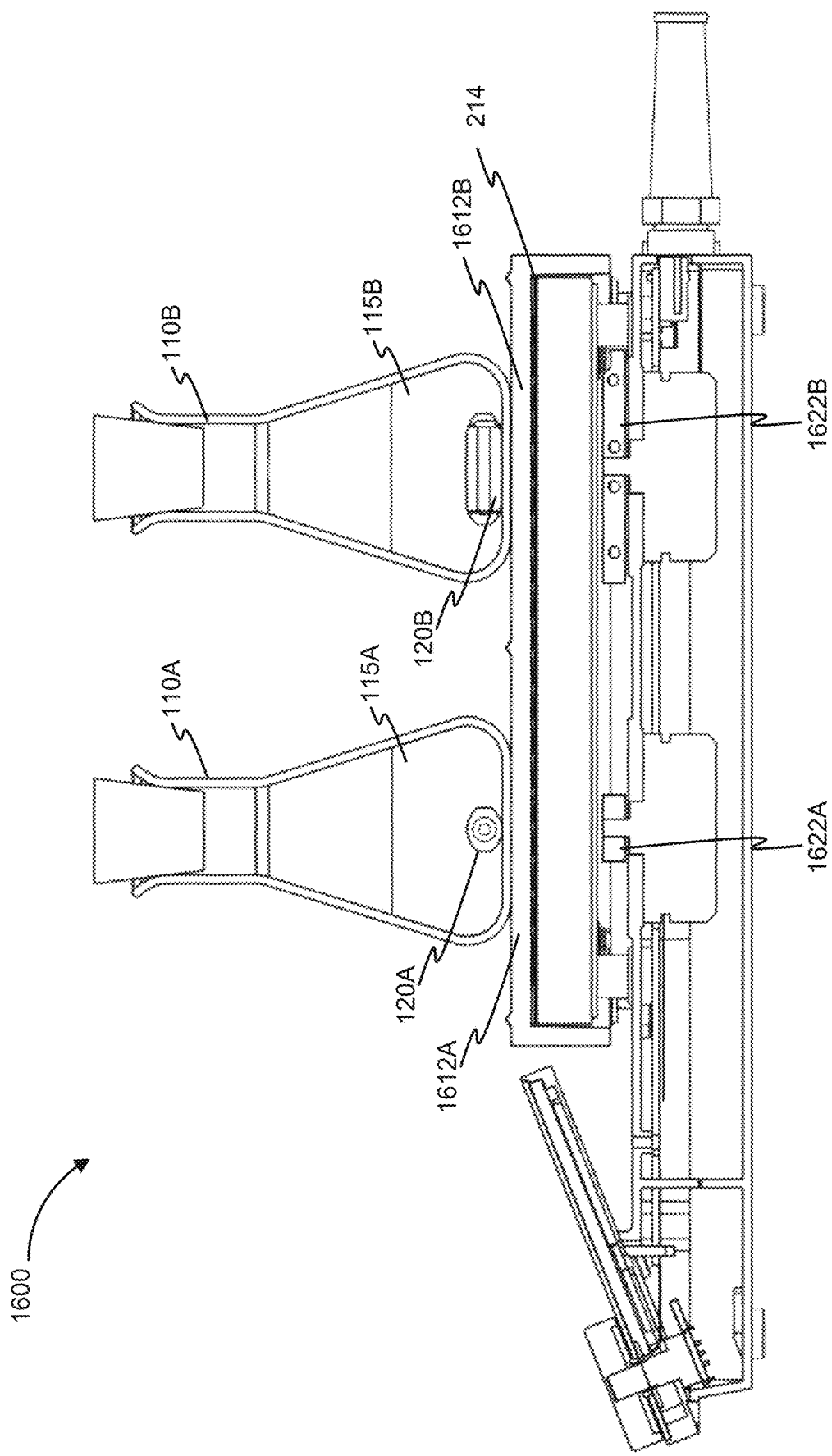
FIG. 16 illustrates an example hot plate system regulating properties of multiple substances.

FIG. 16 illustrates an example hot plate system 1600 including multiple containers 110A and 110B, as well as multiple sensing devices 120A and 120B. The first sensing device 120A can be rotated by a first magnet 1622A, agitating and measuring properties of a first substance 115A in the first container 110A as it is rotated. The second sensing device 120B can be rotated by a second magnet 1622B, agitating and measuring properties of a second substance 115B in the second container 110B as it is rotated. The first substance 115A can be heated by a first heating surface 1612A, and the second substance 115B can be heated by a second heating surface 1612B. The wireless receiver 214 receives data from the sensing devices 120A and 120B, from which outputs of the hot plate system 1600 can be controlled. For example, based on data received from the sensing device 120A, the hot plate system 1600 can increase or decrease the temperature of the first heating surface 1612A or can increase or decrease the rate of rotation of the first magnet 1622A.

Figure 17:
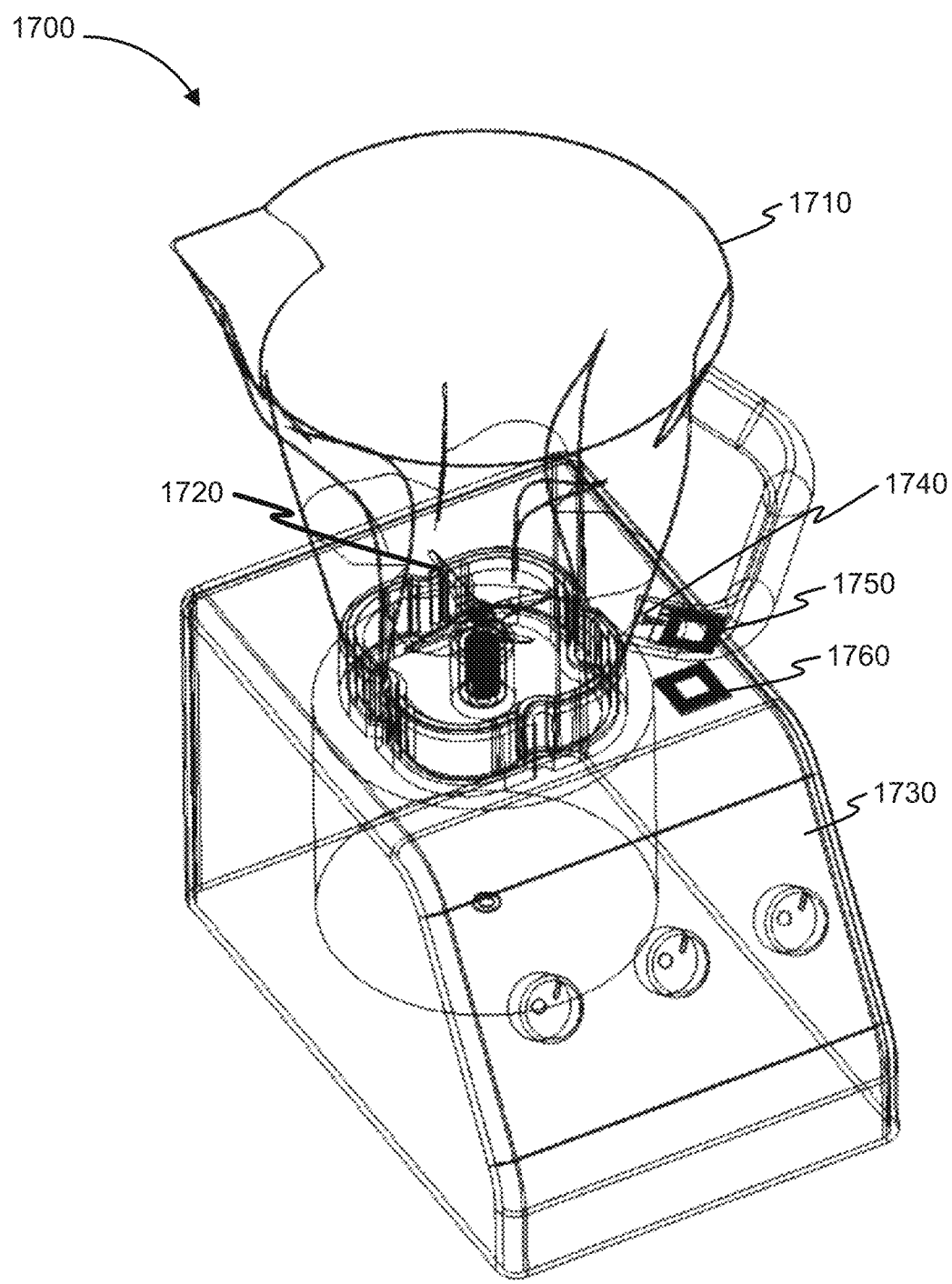
FIG. 17 illustrates an example blender system using a wireless sensing device.

FIG. 17 illustrates an example blender system 1700 including a wireless sensing device 120. In the example of FIG. 17, a blender pitcher 1710 can contain a substance to be blended (not shown). Blades 1720 can rotate within the blender pitcher 1710 to break up and blend the substance. The sensing device 120 can be incorporated into the blades 1720 to measure properties of the substance as it is blended. A control unit 1730 can receive user inputs to increase or decrease the rate of rotation of the blades 1720 and can receive feedback from the sensing device 120 to automatically increase or decrease the rate of rotation of the blades 1720 based on the detected properties of the substance in the blender pitcher 1710. A temperature sensor 1740 built into the blender pitcher 1710 can detect temperature of the substance to be blended and via the antenna 1750 in the blender pitcher 1710 transmit the temperature information via a receiver antenna 1760 in the control unit 1730.

Figure 18A:
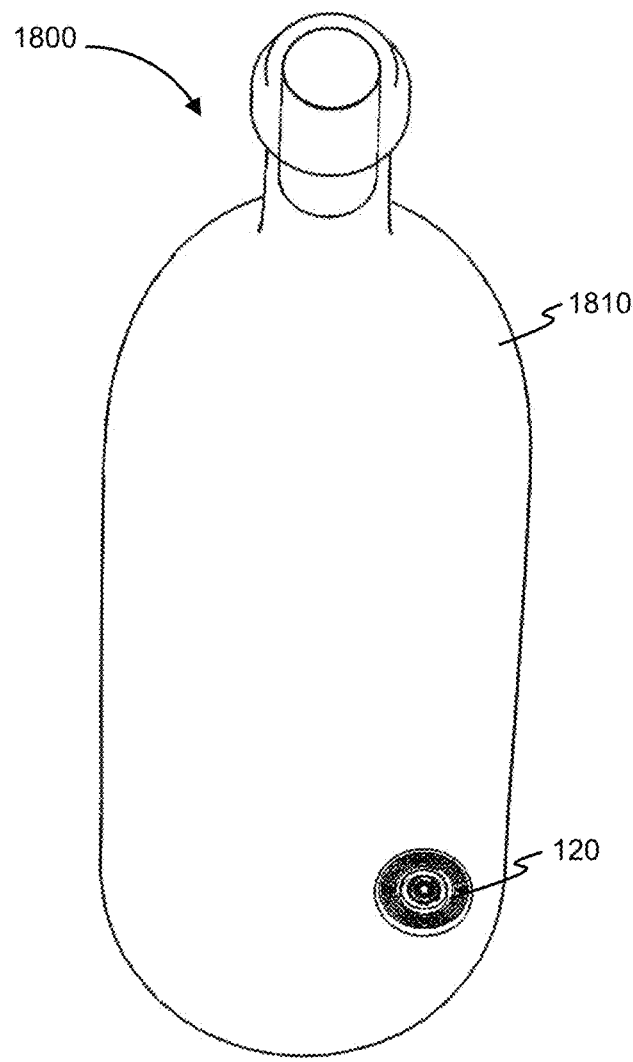
FIGS. 18A-18B illustrates an example wine monitoring system using a wireless sensing device.
Figure 18B:
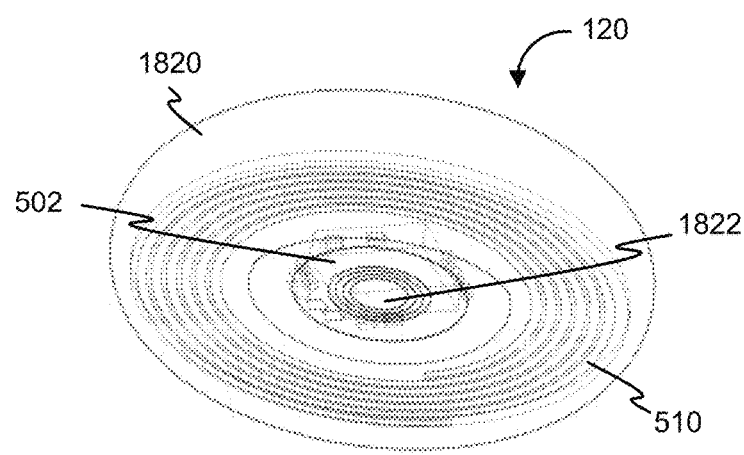

FIGS. 18A-18B illustrate an example wine monitoring system 1800. In the example of FIG. 18A, a wireless sensing device 120 can be placed in a wine bottle 1810 before the bottle is sealed and can monitor properties of the wine in the bottle 1810. The sensing device 120 can transmit the measured properties to an external wireless receiver, which can report the properties to a retailer or consumer. For example, the sensing device 120 may report a concentration of thiols, acetic acid, or oxygen in the wine. The retailer or consumer can use the reported information to determine the quality of the wine prior to opening the bottle 1810.

FIG. 18B illustrates an example of the sensing device 120 configured to detect sense properties of the wine that may indicate its quality. The configuration of the sensing device 120 shown in FIG. 18B can include a plastic overmold 1820 with an exposed electrochemical sensing area 1822 on its surface. The electrochemical sensing area 1822 can include one or more of the measuring electrode 804, the counter electrode 806, and the reference electrode 808 described with respect to FIG. 8, and can be configured to detect thiols, acetic acid, oxygen, or other relevant components of the wine. The sensing device 120 can include the circuit board 502 for controlling operations and the antenna 510 for wireless communication with an external device.

Figure 19:
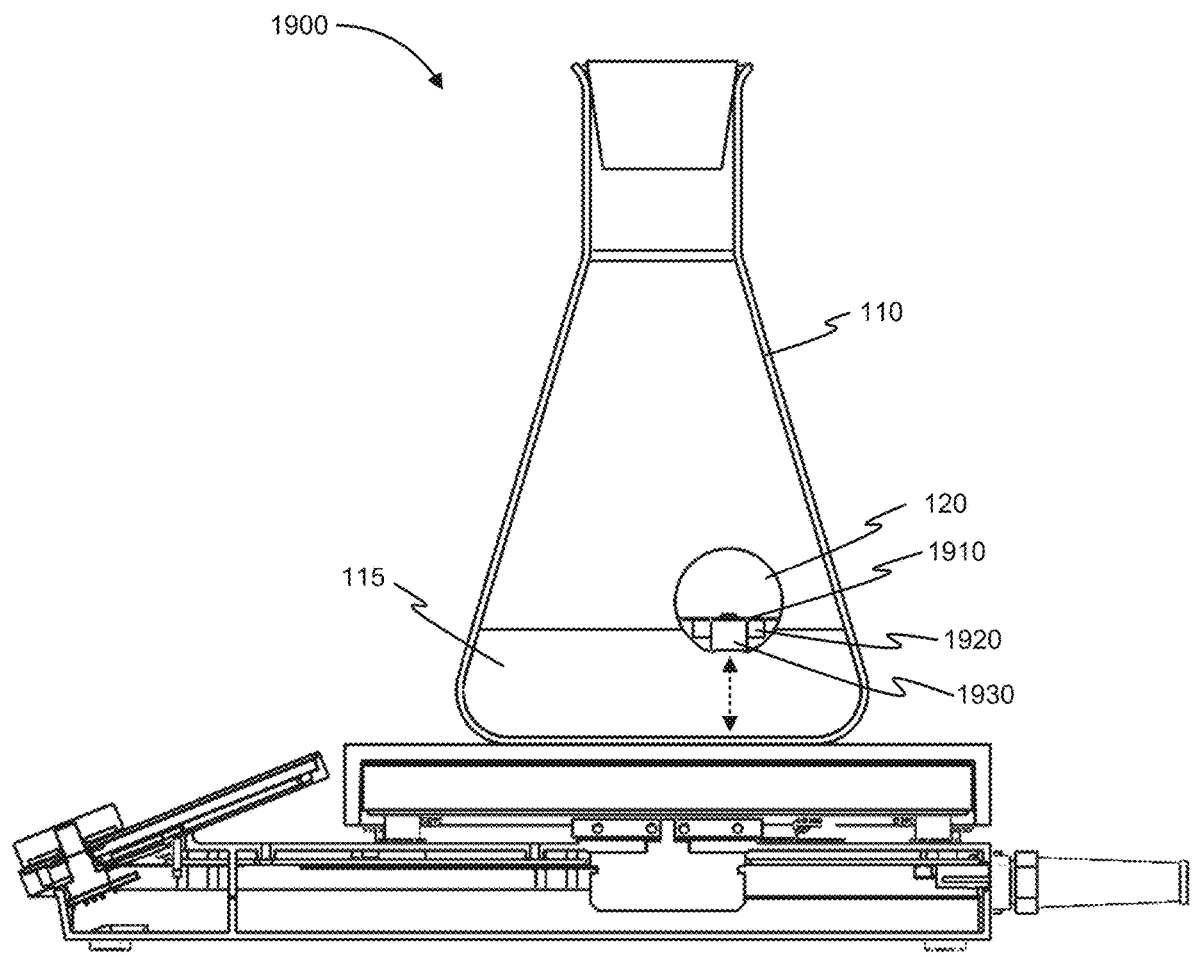
FIG. 19 illustrates an example floatable level sensing device.

FIG. 19 illustrates an example of the sensing device 120 configured to sense the fluid level of substance 115 in a container 110. The sensing device 120 uses an ultrasonic sensor 1930 coupled to a wireless communication circuit and antenna 1910. The sensing device 120 can contain a ballast 1920 for orienting the sensing device 120.

Figure 20A:
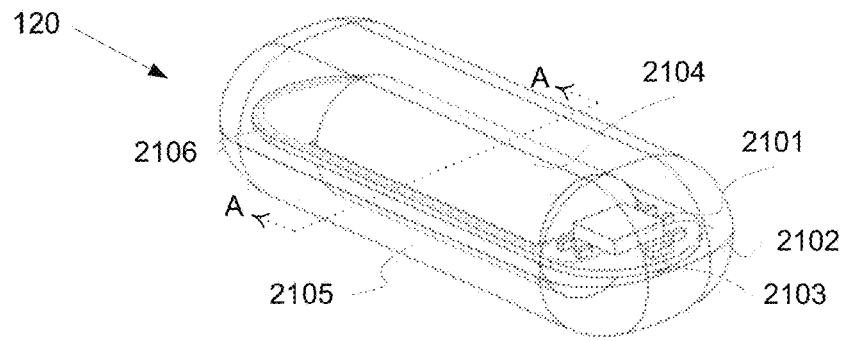
FIG. 20A is a partial see-through perspective view of a variation of the sensing device.

FIG. 20A illustrates a sensing device 120, such as a stir bar, that can be configured to measure the temperature of a substance. The sensing device 120 can have a circuit board 2101 supporting an integrated circuit 2102 and a temperature sensing element 2103 readable by the integrated circuit 2102. The temperature sensing element 2103 can be a thermistor, a RTD, a temperature sensitive crystal, a temperature sensitive capacitor, a semiconductor junction or another device that changes property in response to a temperature change. The temperature sensing element 2103 can be a Platinum RTD or a Nickel RTD or another stable metal that exhibits a resistance change in response to temperature. The resistance of the temperature sensing element 2103 can change in response to a temperature in the substance 115, and the integrated circuit 2102 can determine the temperature of the substance 115 by measuring the resistance. The integrated circuit 2102 may have an internal temperature sensor, such as a semiconductor junction, to which the temperature measured by the temperature sensing element 2103 can be compared. Two different temperature sensor types can be compared, for example, to track aging, calibration of the temperature output data, and other reliability issues (e.g., the effect of these issues can be different on the two different temperature sensor types).

An internal coil 2106 in the circuit board 2101, can form an on-board antenna for the sensing device 120. In the device 120 the internal coil 2106 can be planar with the circuit board 2101. The sensing device 120 can have a magnetic member 2104. The magnetic member 2104 can enable the sensing device 120 to agitate or mix the substance. The magnetic member 2104 can be a magnet or a piece of metal that responds to external magnetic forces (e.g., ferrous metal).

The sensing device 120 can have a casing 2105. The casing 2105 can encapsulate in a fluid-tight chamber the circuit board 2101 and magnetic member 2104. The casing 2105 can be made from plastics, glass, rubber, ceramic, epoxy or combinations thereof. The casing 2105 can be a barrier between the substance 115 and electronics internal to the sensing device 120.

Figure 20B:
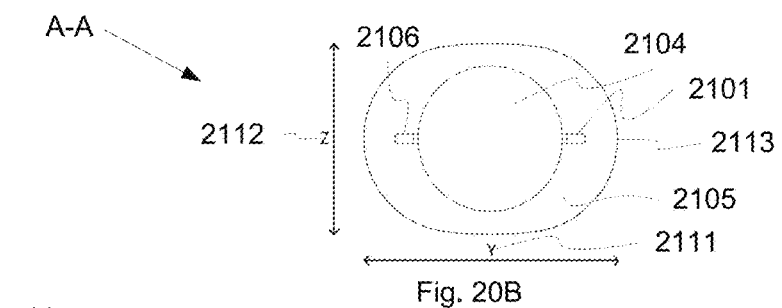
FIG. 20B is a variation of cross-section A-A of the sensing device.

FIG. 20B shows that the on-board antenna 2106 in the sensing device 120 can be planar with the circuit board 2101. The on-board antenna 2106 can be oriented to be in a plane parallel with the plane of a receiving antenna. For example, the receiving antenna can be placed flat with the horizontal plane (e.g., for systems where the receiving antenna is sensitive to a vertical field, such as in case of a coil antenna). The on-board antenna 2106 in the sensing device 120 can then be oriented flat with the horizontal plane. For example, the width of the sensing device Y (2111) can be larger than the height Z (2112) of the sensing device 120, and the edge 2113 of the sensing device can be non-flat at the external surface point 2113 closest to where the sensing device 120 can rest. For example, the area near external surface point 2113 can be rounded or an edge or any non-flat area that would make the sensing device 120 not be able to rest at that point but would promote the sensing device 120 to lay in such a way that the circuit board 2101 is parallel to the horizontal plane.

Figure 20C:
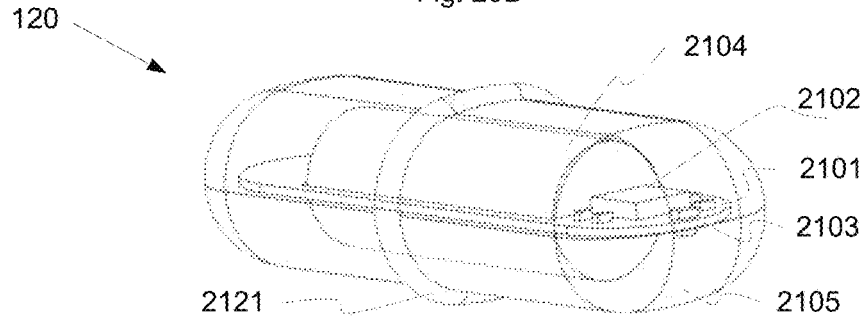

FIG. 20C shows that the sensing device 120 can have a center "ring" 2121 for promotion of stable rotation as well as lifting the sensor off the bottom thereby increasing the contact with the substance 115 rather than the floor surface of a container 110 thereby enhancing thermal contact.

Figure 20D:
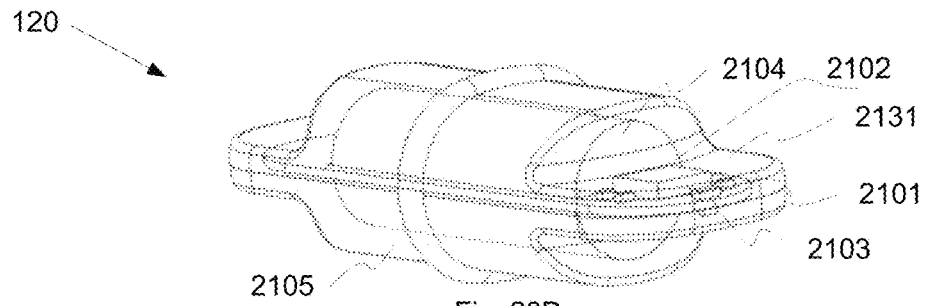

FIG. 20D shows a sensing device 120 with a cut-out area 2131 to lessen the amount of casing material 2105 between the temperature sensing element 2103 and the substance as well as reducing casing material 2105 between the internal sensing element in the integrated circuit 2102 and the substance.

Figure 20E:
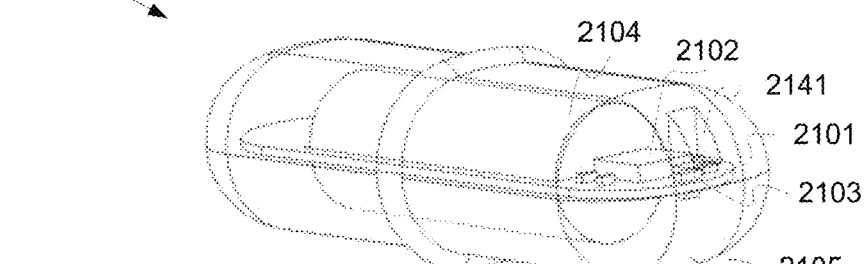

FIG. 20E shows a sensing device 120 with a high thermal conducting element 2141 inserted in the casing 2105 to promote better thermal conductivity between the substance and the temperature sensing element 2103 as well as better thermal conductivity between the substance and the temperature sensor in the integrated circuit 2102.

FIG. 20F shows a sensing device 120 with casing 2105 where a protrusion 2151 extends from the main body to hold a sensor element like a temperature sensor 2103. The protrusion 2151 could be the temperature sensing element 2103 itself. The shape of sensing device 120 is such that it is biased to have a side that faces up. This can be needed if having sensing elements that need o be oriented in a certain direction.

Figure 20G:
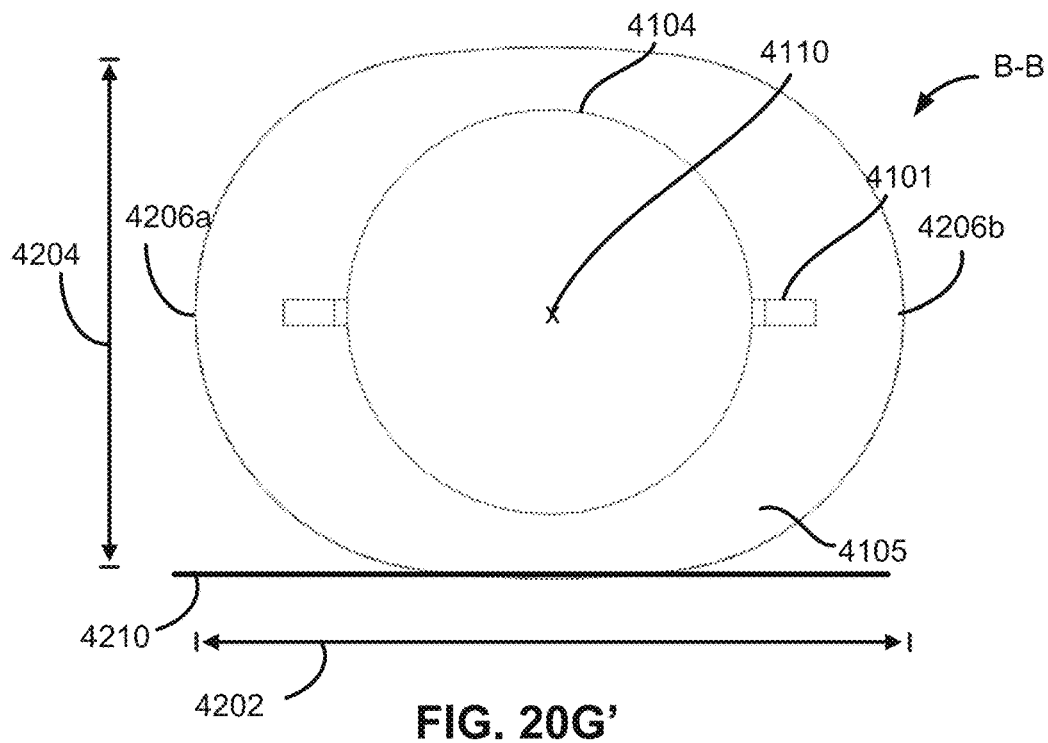
FIGS. 20G through 20G"" are variations of cross-section B-B of the sensing device.
Figure 20G:
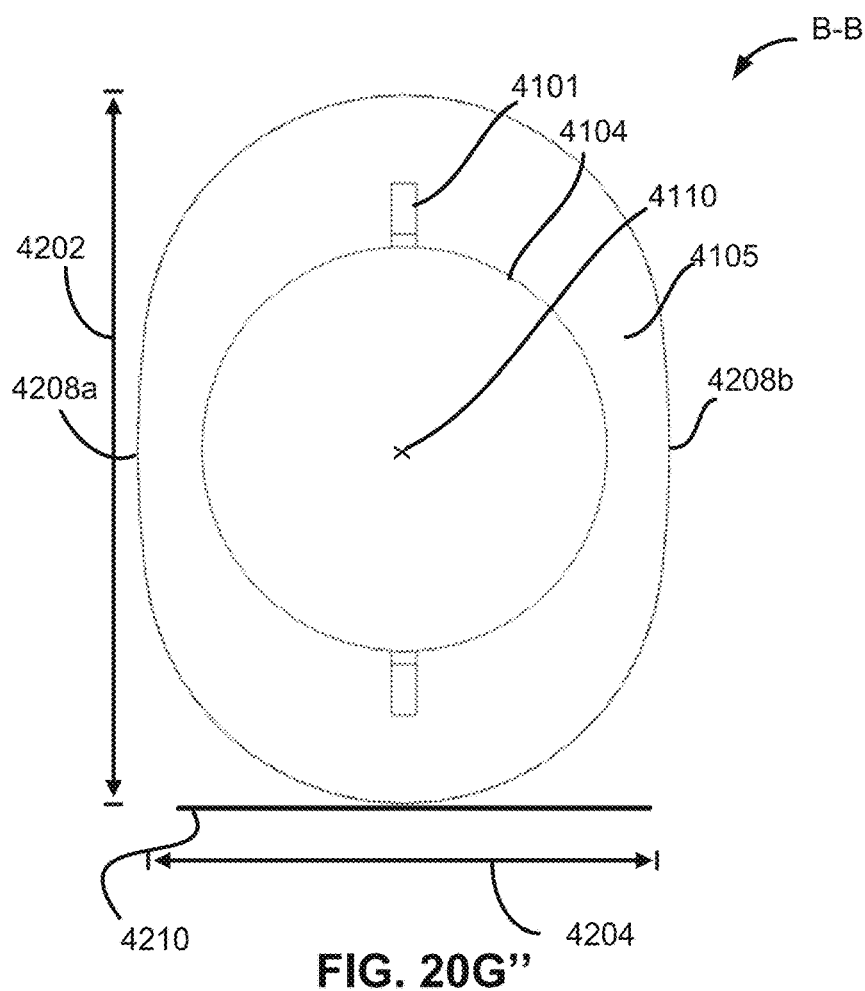

FIG. 20G shows the cross-section B-B the center of the sensing device 120. This shows that the point 2164 can be biased upward by having half-horizontal dimension 2162 being larger than below-midline vertical dimension 2161 and by having above-midline vertical dimension 2163 being larger than half-horizontal dimension 2162 where the midline between 2161 and 2163 defines the vertical center of gravity for the sensing device 120. The egg-like cross-sectional shape can be located throughout the sensing device 120 or can be located at each end or in the center of sensing device 120.

FIGS. 20G' and 20G" are variations of cross-section B-B and illustrates that the sensing device 120 can have the antenna planar with the circuit board 4101, and for optimal communication with a receiving antenna, the other various electronic elements of the sensing device 120 can be oriented in respect to the receiving antenna. For systems where the receiving antenna is sensitive to a vertical field, i.e. in case the receiving antenna is a coil antenna that is placed parallel with a horizontal plane, the antenna in the sensing device 120 can stay parallel to the horizontal plane for optimal communication. To enable this, the sensing device 120, with a width 4202, a height 4204, and a center of gravity 4110, can be shaped such that the width 4202 is longer than the height 4204, and when the antenna is parallel to the horizontal plane, the sensing device 120 is in a stable orientation.

The sensing device 120 can have side faces 4206a, 4206b that can be shaped so the sensing device 120 can have a weak base of support on its side faces 4206a, 4206b, such as having generally rounded faces (see FIG. 20G") or having edges 4216a, 4216b (see FIG. 2G'"), and having top and bottom faces 4208a, 4208b that are shaped such that the sensing device 120 would have a strong base of support on its top and bottom faces 4208a, 4208b, such as having a generally flat area serving as the base of support. FIGS. 20G' and 20G" illustrate that the sensing device 120 can have a flattened oval cross-section shape that encourages the sensing device 120 to lie flat on the top or bottom faces 4208a, 4208b.

In the stable equilibrium orientation, the object's center of gravity can be closest to the ground of all orientations. With the width 4202 longer than the height 4204, as illustrated in FIG. 20G', the sensing device 120 can have a stable orientation when the antenna is parallel to the horizontal plane and the center of gravity 4110 is closest to the floor surface 4210.

As illustrated in FIGS. 20G" and 20G'" when the sensing device 120 is in an unstable orientation, because of the weak base of support, with a slight disturbance the center of gravity 4110 drops to a lower point and the sensing device 120 would then rotate until it reaches the most stable equilibrium seen in FIG. 20G'.

FIG. 20G"" illustrates that the sensing device 120 can have lateral vertices 4216a, 4216b that are offset from one another. The sensing device 120 can rotate from this position to orient the antenna parallel to the horizontal plane once the sensing device 120 is in a stable equilibrium orientation. The sensing device 120 can have lateral-facing pinwheels on opposite ends that can act as on-board propulsion.

FIG. 20H shows a sensing device 120 with casing 2105 where a protrusion 2171 extends from the main body to hold a sensor element like a temperature sensor 2103. The protrusion 2171 could be the temperature sensing element 2103 itself.

FIG. 20i shows a sensing device 120 with casing 2105 where a protrusion 2181 extends from the main body to hold a sensor element like a temperature sensor 2103. The protrusion 2181 could be the temperature sensing element 2103 itself.

FIG. 20J shows a sensing device 120 with casing 2105 where a disk-shaped protrusion 2191 extends from the main body to hold a sensor element like a temperature sensor 2103.

Figure 20K:
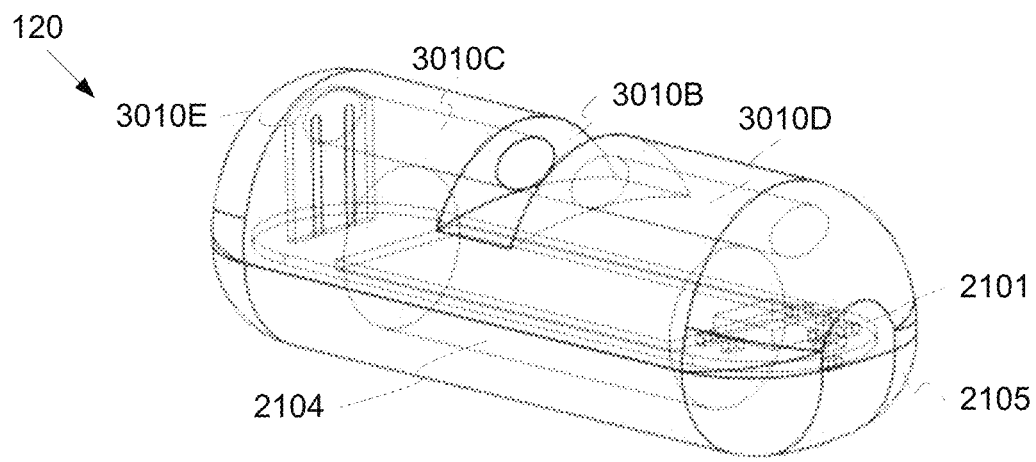

FIG. 20K shows a sensing device 120 for capturing a sample portion. The sensing device 120 can have a magnetically effected member 2104 embedded in an encapsulation 2105 along with an optional electronics board 2101 and sensor board 3010E. A sample can be collected in a cavity 3010C and 3010D via the opening 3010B. The sample collected in cavity 3010C can optionally be analyzed via the electronic sensor board 3010E. The sample collection can happen when the device is dropped into a liquid of interest. If the sensing device in 120 is rotated then the liquid collected in cavities 3010C and 3010D can be exposed to a centrifuge function and the collected liquid can experience centrifugation. An example is if the sensing device in 120 is dropped in a whole blood sample and spun around by exposing the device to a rotating magnetic field then the whole blood can see separation of blood constituents in sample chambers 3010C and 3010D.

Figure 20L:
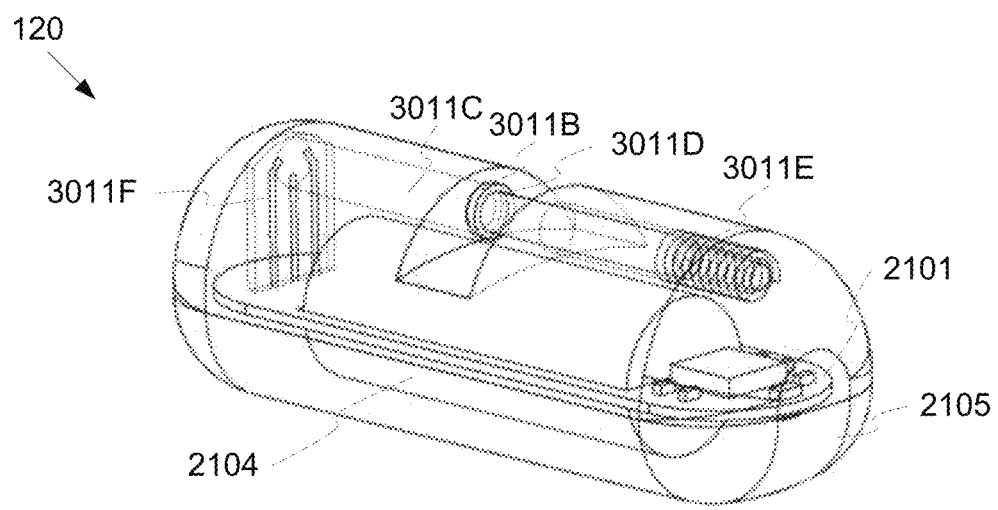

FIG. 20L shows a sensing device 120 for capturing a sample portion upon rotation of the device. The device 120 can have a magnetically effected member 2104 embedded in an encapsulation 2105 along with an optional electronics board 2101 and sensor board 3011F. The sensing device 120 can have a sample cavity 3011C which can normally be closed by the member 3011D using spring force from spring 3011E pressing 3011D toward the opening 3011B of the cavity 3011C. But when the sensing device 120 is exposed to a rotation force, then the centripetal force can force the member 3011D to overcome the spring force from spring 3011E and expose an opening to the cavity 3011C which can then fill with surrounding sample. When the rotation stops then the sample cavity 3011C can again be closed off by member 3011D. The collected sample in cavity 3011C may be released or mixed at a later point in time upon a second rotation of the sensing device 120 or the collected sample may be extracted for further analyses or use. The sensing device 120 can have an optional sensor board 3011F for doing a measurement on the captured sample.

Figure 20M:
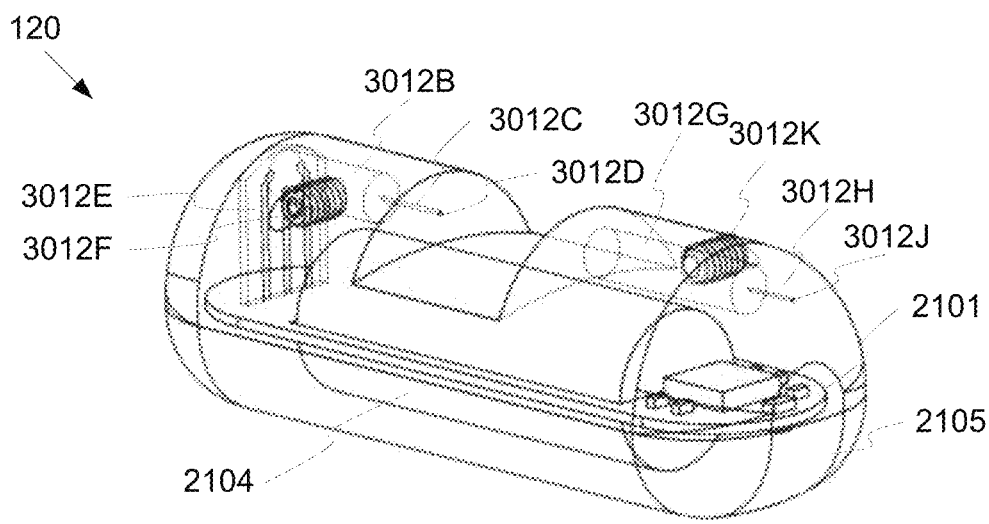

FIG. 20M shows a sensing device 120 for capturing a sample portion upon rotation of the sensing device 120 as well as releasing a liquid upon rotation of the sensing device 120. The sensing device 120 can have a magnetically effected member 2104 embedded in an encapsulation 2105 along with an optional electronics board 2101 and sensor board 3012E. The sensing device 120 can have a sample cavity 3012B which is open to a surrounding fluid via a capillary channel 3012C to an opening 3012D. If the pressure difference between the cavity 3012B and the surroundings is small, then no or minimal fluid can be transferred to the cavity 3012B. But upon the rotation of the sensing device 120 then the centripetal force can overcome the restriction to fluid movement and surrounding liquid can travel into chamber 3012B where it can optionally be analyzed with electronic board 3012E or it can be extracted later via port 3012F. The capillary channel 3012C can be coated to be more hydrophobic or hydrophilic to allow or block passage of fluid through channel 3012C as required by the application. The sensing device 120 can have a cavity 3012G that can hold a material to be released into the surroundings at a certain point. Under normal conditions the material in cavity 3012G can stay or mostly stay in the cavity, but when exposing the sensing device 120 to a rotating magnetically field then the material can travel through capillary 3012H to the outside opening 3012J. The capillary channel 3012H can be coated to be more hydrophobic or hydrophilic to allow or block passage of fluid through channel 3012H as required by the application. The cavity 3012G can be filled with the needed material via port 3012K. Only one or both cavities 3012B and 3012G can be present in a sensing device 120.

Figure 20N:
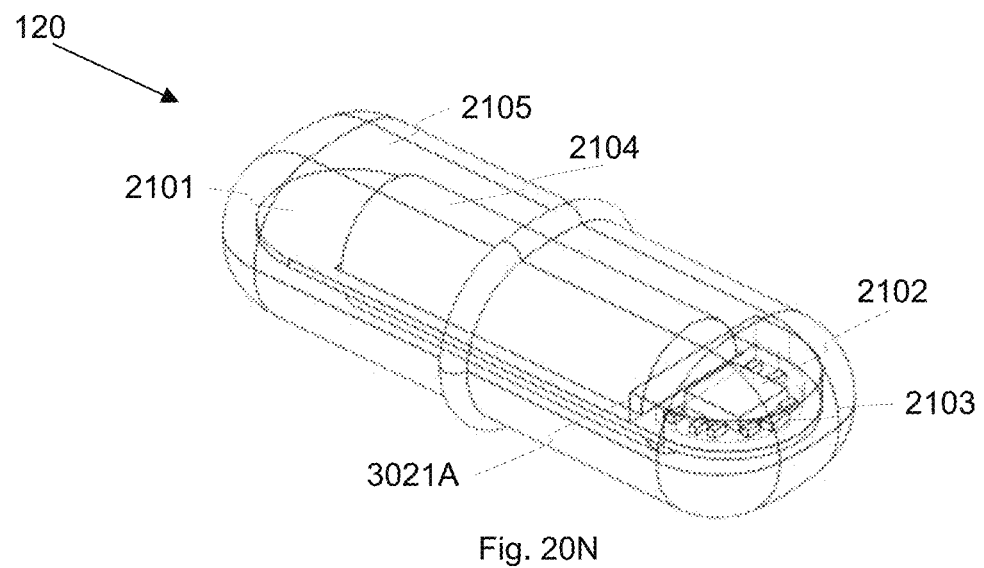

FIG. 20N shows a measurement device 120 with a hermetically sealed circuit. The hermetical sealing helps to expand the life of the device by preventing humidity to enter the circuit components 2102 and 2103 among others. The hermetical seal is generated by using a hermetical stable ceramic base material as the circuit board 2101 and a hermetical stable ceramic lid 3021A which is bonded to the circuit board 2101 with hermetical epoxy like Epoxy Technology EPO-TEK H74. This creates a cavity where the electronic components are located. Alternative to full hermetical seal is using near hermetical packaging technology like epoxy encapsulation.

Figure 21A:
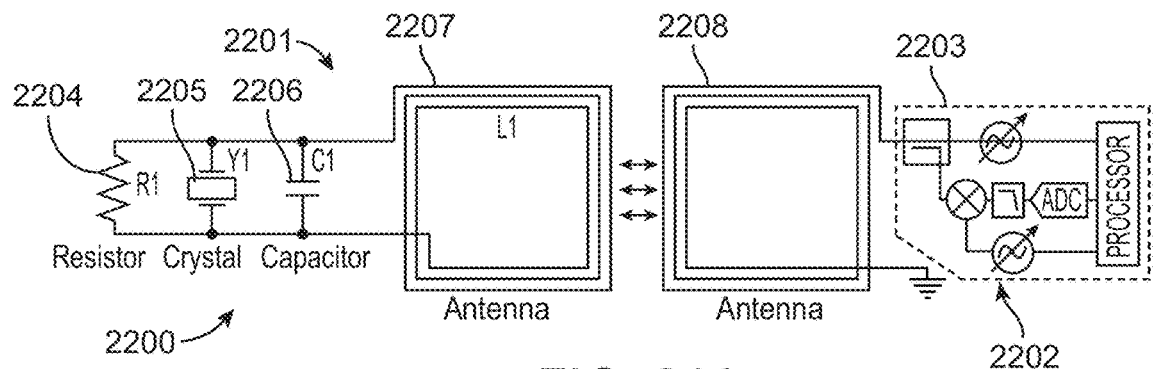
FIG. 21A illustrates a variation of a circuit for wireless temperature measurement.

FIG. 21A depicts a circuit 2200 for wireless temperature measurement. 2201 is the sensor circuit which comprises a temperature sensitive crystal 2205, an antenna 2207 which is in communication with a receiver circuit 2202 which can have an antenna 2208 and a network analyzer 2203 as schematically shown. The resistor component 2204 and the capacitor component 2206 may or may not be needed depending on the crystal 2205 and antenna 2207 characteristics. The temperature at crystal 2205 is measured by the receiving circuit 2202 which can have a network analyzer 2203 that is sensitive to changes in the field of the antenna 2208 and can therefore sense the resonance response of the crystal 2205 of the sensor circuit 2201. The receiver circuit 2202 can be implemented with more or less components as is intuitive to someone with skills in the art of spectrum analyzers and network analyzers. The advantage of the sensor circuit 2201 is that it is made up of passive components i.e. no semiconductor is involved which can otherwise reduce the temperature range as well as add cost and reliability issues. The crystal can be sensitive to other effects like acceleration whereby the rotation of the stir-bar can be measured or it can be sensitive to pressure, force, gyration or humidity.

Figure 21B:
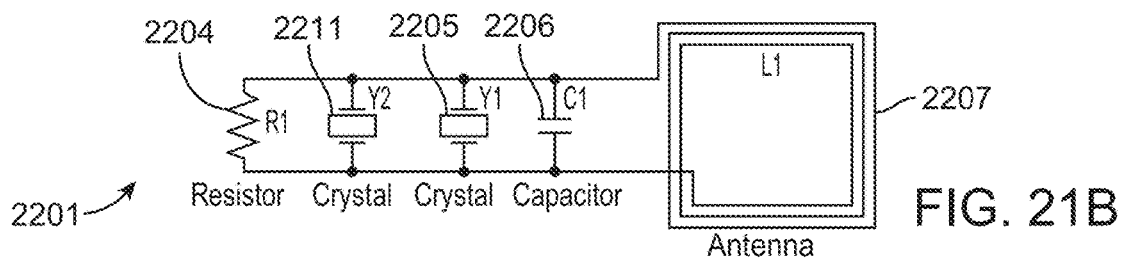
FIG. 21B illustrates a variation of a sensor circuit for the sensing device.

FIG. 21B depicts an alternative sensor circuit 2201 which can have an additional reference crystal 2211 which can have a lower sensitivity to temperature than the first crystal 2205. By having 2 crystals in the circuit 2201 then external effects that affects the characteristic resonance frequency of the first crystal 2205 like changes in excitation field or changes in capacitance or inductance due to proximity of the sensor circuit 2201 to external bodies or fluids can be measured and compensated for. For example, if the circuit 2201 is affected by external capacitive influence that changes the resonance frequency of first crystal 2205 as well as reference crystal 2211 by approximately equal amount then the difference between the resonance frequency of the first crystal 2205 and reference crystal 2211 can still be the same and this resonance frequency difference can be an indication of the temperature. An example of a temperature sensitive first crystal 2205 is Axtal GmbH & Co. KG RKTV206 which can have a frequency change of 48 ppm/° C. and 0.12 ppm/° C.$^2$, an example of reference crystal 2211 is Axtal GmbH & Co. KG RKOV206 which can have a frequency change of <0.07 ppm/C$^2$. More or less components can make up the circuit, active components can be added to enhance stability, sensitivity and/or signal strength. The first crystal 2205 or an additional crystal can be added with other sensing characteristics like acceleration for rotational speed detection, pressure, force, gyration or humidity.

Figure 21C:
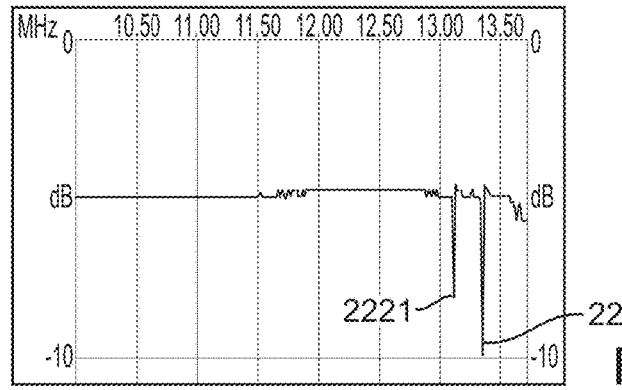
FIGS. 21C and 21E illustrate network analyzer scans of variations of the sensor circuit. (There is no FIG. 21D.)

FIG. 21C shows a network analyzer scan of a sensor circuit 2201 with a crystal with resonance at approximately 13.1 MHz 2221 and another crystal with resonance at approximately 13.36 MHz 2222. The resonances of both crystals can be detected.

Figure 21E:
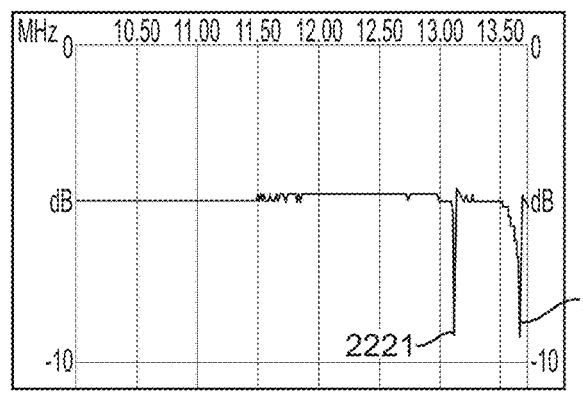

FIG. 21E shows a network analyzer scan of a sensor circuit 2201 with a crystal with resonance at approximately 13.1 MHz 2221 and another crystal with resonance at approximately 13.66 MHz 2231. The resonances of both crystals can be detected.

Figure 21F:
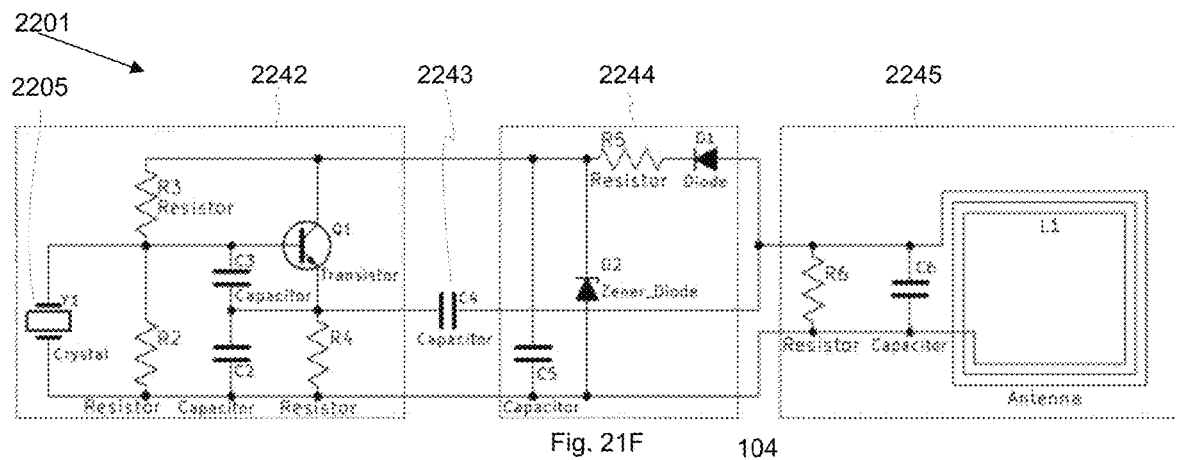

FIG. 21F shows an implementation of an active crystal oscillator circuit for wireless measuring temperature with a temperature sensitive crystal 2205. By using an active circuit i.e., a circuit that amplifies and/or buffers the crystal oscillation signal, the crystal frequency can be less affected by environmental changes and therefore the measurement of temperature can be more accurate. The circuit comprises a Colpitt crystal oscillator section 2242 that generates a frequency signal which gets coupled to the antenna section 2245 via a capacitor 2243. The coupling 2243 could be by a transformer or a capacitor and a resistor or depending on the antenna by a resistor. The circuit 2201 can have a power harvesting section 2244 for harvesting wireless power in the case where the circuit is powered by wireless energy. The power harvesting circuit can be more or less complex depending on efficiency requirements and signal variability. The circuit can be used for measuring parameters other than temperature such as pressure, force, rotation, acceleration, humidity or the like by using crystals that are sensitive to pressure, force, acceleration, gyration, humidity or the like. Many other possible implementations of active oscillation circuits 2242 exists and can be used as well as energy harvesting 2244 implementations and couplings 2243.

Figure 21G:
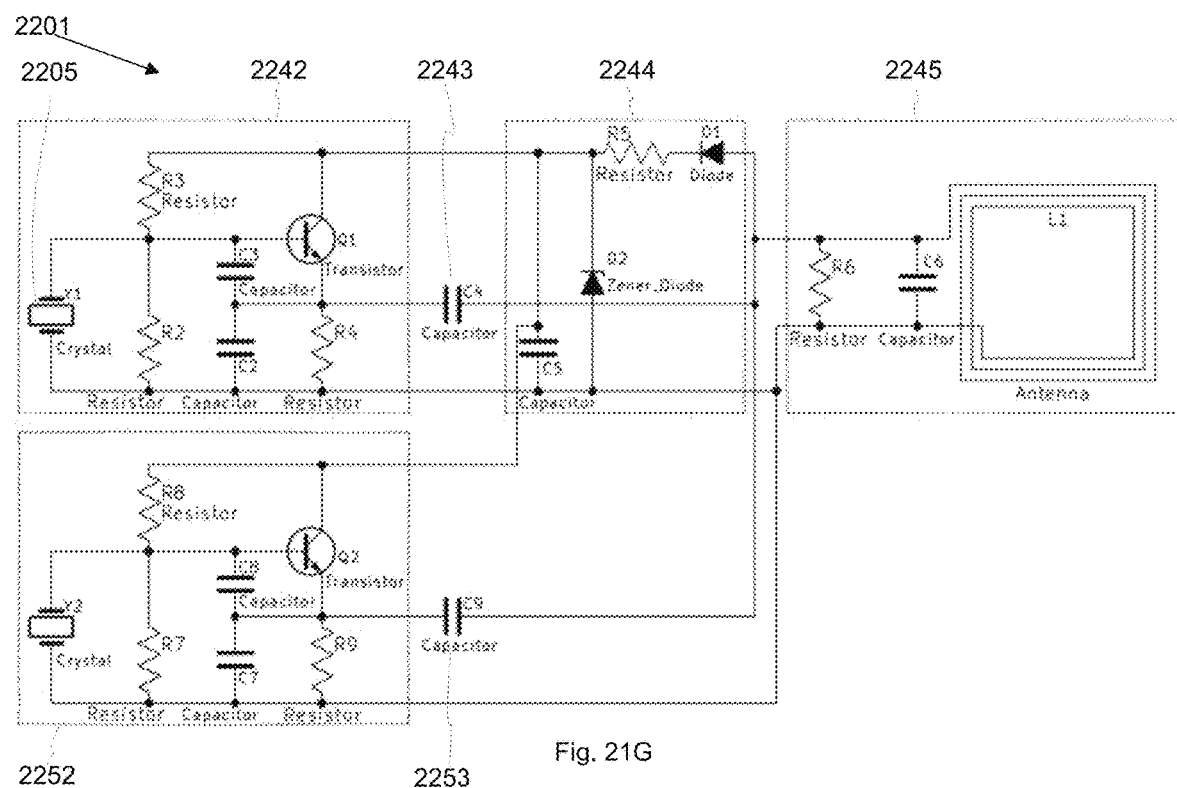

FIG. 21G shows an implementation of a circuit with dual active crystal oscillators for the case where there are one or more measuring crystals 2205 and and/or a reference crystal oscillator. The circuit comprises a Colpitt crystal oscillator section 2242 that generates a frequency signal which gets coupled to the antenna section 2245 via a capacitor 2243. The circuit can have a $2^{nd}$ crystal oscillator section 2252 that generates a frequency signal which gets coupled to the antenna section 2245 via a capacitor 2253. The circuit can have a power harvesting section 2244 for harvesting wireless power in the case where the circuit is powered by wireless energy. The circuit 2201 could be expanded with more oscillator sections as required by the application by adding more oscillator sections and couplings to the antenna. The circuit 2201 can be used in the case where a reference crystal and/or more measuring crystals are to be used for measuring parameters such as temperature, pressure, force, acceleration, gyration, humidity or any other measurement where a crystal can be made that can have a sensitivity to a particular parameter. This can be used in cases where redundant measurements are desired like dual temperature measurements. Many other possible implementations of active oscillation circuits 2242 and 2252 exists and can be used as well as energy harvesting 2244 implementations and couplings 2243 and 2253.

FIG. 21H shows another implementation of a temperature sensitive crystal oscillator for amplitude modulation. In this case a $1^{st}$ Crystal oscillator circuit 2262 is used to generate an oscillation that varies with temperature. This oscillation could be around 32 KHz. The signal from the $1^{st}$ Crystal oscillator is mixed 2264 with the signal from a $2^{nd}$ crystal oscillator 2263 that could be 13.56 MHz, this would generate an approximately 32 KHz Amplitude Modulated (AM) signal on a 13.56 MHz carrier frequency, where the 32 KHz can vary with changing temperature. This can be useful in the case where multiple signal sources are to be used within signal range of each other and identified by the receiver. The circuit 2201 can have an advantage in the case where a measuring crystal outputs too low of a frequency for a practical wireless transmission. The circuit can be used in the case where two crystal measurements are needed or where a reference crystal and a measurement crystal is needed. The circuit can be expanded with more Crystals feeding into the mixing stage or multiple mixing stages for more crystal frequencies. This can be used for other than temperature measuring crystals like for crystals that are sensitive to pressure, force, acceleration, gyration, humidity or other effects.

FIG. 21i shows a circuit for implementing an AM modulated signal with two crystals. The circuit comprises a Colpitt crystal oscillator section 2242 using $1^{st}$ crystal 2205 that is temperature sensitive for generating a frequency that is dependent on temperature. This signal is coupled via capacitor 2243 into the AM modulation section 2272 based on a $2^{nd}$ crystal where the signal of the $1^{st}$ crystal and the $2^{nd}$ crystal is mixed to generate an AM modulated output that is coupled via capacitor 2273 to the antenna section 2245. The circuit can have a wireless energy harvesting section 2244 for powering the circuit with wireless energy. This can be useful in the case where multiple signal sources are to be used within signal range of each other and identified by the receiver. The circuit 2201 can have an advantage in the case where a measuring crystal outputs too low of a frequency for a practical wireless transmission. The circuit can be used in the case where two crystal measurements are needed or where a reference crystal and a measurement crystal is needed. The circuit can be expanded with more Crystals sections 2242 feeding into the modulation section 2272. The circuit 2201 can be used for other than temperature measuring crystals like for crystals that are sensitive to pressure, force, acceleration, gyration, humidity or other effects. For circuits 21A to 21i one or more of the crystals can be replaced with a resonator like a combined inductor and capacitor where the capacitor or inductor is more or less sensitive to temperature or other parameters of interest.

Figure 22A:
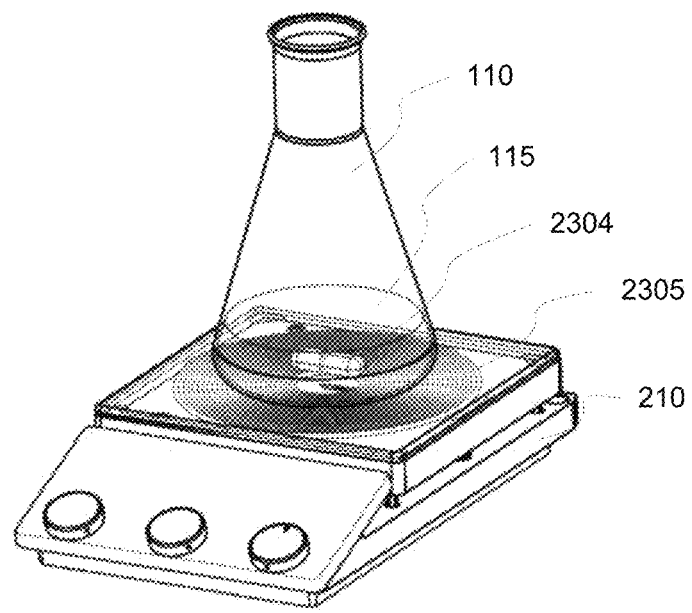
FIG. 22A illustrates a variation of a temperature measuring system.

FIG. 22A shows an instrument, such as a hot plate 210, for inductive heating of an inductively absorbing member 2304 inserted in a container 110, such as a flask, with a substance 115, such as a liquid, to be heated. By using inductive power from the coil 2305 the stir bar or sensing device 120 can have an inductively absorbing member 2304 that can absorb the energy and heat the liquid 115. The inductively absorbing member 2304 can be a stir bar with an iron core that can absorb the inductive energy, however it can be any material that absorbs inductive power in the frequency range of emitted energy from the coil 2305. The inductively absorbing member 2304 can be made from or with a material that can have a curie temperature point where the absorption of energy decreases when it has reached a certain temperature, thereby regulating the temperature of absorbing member 2304 and thereby the temperature of the liquid 115; such material can for example be magnetite with different Zn content to create a material with curie temperatures from 0 to 680° C. Almost any metal or ferrite can absorb inductive energy at certain frequencies and thereby be a candidate for the inductively absorbing member 2304. The inductively absorbing member 2304 can be combined with a wireless temperature sensing circuit and thereby create a system for electronic regulating the temperature of the liquid 115. The inductively absorbing member 2304 can be a magnetically effected material like iron or iron containing compound that can be moved or rotated by an external magnetic field and thereby create a mixing action in addition to heating by having a magnetic field generator embedded in instrument 210. The absorbing member can be coated or overmolded in a material that is inert to the liquid 115 that it will be exposed to.

Figure 22B:
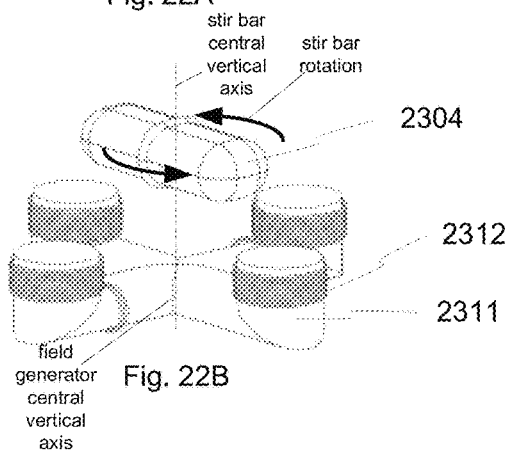
FIG. 22B illustrates a variation of a magnetic field generator and the sensing device positioned to be rotated by the magnetic field generator.

FIG. 22B shows an example of a magnetic field generator for rotating a magnetically effected member 2304 by changing the magnetic field. This magnetic field generator is suitable for implementing in instrument 210 proximal to coil 2305. This field generator comprises electro magnets that can change the orientation of the magnetic field on the 4 different poles by changing the current in coils 2312. The structure 2311 can be a ferromagnetic material that can have low absorbance at the frequency of the inductive coil 2305 thereby limiting the heat absorption in structure 2311.

Figure 22C:
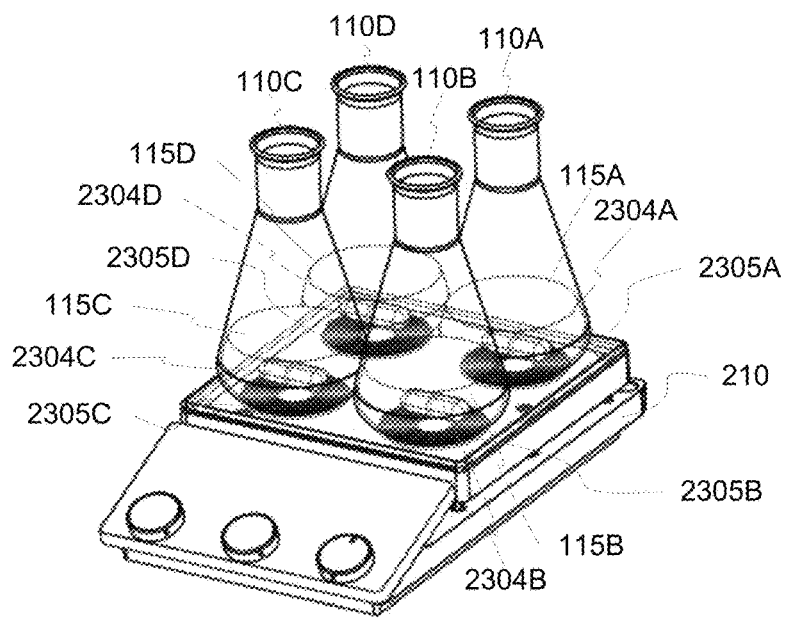
FIG. 22C illustrates a variation of a temperature measuring system.

FIG. 22C shows an instrument 210 for individual inductive heating of an inductively absorbing members 2304A-2304D inserted in flasks 110A-110D respectively with liquids 115A-115D to be heated to same or different temperatures. By using inductive power from the coils 2305A-2305D the inductively absorbing members 2304A-2304D can absorb the energy and heat the liquids 115A-115D. The inductively absorbing members 2304A-2304D can be combined with a wireless temperature sensing circuits and thereby create a system for electronic regulating individual temperatures of the liquids 115A-115D. The inductively absorbing members 2304A-2304D can be a magnetically effected material like iron or iron containing compound that can be moved or rotated by an external magnetic field and thereby create a mixing action in addition to heating by having magnetic field generators embedded in instrument 210.

Figure 23A:
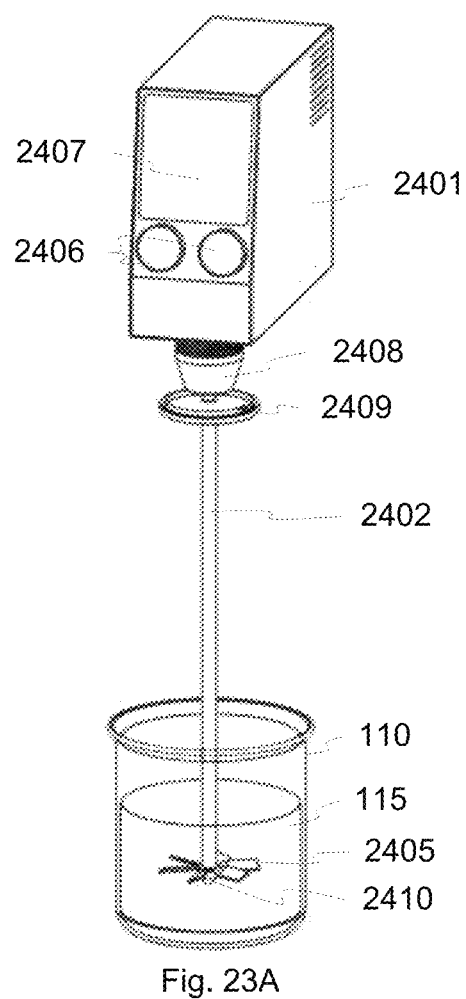
FIG. 23A illustrates a variation of a temperature measuring system.

FIG. 23A shows an overhead stirring instrument 2401 that can be connected to a mixing rod 2402 to mix a liquid 115 in a container 110 by rotating mixing blades 2405. The mixing rod 2402 contains a temperature sensor that can be located any place in the mixing rod structure, in FIG. 23A the sensor is in the lower most tip 2410 of the mixing rod 2402 such that the temperature sensor is proximal to the liquid 115. The temperature sensor is electrically connected to a wireless communication circuit 2409 for communicating the temperature wirelessly to an antenna in the instrument 2401. The sensing rod can contain other sensors instead of or in addition to the temperature sensor such as pH, sodium, ammonia, lithium, potassium, calcium, dissolved oxygen, $CO_2$, Specific gravity, refractive index, viscosity, salinity, conductance, color, absorbance, fluorescence, pressure, electrochemical, conductivity, chemiluminescence, liquid level, rotation, acceleration or velocity. The result of the measured property can be displayed on the screen 2407 or transmitted to other devices or electronic storage systems. Knobs 2406 are used to set functions of instrument 2401 such as rotation speed and other parameters. The liquid 115 can be heated by the process of mixing or agitating the liquid by the instrument 2401, such heating can be controlled using feedback from the temperature sensor. The temperature of the liquid 115 can be controlled by applying heating or cooling to the external surface of container 110.

Figure 23B:
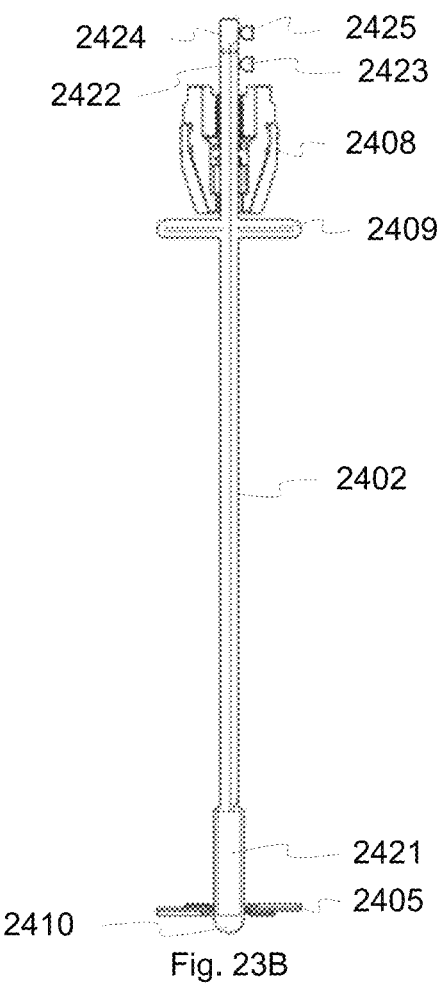
FIG. 23B is a variation of a cross-sectional view of the stirring system of FIG. 23A.

FIG. 23B shows a cut through of a mixing rod 2402 with a built-in electrical heating element 2421. The electrical heating element 2421 can heat the part or all of the mixing rod 2402 by use of electrical energy that is transmitted via electrical contact areas 2423 and 2425 to rotating electrical connecting elements 2422 and 2424. One of the electrical connections can happen through the mounting chug 2408, for example if that is made using electrically conductive materials. The mixing rod 2402 can contain a wireless circuit 2409 for wireless transmitting a temperature signal to a control unit. A temperature measurement from the mixing rod 2402 can be performed by direct electrical connections in the same manner that the heating element 2421 is connected via rotating connections.

Figure 24A:
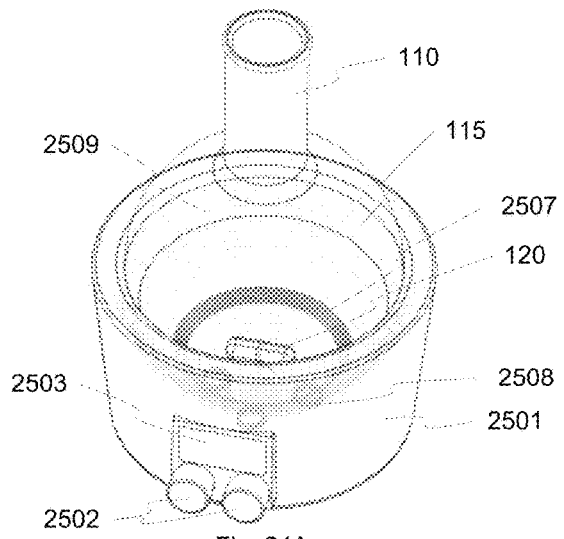
FIGS. 24A through 24C illustrate variations of temperature measuring systems.

FIG. 24A shows a heating device 2501 for a round bottom flask 110 with liquid 115. The heating device can have heating wire 2509 that is proximal to the round flask 110. The heating device 2501 can have controls 2502 for setting operation and a readout display 2503 for displaying parameters such as temperature of the liquid 115, rotational speed of the sensing device 120, desired temperature of the liquid 115, or combinations thereof. The heating device 2501 can have an antenna coil 2507 to communicate with a sensing device 120 with wireless temperature measurement. The heating device can further have a magnetic stirring function, for example controlled by coil 2508, for effecting a magnetically affected member in the sensing device 120 and thereby agitating the liquid 115. The sensing device 120 can measure other parameters instead of or in addition to temperature such as pH, sodium, ammonia, lithium, potassium, calcium, dissolved oxygen, $CO_2$, specific gravity, refractive index, viscosity, salinity, conductance, color, absorbance, fluorescence, pressure, electrochemical, conductivity, chemiluminescence, liquid level, rotation, acceleration or velocity. The magnetic stirring function can be implemented by use of electromagnets with varying activation patterns or by use of a motor with an attached permanent magnet.

Figure 24B:
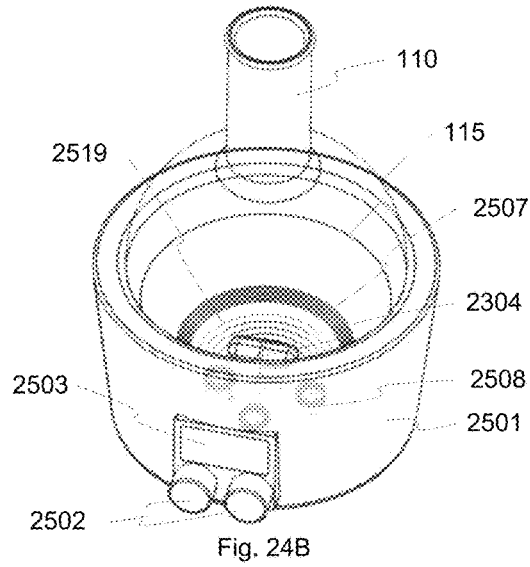

FIG. 24B shows another implementation of a heating device 2501 for a round bottom flask 110 with liquid 115. The heating device comprises induction heating coil 2519 that is proximal to the round flask 110 in which an inductively heated member 2304 is inserted and thereby can heat the liquid 115. The heating device 2501 can have a separate antenna coil 2507 to communicate with the inductively heated member 2304 for detecting temperature via a wireless temperature sensor implemented in inductively heated member 2304. The heating device can further have a magnetic stirring function 2508 for effecting a magnetically affected member in inductively heated member 2304 and thereby agitating the liquid 115. The inductively heated member 2304 can measure other parameters instead of or in addition to temperature such as pH, sodium, ammonia, lithium, potassium, calcium, dissolved oxygen, $CO_2$, specific gravity, refractive index, viscosity, salinity, conductance, color, absorbance, fluorescence, pressure, electrochemical, conductivity, chemiluminescence, liquid level, rotation, acceleration or velocity. The magnetic stirring function can be implemented by use of electromagnets with varying activation patterns or by use of a motor with an attached permanent magnet.

Figure 24C:
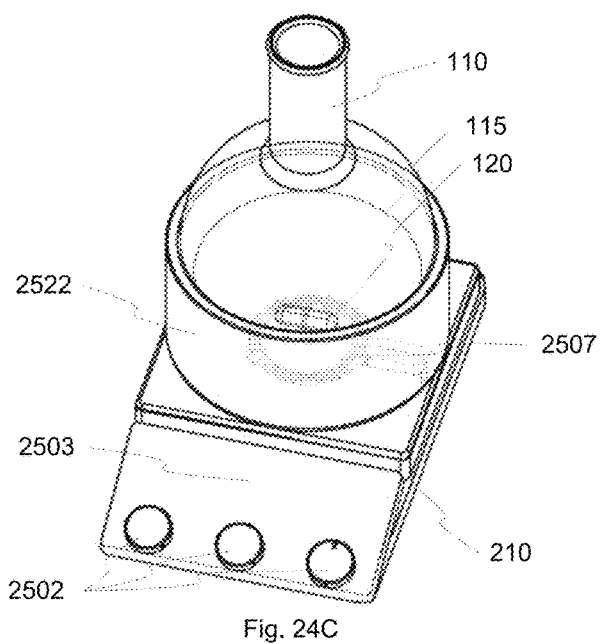

FIG. 24C shows an adapter 2522 for use with a round bottom flask 110 on a flat stirrer hotplate 210. The stirrer hotplate 210 can have the ability to communicate with sensing device 120 with a built-in circuit for wireless measuring temperature pH, sodium, ammonia, lithium, potassium, calcium, dissolved oxygen, $CO_2$, specific gravity, refractive index, viscosity, salinity, conductance, color, absorbance, fluorescence, pressure, electrochemical, conductivity, chemiluminescence, liquid level, rotation, acceleration and/or velocity. The adapter 2522 can be made from a material that is able to conduct heat without blocking the wireless communication between the antenna 2507 in the hotplate 210 and the sensing device 120. The adapter 2522 can for example be made from ceramic materials or glass materials. An example of a good material is Aluminum Nitrade (AlN) which has a high thermal conductivity.

Figure 25A:
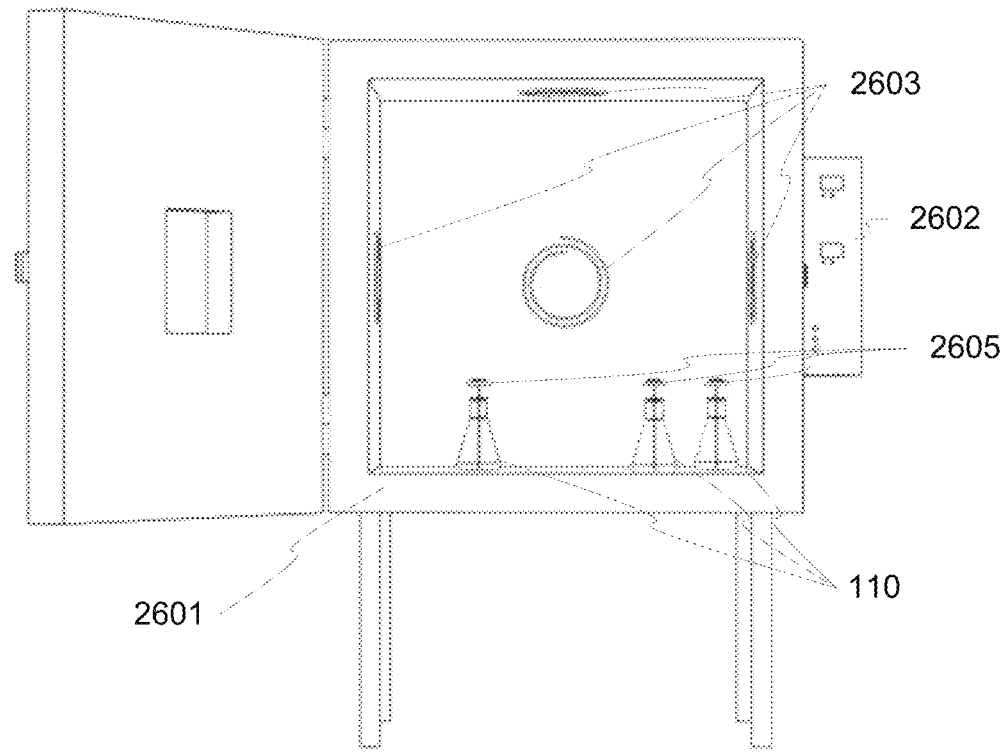
FIG. 25A illustrates a variation of a temperature measuring system having a chamber with a door in an open configuration.

FIG. 25A shows a chamber 2601, such as an oven, autoclave, refrigerator, or freezer, with wireless temperature sensors 2605 located in different positions within the chamber. The chamber 2601 can have walls and a door. The walls and/or door of the chamber can be made from metal and have insulation, for example styrofoam, plastic, water, or combinations thereof. The walls and/or door can be substantially resistive or impenetrable to the transmission of RF communication signals. The temperature sensors 2605 can have probes measuring temperature in flasks 110, but they could as well be measuring the chamber 2601 environment at a particular location with no flasks 110. The chamber 2601 can have antennas 2603 located at various positions in the chamber, in this example there are 3 antennas 2603 located on 3 different sides of the inside of the chamber 2601 and a $4^{th}$ antenna 2603 at the inside of the ceiling of the chamber 2601. The phase difference of the wireless signal received by the different antennas 2603 is used to determine the location of the temperature sensors 2605 by knowing the location of the antennas 2603 and by measuring the difference in phases of the wireless signals received by the different antennas 2603 and thereby knowing the distance difference from each antenna 2603 to a particular wireless temperature sensor 2605 then the location of the particular wireless temperature sensor 2605 can be determined by known triangulation formulas. When the location of more than one wireless temperature sensor 2605 is to be determined then it is necessary that the wireless signal measured by the antennas 2603 is measured from only one of the wireless temperature sensor 2605 at a time, this can be accomplished in the following ways; if the wireless temperature sensors 2605 are using RFID for communication then the communication protocol allows for only one wireless temperature sensor 2605 to communicate at a time, for example if the wireless temperature sensor 2605 is based on a Texas Instrument RF430FRL153 RFID measurement IC it is using RFID protocol ISO 15693 which can have a "Stay Quiet" command that can be sent to all but the wireless temperature sensor 2605 that is to be measured. If the wireless temperature sensors 2605 are using different frequencies to transmit signal, then the frequency for a specific wireless temperature sensor 2605 can be selectively filtered out and measured. If the temperature sensors 2605 are made to activate when a specific frequency is transmitted, then the specific frequency to activate a temperature sensor can be transmitted by one of the antennas 2603 or by an additional antenna (not shown) whereupon the particular wireless temperature sensor starts to transmit. In order for the location to be determined the frequency of the transmitted signal from the wireless temperature sensors 2605 can fall in a range where they can be distinguished by their phase differences i.e. the wavelength of the wireless signal can be larger than the area whereupon the wireless temperature sensors 2605 can be located. Due to electronic noise issues it is an advantage if the wavelength is not 3 to 4 orders of magnitude larger than the distance resolution, otherwise it can be difficult to determine very small phase differences. The wavelength of a wireless signal is approximately equal to the speed of light (300,000,000 m/s) divided by the frequency of the wireless signal. The 13.56 MHz frequency of ISO 15693 with side bands of up to 484 KHz gives a wavelength of approximately 22 meters (72 ft) which is good for measurement in large chambers. Bluetooth frequency is in the range of 2.4 GHz which has a wavelength of only 0.12 m (0.4 ft) which could work for very small chambers. The antennas 2603 are shown as coil antennas, but other antenna types can be envisioned. The determination of location of wireless sensors can be done in open space or in a room rather than in a chamber 2601. The wireless temperature sensors 2605 can be battery powered by a one-time use battery or by a rechargeable battery where the charging happens by wireless charging or by plug-in wired charging, the wireless temperature sensors 2605 could be self-powered by use of RFID or other wireless powered scheme. The wireless temperature sensors 2605 could measure other properties instead of- or in addition to temperature such as pH, sodium, ammonia, lithium, potassium, calcium, dissolved oxygen, $CO_2$, specific gravity, refractive index, viscosity, salinity, conductance, color, absorbance, fluorescence, pressure, electrochemical, conductivity, chemiluminescence, liquid level, rotation, acceleration or velocity. The system could use more or less antennas 2603 depending on how many dimensions are to be determined and if additional accuracy is desired by having more measurement points. The chamber 2601 can have a control unit 2602 for control of the chamber and for readout of measurements.

Figure 25B:
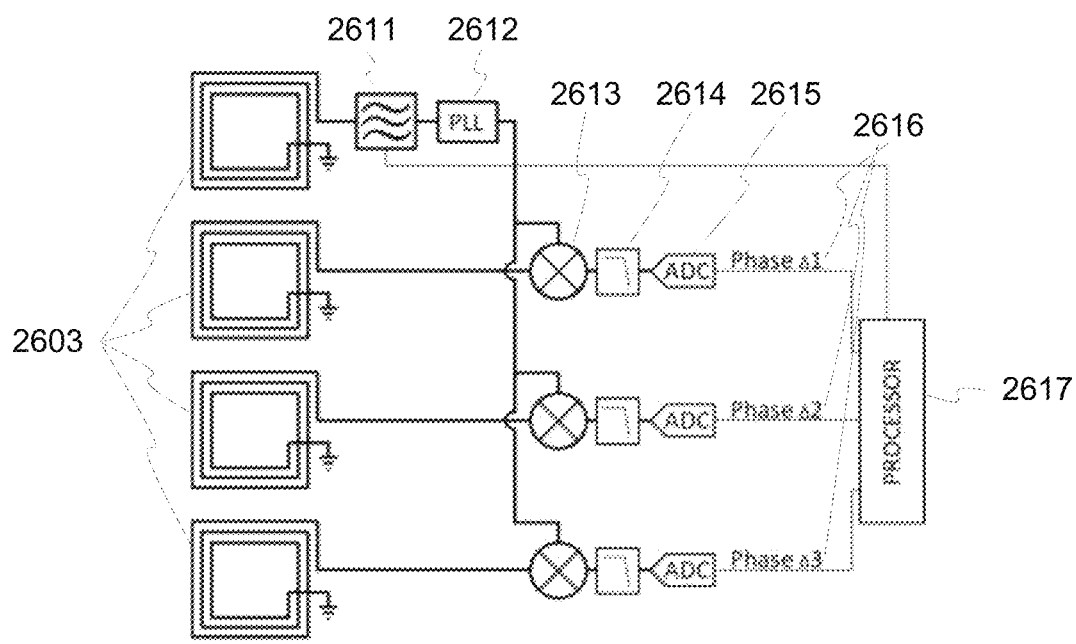
FIG. 25B illustrates a variation of a circuit for determining locations of wireless sensor sources.

FIG. 25B shows a circuit for the determination of phase differences from a wireless sensor signal from various antennas 2603 to determine locations of a wireless sensor source. The circuit is simplified and does not show amplifiers and other components typically required for signal fidelity in a real system. The signal from one of the antennas 2603 is passed through a bandpass filter 2611 to a Phase Lock Loop unit 2612 for cleaning or stabilizing the received signal. The signal is then sent to be mixed with the received signal from other antennas 2603 using a mixer 2613 for each additional antenna 2603 and a filter 2614 and an Analog to Digital Converter 2615 whereafter the phase difference from the first antenna 2603 to the other antennas 2603 can be represented as a digital value to be processed by a microcontroller 2617. More or fewer antennas 2603, mixers 2613, filters 2614, Analog to Digital Converters 2615 depending on the amount of distance dimensions that are needed to determine location or to increase accuracy of measurements. If the wireless system is an RFID system, then the antennas may be driven by a source signal and the measured signals are picked up from the antennas using splitters (not shown).

Figure 26:
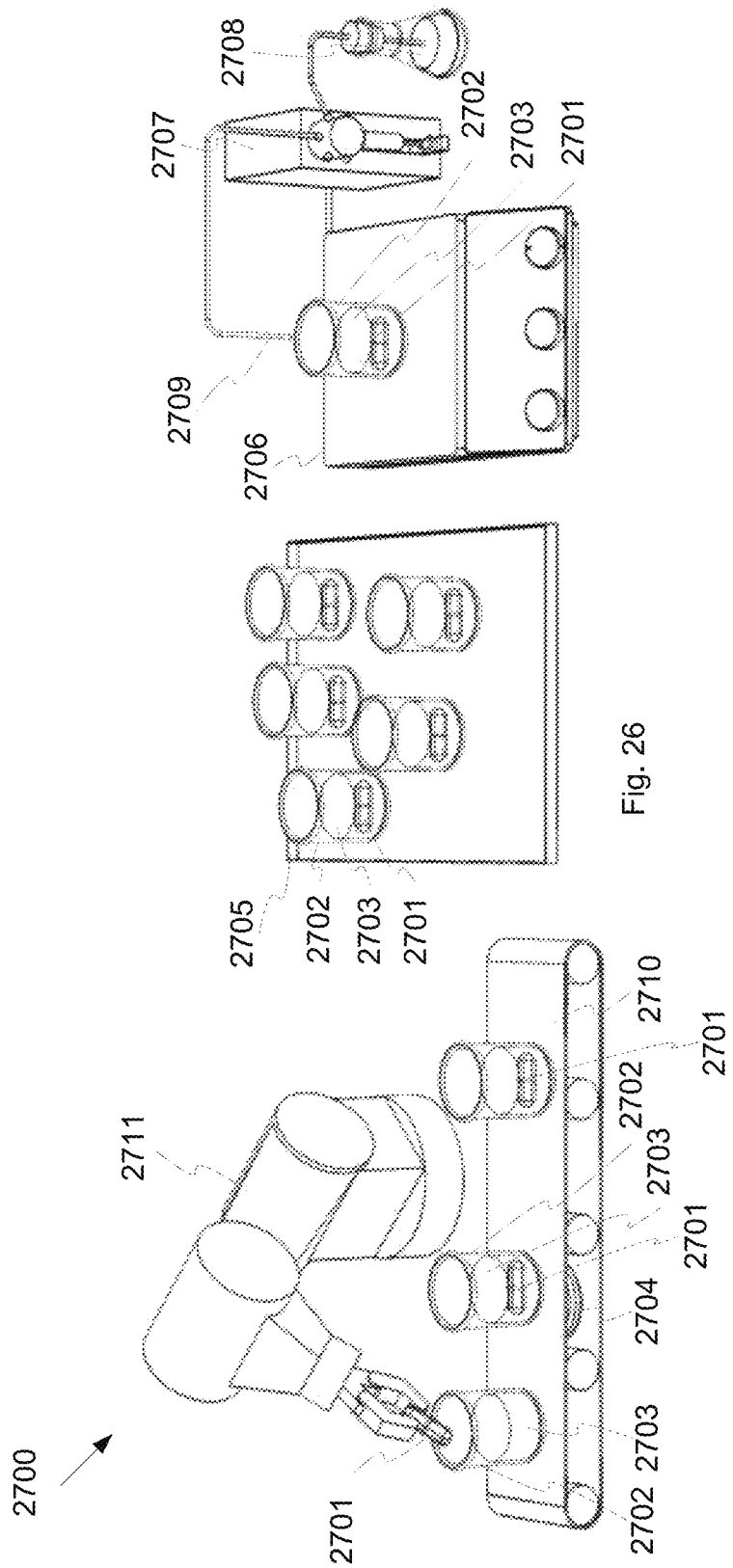
FIG. 26 illustrates a variation of a sample processing and tracking system.

FIG. 26 illustrates a sample tracking system 2700 for tracking samples and vials by use of a wireless tracking device 2701, which contains a unique digital ID which can be tracked throughout the workflow of a sample from initial loading of liquids, such as sample 2703, and insertion of wireless tracking device 2701 into sample 2703 in containers 2702, possibly by an automated mechanism, such as a robotic arm 2711. The wireless tracking device 2701 can be loaded manually. Samples can be read by reading station 2704 to identify and pair sample 2703 with wireless tracking device 2701 ID. The samples 2703 can be presented to reader 2704 manually or by automated machinery 2710. Samples 2703 can be stored at a storage location 2705 with their wireless tracking devices 2701 identifying each sample. Samples 2703 can be processed at one or more processing stations 2706 where the wireless tracking device 2701 can be read by the station 2706 before and after processing the sample 2703. The processing station 2706 can be a hotplate stirrer with built in wireless reader. The processing station 2706 can additionally function as a dispensing station where another liquid 2708 is dispensed 2709 with a pump 2707 into the sample 2703 in the vial 2702. The wireless tracking device 2701 can possibly contain non-volatile memory that can be written by wireless means and thereby inscribed with specific station location ID's or process parameters or measurement values to function as a log of process and measurement values which can be written and read at various points throughout the process and afterwards. The wireless tracking device 2701 can function as a stir bar and contain a magnetically effected member which can move or rotate in response to a magnetic field. The wireless tracking device 2701 can function as a wireless sensor that can measure one or more parameters like temperature, pH, sodium, ammonia, lithium, potassium, calcium, dissolved oxygen, $CO_2$, specific gravity, refractive index, viscosity, salinity, conductance, color, absorbance, fluorescence, pressure, electrochemical, conductivity, chemiluminescence, liquid level, rotation, acceleration, velocity or location. The wireless tracking device can be powered by a one-time use battery or a rechargeable battery or it can have no battery and be powered by wireless energy like for example a RFID system. The wireless tracking device 2701 can be tracked by various stations automatically or manually and the information can be uploaded to a laboratory information system database. The wireless tracking device 2701 can be part of the container 2702.

Figure 27:
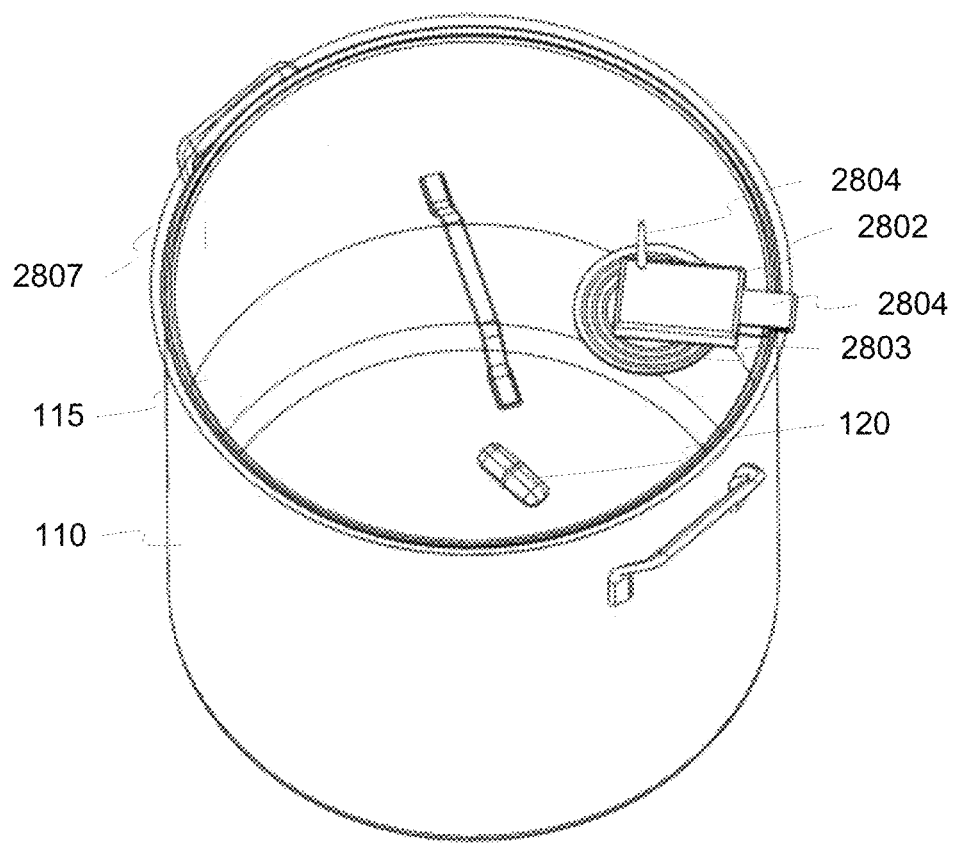
FIG. 27 illustrates a variation of a temperature measuring system.

FIG. 27 shows a container 110 with a liquid 115 and a lid 2807. In the container is a wireless sensing device 120. The container is equipped with a wireless communication device 2802 that can communicate with the wireless sensing device 120 via an antenna 2803 inside the container 110 and communicate wirelessly with an antenna 2804 outside of the container 110 to an external communication device like a smart phone. The wireless communication device 2802 can contain a battery inside the device 2802 for powering the wireless communication functions. The wireless communication device 2802 can be part of the container 110 or part of the lid 2807 of the container or it can be a separate device that is clipped onto the lid 2807 or onto the container 110.

The wireless communication device 2802 can for example communicate using 13.56 MHz RFID to a wireless sensing device 120 inside the container 110 and then communicate using 2.4 Ghz Bluetooth to a smart phone outside the container 110. Other communication protocols can be used the communication protocols can be the same or different for internal and external communication. The wireless communication device 2802 can be powered by a one-time use battery or by a rechargeable battery which is recharged by wired or by wireless power source or the wireless communication device 2802 can be powered from wireless energy without having a battery. The wireless sensing device 120 can be an ID device which only function is to identify itself or the liquid 115 or it can be a measuring device that can measure one or more of temperature, pH, sodium, ammonia, lithium, potassium, calcium, dissolved oxygen, $CO_2$, specific gravity, refractive index, viscosity, salinity, conductance, color, absorbance, fluorescence, pressure, electrochemical, conductivity, chemiluminescence, liquid level, rotation, acceleration, velocity or location. The wireless sensing device 120 can be wireless powered or it can contain a battery which is one-time use or rechargeable by use of wireless charging.

Figure 28A:
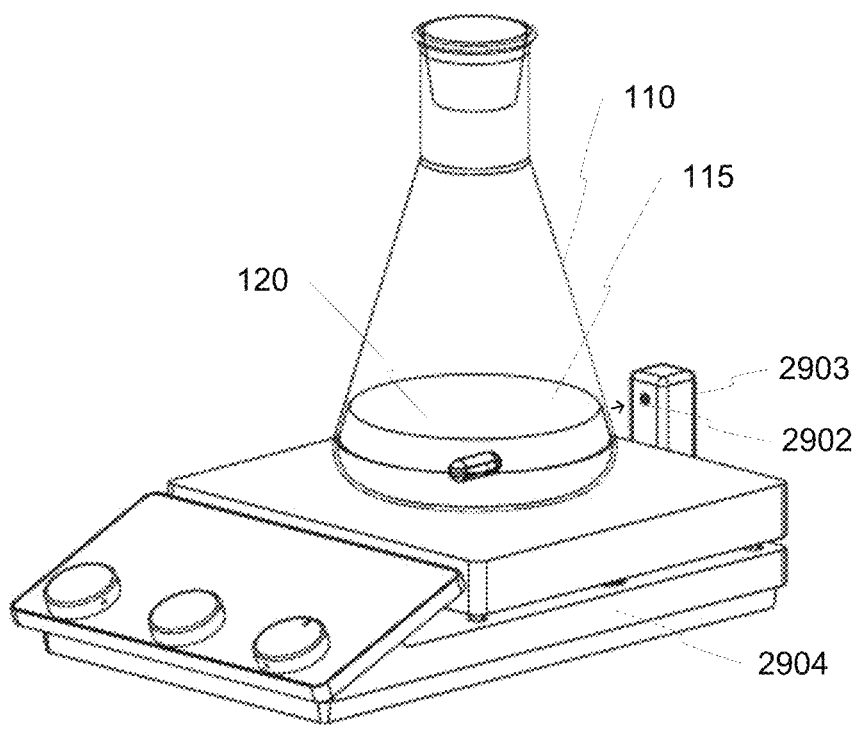
FIGS. 28A and 28B illustrate variations of a temperature measurement system.

FIG. 28A shows a heating device 2904 with an Infrared (IR) sensor system 2903. The IR sensor system 2903 measures the temperature of the outside of the container 110 with an IR sensing element 2902. The measurement can be used to control the temperature of the container 110 or to report the temperature. The IR sensor element 2902 can be a Melexis MLX90614ESF-BCF-000-TU. The IR sensor system 2903 can be part of the heating device 2904 or it can be added to the heating device 2904 and connected via USB or other connection. The IR sensor system 2903 can be used as an upgrade to less sophisticated hotplates 2904 by emulating an external thermal probe or by controlling supply power to the hotplate 2904. The IR sensor system 2903 may have readout display and knobs or adjustments for setting temperature and/or the IR sensor system 2903 may have connectivity to a computer or a smart-phone or other device for reading and setting temperature or operating parameters.

Figure 28B:
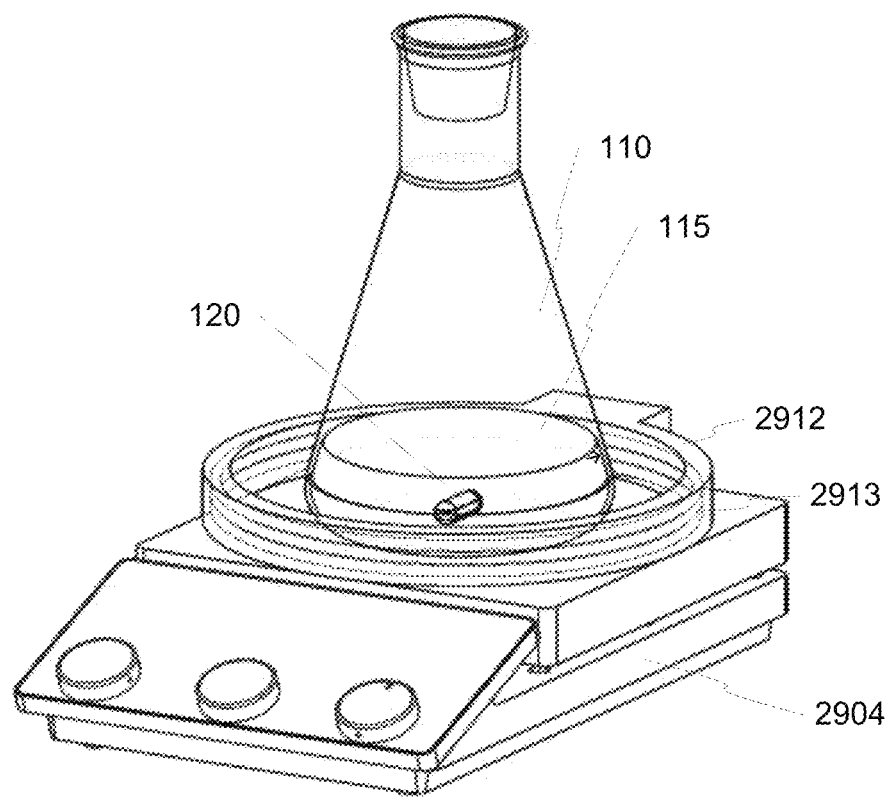

FIG. 28B shows a heating device 2904 with a wireless sensing device 120 and a wireless reading system 2912 attached to the instrument 2904 for communicating with the wireless sensing device 120. The wireless sensing device 120 measures the temperature of the liquid 115 in the container 110 which can be used to control the temperature output on the heating device 2904 and thereby the liquid 115 temperature. The wireless reader 2912 comprises a reading circuit and an antenna 2913. The wireless reader system 2912 can be part of the heating device 2904 or it can be added to the heating device 2904 and connected via USB or other connection. The wireless reader system 2912 can be used as an upgrade to less sophisticated heating devices 2904 by emulating an external thermal probe or by controlling supply power to the heating device 2904. The wireless reading system 2912 may have knobs or adjustments for setting temperature and/or the wireless sensor system 2912 may have connectivity to a computer or a smart-phone or other device for reading and controlling temperature or operating parameters. The wireless reading system may be a RFID system for powering and communication with a wireless temperature sensing device 120. The wireless reading system 2912 can be not in contact with a heating surface of the heating device 2904 nor the container 110 or the wireless reading system 2912 can be in contact with both the heating surface of 2904 and the container 110 where the wireless reading system 2912 can transfer heat from the heating surface of 2904 to the container 110, for example it can be an adapter that works to transfer hear from a flat heating surface of 2904 to a round bottom container 110. The wireless reading system 2912 can be contact either the heating surface of 2904 or the container 110.

The wireless sensing device 120 can be calibrated such that its reported temperature values are accurate. The calibration data can include how much the sensed temperature needed to be changed during calibration to be accurate, the dates and times of the respective calibrations, a serial number identification for the stir bar, the equipment used for the calibration, notes manually entered by the calibration personnel before, during or after each calibration, or combinations thereof. The calibration data can be stored in memory on the wireless sensing device 120 and/or in memory in a wireless receiver 210 and/or in memory on a server in data communication with the wireless receiver 210. Other parameters that are measured by the wireless sensing device 120 can be calibrated such as pH or how an acceleration value from an accelerometer corresponds to rotation velocity, any of the sensed parameters can be calibrated. The calibration information can be stored in memory on the wireless sensing device 120.

Memory in the wireless sensing device 120 for holding calibration information and identification information can be permanent memory such as Flash ROM or EEPROM or it can be Write Once ROM. Write Once ROM such as Sidense 1T-Fuse™ or Synopsis OTP NVM can tolerate high temperature which the wireless sensing device 120 may be exposed to during use. Random Access Memory can be used for storing calibration data as long as the device is powered by external wireless power or by a battery. Static Random Access Memory can tolerate high temperature which the wireless sensing device 120 may be exposed to during use.

The wireless sensing device 120 and/or wireless receiver 210 and/or server, for example with the calibration data in memory, can issue a notification that the calibration of the wireless sensing device 120 has expired, the wireless sensing device 120 is out of calibration, or combinations thereof, and can block users from operating the wireless sensing device 120 until the wireless sensing device 120 is recalibrated for temperature or other parameters.

The wireless sensing device 120 can be calibrated with a temperature reference tool, such as a temperature probe, that can be plugged in the back of a wireless receiver 210 on which the wireless sensing device 120 is being used. The reference tool can be immersed in the substance in which the wireless sensing device 120 is immersed. The reference tool can sense the temperature of the substance 115, communicate with the wireless sensing device 120, and reset/calibrate the temperature output of the wireless sensing device 120 to the correct temperature. The reference tool can enter an entry in the calibration data log for the wireless sensing device 120.

Reference profiles can be set and saved into the calibration data log for the wireless sensing device 120. The wireless receiver 210 can be used to calibrate the stir bar (with the assumption that the wireless sensing device 120 reaches the temperature of the wireless receiver 210 when the temperature of the wireless sensing device 120 stabilizes).

The wireless sensing device 120 can be calibrated by a process to be NIST certified.

Each wireless sensing device 120 can have an RFID tag. Each RFID tag can have a unique (e.g., serialized) tag ID number, for example, to uniquely identify and track each wireless sensing device 120.

The wireless sensing device 120 can be heated directly with induction heating energy from the wireless receiver 210. The inductive receiver in the wireless sensing device 120 can heat the substance 115 (e.g., with or without a separate conductive heating element in the wireless receiver 210). A first frequency can excite the inductive heating element and a second RF frequency can be in data communication with the wireless sensing device 120 (e.g., to detect temperature readings from the wireless sensing device 120).

The wireless sensing device 120 can have an on-board direct propulsion system. For example, the wireless sensing device 120 can have propellers at one or both ends of the wireless sensing device 120. The propellers can be oriented to direct thrust at a perpendicular direction to the longitudinal axis of the wireless sensing device 120. For example, the propellers can be powered by a battery in the wireless sensing device 120 and/or inductive power delivered to the wireless sensing device 120 from the wireless receiver 210. Thrust emitted by the propellers can propel the wireless sensing device 120 to spin about a central longitudinal axis of the wireless sensing device 120.

The wireless sensing device 120 can be in data communication (e.g., via Bluetooth) to the wireless receiver 210 and/or directly to an external antenna not in the primary wireless receiver 210, such as an antenna on a mobile device (e.g., tablet, smart phone) and/or server.

The wireless sensing device 120 can have a chemical (e.g., alkaline, aluminum-ion, vanadium redox, zinc-bromine, lead-acid, lithium, lithium-ion, lithium cobalt oxide, lithium ion manganese oxide, magnesium-ion) battery. The wireless sensing device 120 can have a disposable or rechargeable battery.

The wireless sensing device 120 can have a location tracking system on board and/or the location of the wireless sensing device 120 can be determined by triangulation by surrounding equipment (e.g., by three nearby wireless receiver 210 determining signal strength from the wireless sensing device 120). The location of the wireless sensing device 120 can be matched to that of respective wireless receiver 210 or other heating/cooling devices to determine at which heating/cooling station the wireless sensing device 120 is located. A wireless sensing device 120 can be wirelessly sent a request to identify itself, to which the wireless sensing device 120 can respond by illuminating an on-board LED, vibrating from an on-board motor, activating an on-board propeller, emitting a sound from an on-board speaker, or combinations thereof.

The wireless sensing device 120 can have on or more on-board chambers for storing samples or reagents and/or combining samples and/or reagents. The chambers can be moved longitudinally along the length of the wireless sensing device 120, for example to increase or decrease the centripetal acceleration exerted onto the chamber during the spinning of the wireless sensing device 120 (e.g., to increase or decrease centrifuging separation).

The wireless sensing device 120 can control/manipulate external elements (e.g., the wireless receiver 210 heater and rotating magnet, a titration pump, other energy sources (e.g., UV lamp)).

The wireless sensing device 120 can automatically communicate via internet (e.g., to phone/tablet/computer) for:
 a. Shipping more wireless sensing devices 120 when wireless sensing devices 120 are expired
 b. Accumulate quality monitoring data
 c. To notify when the wireless sensing device 120 is no longer within an acceptable calibration range
 d. To notify when the temperature of multiple on-board sensors starts to deviate
 e. For remote access of the wireless receiver 210
  i. Different settings—remotely changing parameters or monitoring or none
 f. Remote monitoring of temperature/spinning/other parameters
 g. Notify when something goes wrong/loses communication/power goes out
 h. User changes settings
 i. Software updates
 j. wireless sensing devices 120 can communication with one another
 k. External temperature probe is unplugged The wireless receiver 210 can have a wifi antenna or dongle that can communicate with a smart phone or other wifi device, for example to transmit the data from the wireless receiver 210 and wireless sensing device 120.

The wireless sensing device 120 could for example be made to be compatible for only stirring system (and otherwise not have heating capabilities) or only heating system (and otherwise not have stirring capabilities).

The wireless sensing device 120 can heat the substance 115 in which the wireless sensing device 120 is submerged by frictionally heating the substance 115 by spinning fast enough.

Retrofit old hot plates by adding a wireless relay box for plugging in "dumb" hot plate to turn in it on/off to get to the right temperature in response to the temperature reporting from a wireless sensing device 120.

Data logging of temperature and other measured parameters from a wireless sensing device 120 and connect the readings to LIMS (laboratory information systems)/storage database to send receive data, interface with other wireless sensing devices 120 and send/receive instructions Antenna in stir bar communicates with antenna in hot plate using RFID The wireless sensing device 120 can have onboard recharging system by use of an outside magnet, as coil in spinning wireless sensing device 120 is receiving inductive charge from a changing magnetic field.

The container 110 lid can have a rechargeable battery pack with antenna/inductive coils, for example that can have a rotating magnet and processor for rotating wireless sensing device 120 and reading parameters from the wireless sensing device 120. The container lid can be portable system for field use.

The wireless sensing device 120 can have adjustable density/ballast and density sensor by use of
 a. Onboard compressed (inert) gas vessel with controllably releasable
 b. Releasable ballast weights The wireless sensing device 120 as described herein can be used for numerous other applications. For example, a sensing device 120 can be used by a beer maker to remotely monitor the specific gravity or refractive index of the beer. When the specific gravity or refractive index reaches a specified quantity, an alert can be generated to notify the beer maker. As another example, a sensing device 120 can be used by an employee of a hospital or laboratory to verify whether sterilized or autoclaved substances reached a desired sterilization temperature. The sensing device 120 can monitor the temperature of the substances as they are autoclaved and notify the employee whether the temperature inside the substance reached the sterilization temperature. In yet another example, a chef can monitor properties of food in a closed container using a sensing device 120 to determine precisely when the food reaches a desired temperature, viscosity, specific gravity, or combinations thereof. In another example a chemical reaction with multiple steps can be processed by using the sensing device 120 as a temperature sensor and as an agitator in the reaction compound where an instrument is programmed to expose the chemical compound to different temperature steps and agitation velocities for different periods of time and using the feedback from the sensing device 120 to set correct temperature in the various steps. In another example an industrial processing station can monitor the conductivity of a cleaning fluid and replace it if the conductivity gets above a specific value.

Figure 29A:
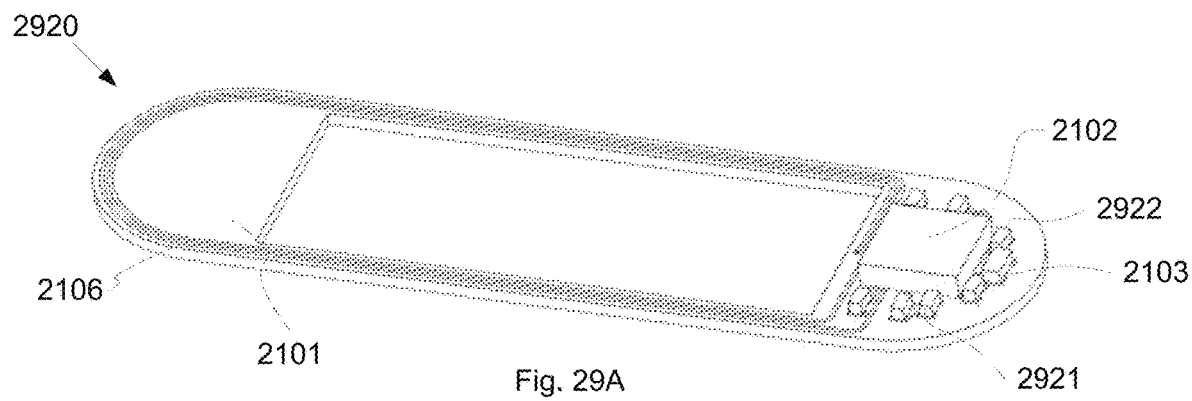
FIG. 29A through 29C illustrates a variation of a circuit board for wireless temperature sensing where the antenna is embedded in the circuit board.

FIG. 29A illustrates a circuit board assembly 2920 for use in a sensing device 120 such as a stir bar. An internal coil 2106 in the circuit board 2101, can form an on-board antenna for the sensing device 120. The antenna coil 2106 can be constructed as a conductive foil trace for example as a 166 um wide copper trace on the circuit board 2101. The antenna coil 2106 can be constructed by printing conductive traces on the circuit board 2101. The circuit board 2101 can be common glass fiber embedded epoxy circuit board material, example of such is FR4. The circuit board 2101 can be made of polyimide. The circuit board 2101 can be a ceramic substrate. The circuit board 2101 can be aluminum substrate with electrical isolated surfaces, an example of this is Henkel TCLAD (formerly Bergquist). The antenna coil 2106 can be a loop on the circuit board 2101, for example the trace can follow close to the outer edge of the circuit board 2101. The antenna coil 2106 can be a spiral on the circuit board 2101, for example the spiral trace can follow close to the outer edge of the circuit board 2101. The antenna coil 2106 can be formed on one or on multiple layers on the circuit board 2101, for example, the antenna coil 2106 can be approximately 2 windings on each layer of a 4-layer circuit board 2101 to provide a total of 8 windings.

Figure 29B:
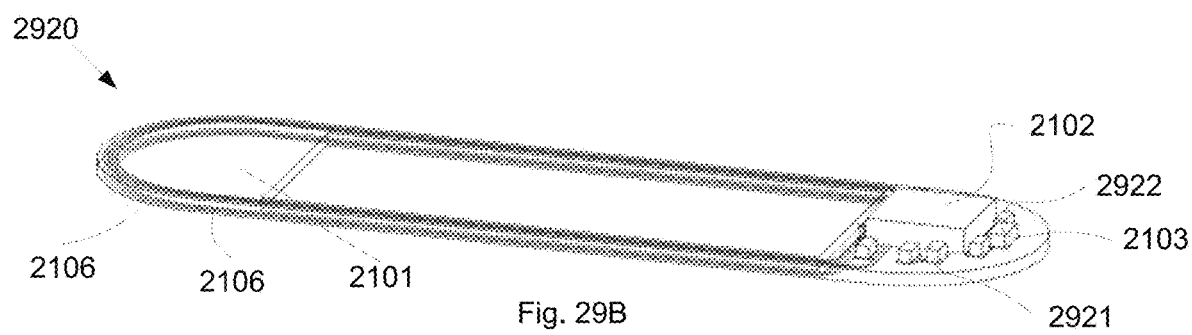

FIG. 29B illustrates a circuit board assembly 2920 for use in a sensing device 120 such as a stir bar where the antenna coil 2106 is implemented as a trace on the top and on the bottom of the circuit board 2101. The electrical connections between the circuit board 2101 and the various circuit elements like the integrated circuit 2102, the sensing element 2103, capacitor 2921 and resistive element 2922 can be made by using solder, the solder can be high temperature solder such as FCT Assembly SN100C or the electrical connections can be made by using conductive adhesives such as a conductive epoxy or conductive silicone, an example is silver filled epoxy such as LOCTITE ABLESTIK 84-1LMI. The use of high temperature assembly methods such as high temperature solder or conductive adhesive aid the circuit board assembly 2920 in withstanding the processing needed for applying the encapsulation 2105 and withstanding use conditions of the sensing device 120.

Figure 29C:
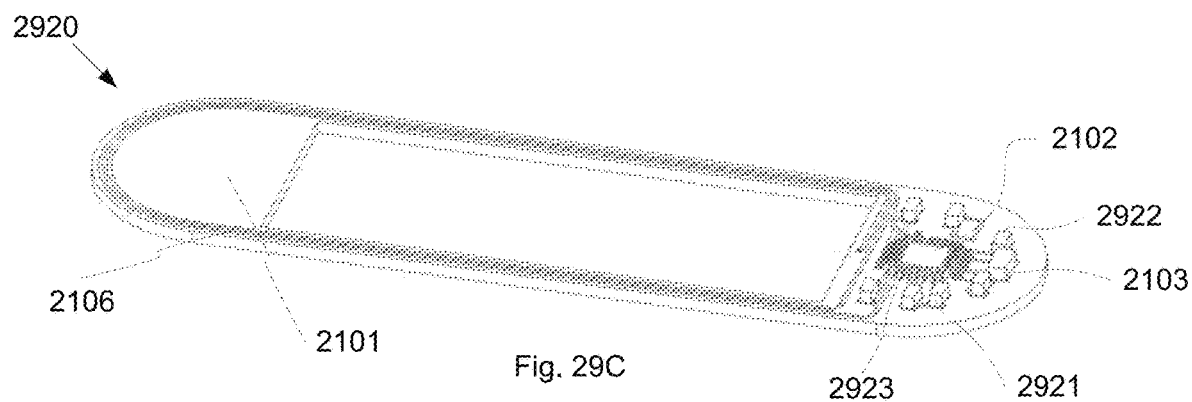

FIG. 29C illustrates a circuit board assembly 2920 for use in a sensing device 120 such as a stir bar where the integrated circuit 2102 is provided in silicone die form and where the electrical connections to the integrated circuit 2102 are made by wire bonding 2923, the wire bonding 2923 can be made by using gold wires or aluminum wires or copper wires. Wirebonding of components can typically withstand relatively high temperature which the sensing device 120 may be exposed to during assembly of the sensing device 120 or during use. The electrical connections to the various components on the circuit board 2101 can be a combination of assembly methods such as wire bonding, soldering and/or conductive adhesive.

Figure 30A:
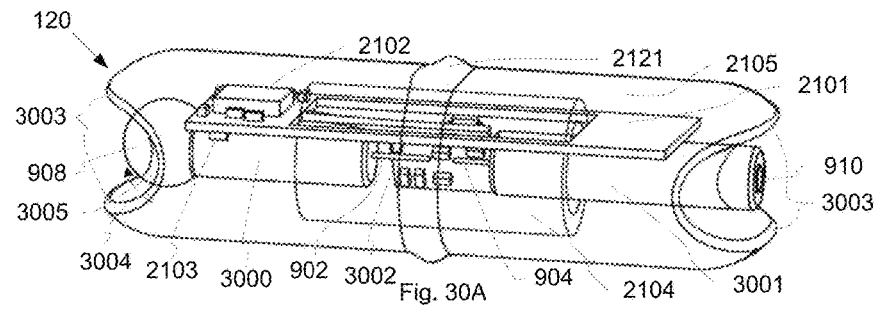
FIG. 30A through 30N illustrates an example sensing device configured as a wireless pH sensor and storage container for such. (There are no FIGS. 30i and 30o.)

FIG. 30A-30F illustrates an example sensing device 120 configured as a wireless pH sensor. As shown in FIG. 30A, the pH sensor can include the wireless communication circuit board 2101, a first electrode 902, a second electrode 904, H+ selective glass 908, and a porous junction or porous frit 910. The circuit board 2101 can measure a voltage difference between the first electrode 902 and the second electrode 904, determine the pH of the substance 115 based on the voltage difference, and report the pH to a wireless receiver. The circuit board 2101 can contain a temperature sensor 2103. The sensing device 120 can further include a magnet and/or ballast 2104 allowing the sensing device 120 to function as an agitator and/or stabilizing the sensing device 120. The magnet or ballast 2104 can be a hollow tube-shaped component where electronic components and/or sensor components can pass through parts of the magnet or ballast 2104. The magnet or ballast 2104 can be made from neodymium magnet material or other magnetic materials or other metals that can be magnetically activated. In one embodiment the signal from the first electrode 902 and/or second electrode 904 can be amplified and/or buffered by circuit components 3002 inside the outline of the magnet or ballast 2104 whereby the magnet or ballast 2104 provides partial shielding of the signals from the first electrode 902 and/or second electrode 904 and/or amplifier circuit 3002. The H+ sensitive glass 908 can be part of a glass body 3000. The porous junction or porous fit 910 can be inserted in a glass body 3001. The sensing device 120 can have a casing 2105. The casing 2105 can encapsulate in a fluid-tight chamber the circuit board 2101 and magnetic member 2104 and amplification circuit 3002 and expose part or all the H+ sensitive electrode 902 to the surrounding liquid and expose the porous junction or porous frit 904 to the surrounding liquid. The casing 2105 can be made from plastics, glass, rubber, epoxy, metal or combinations thereof. The casing 2105 can be a barrier between the substance 115 and electronics internal to the sensing device 120. The casing can have protrusions 3003 such that the sensor surfaces 908 and 910 are protected from direct contact with other surfaces external to the sensing device, but where the sensor surfaces 908 and 910 are in contact with external liquid. For example, if a sensing device 120 is dropped into a container with liquid then the protrusions 3003 can protect the sensor surfaces 908 and 910 from coming in contact and possibly be damaged by the bottom surface or side surfaces of the container. The casing 2105 can be designed such that the casing is retracted on both sides 3005 of the sensing surface 908 such that if the sensing device 120 is in rotation in a liquid then the liquid can freely flow 3004 by the sensing surface 908. The casing 2105 can have a center protrusion 2121 near the center of rotation on at least the top and the bottom surface for promotion of stable rotation as well as lifting the sensor off the bottom thereby increasing the contact with the liquid rather than the floor surface of a container thereby enhancing thermal contact.

Figure 30B:
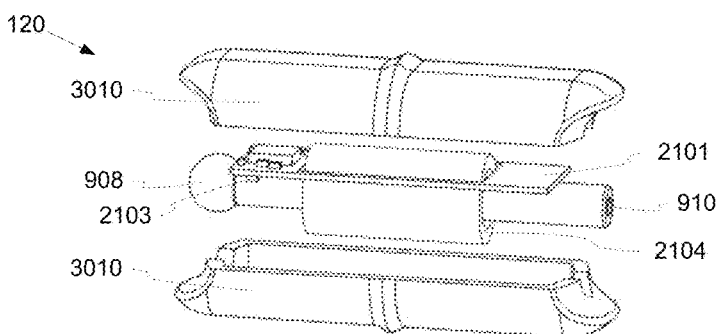
FIG. 30P illustrates a system for measuring pH of a liquid wirelessly.

FIG. 30B illustrates how a sensing device casing can be constructed of two or more casing sections 3010 that are combined to make the casing for the sensing device 120. The casing sections 3010 can be a barrier between the substance 115 and electronics internal to the sensing device 120. The casing sections 3010 can for example be made of glass or ceramic or epoxy or plastic like PEEK, Polypropylene, COC, COP, Polyimide or any other plastic that can provide a barrier between the internal components and the substance 115 which the sensing device 120 will be exposed to. The casing sections 3010 can be combined using epoxy or other glue or laser welding or ultrasonic welding or by heating or by soldering or a combination thereof. The casing sections 3010 can be fused together by heat. The casing sections can be put together using solvent bonding. If there are internal cavities between the combined casing sections 3010 and the internal components in the sensing device 120 then those cavities can be filled with epoxy or silicone or other glue or potting material like thermally conductive gap filler PL-BT-603-50M from Wakefield-Vette where the potting material provides a higher level of thermal conductivity and thereby enable better temperature measurement of the surrounding substance 115 by the temperature sensor 2103.

Figures 30C, 30D, 30E:
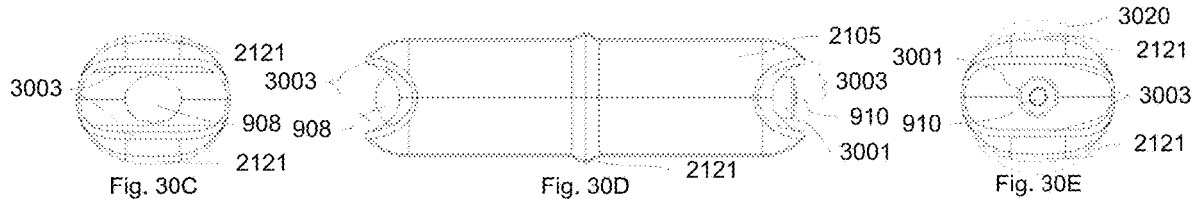

FIG. 30C shows an end-view of the sensing device 120.

FIG. 30 D shows a side-view of the sensing device 120.

FIG. 30E shows a second end-view of the sensing device 120.

Figure 30F:
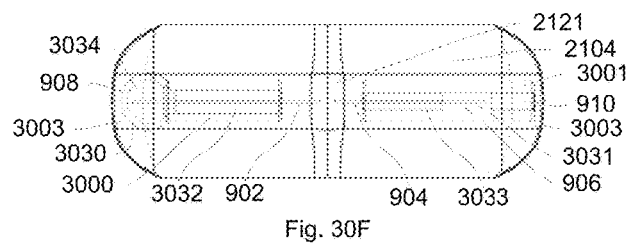

FIG. 30F shows a top-view of the sensing device 120. In FIG. 30F the sensor component 908 and 910 are shown in more detail. The sensor surface 908 is part of a glass body 3000 where an internal chamber 3030 is partly or fully filled with liquid or gel 3034 such as KCl. The chamber 3030 is formed by the outer glass surfaces 908 and 3000 and of a plug 3032 made of glass or epoxy or silicone or other glue. There is an electrode 902 connecting the internal chamber 3030, the electrode 902 can be a silver chloride electrode. The porous junction or porous frit 910 is in a glass body 3001 where an internal chamber 3031 is partly or fully filled with liquid or gel 906 such as KCl. The chamber 3031 is formed by the outer glass surfaces 3001 and porous junction or porous frit 910 and of a plug 3033 made of glass or epoxy or silicone or other glue. There is an electrode 904 connecting the internal chamber 3031, the electrode 904 can be a silver chloride electrode.

Figure 30G:
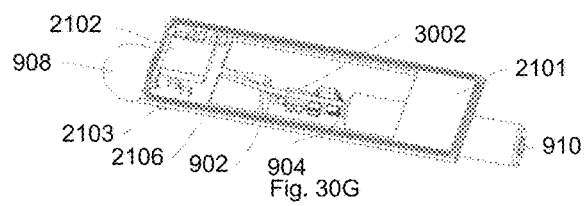

FIG. 30G illustrates an electronic circuit board 2101 for use in sensing device 120. The circuit board can have amplification components 3002 for amplifying or buffering the signal from the electrodes 902 and 904. The amplification circuit components 3002 can be on the same physical circuit board 2101 or they can be on a separate circuit board connected to the circuit board 2101. The electronic circuit 2101 can have a temperature sensor 2103 for sensing temperature of the liquid and for compensate the pH reading due to the liquid temperature. The circuit board 2101 can have an integrated circuit 2102 for converting the analog pH reading signal and transmitting it wirelessly over the antenna 2106.

Though FIGS. 30A to 30G describes a pH sensing device 120, the same device can be used for sensing lithium, sodium, ammonium, and other ions by having the H+ sensitive glass 908 instead be sensitive to other ions. The sensor 120 can have the sensor surface 908 and porous junction 910 be placed on the same end of the sensing device 120. The sensing device 120 can contain a combination of sensing elements such as temperature, pH, sodium, ammonia, lithium, potassium, calcium, specific gravity, refractive index, viscosity, salinity, conductance, color, absorbance, fluorescence, pressure, electrochemical, conductivity, chemiluminescence, liquid level, rotation, acceleration, velocity, dissolved oxygen or $CO_2$. The porous junction or porous frit 910 can be a double junction. The liquid or gel electrolyte 3034 that is behind the glass surface 908 can be polymerized to be semi or fully solid. The liquid or gel electrolyte 906 that is behind porous junction or porous frit 910 can be polymerized to be semi or fully solid. The sensor half cell 908 could be an ion selective field effect transistor (ISFET). The reference electrode 910 can be single or double junction and could use two layers of solid polymer electrolyte in direct contact with each other to form one junction of the double junction. For example a first gel electrolyte without silver would be in contact with the porous frit 910 and a second gel electrolyte with silver would create a contact between the first gel electrolyte and the electrode 904. Instead of using a porous frit a solid or semi solid electrolyte can be used. Using a solid electrolyte as a reference can avoid the problem of clogging of a porous frit in some applications.

Figure 30H:
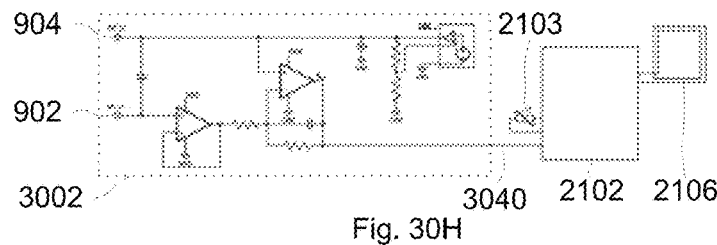

FIG. 30H illustrates a circuit schematic for the circuit board 2101 for use in a sensing device 120 for pH sensing. The amplification portion 3002 of the circuit can generate a signal 3040 as a result of voltage potential difference from the electrodes 902 and 904. The signal 3040 is routed to a wireless integrated circuit 2102 which contains an Analog to Digital converter for converting the analog signal to a digital value that can be transmitted as wireless data over the antenna 2106. The circuit can have a temperature sensor 2103 for measuring the temperature at the sensing device 120 and transmitting it wirelessly or to compensate the pH reading signal 3040 and transmitting a value that is indicative of a pH reading compensated for temperature.

Figure 30J:
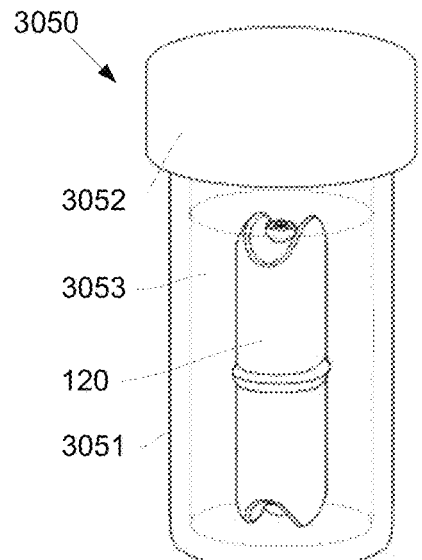

FIG. 30J illustrates a system 3050 for storing a wireless sensing device 120 when not in use, this is useful when a wireless sensing device 120 needs to be stored in a specific environment in order to maintain functionality, for example a pH sensitive sensor is stored in 4M KCl solution, this is often problematic to do with a classic wired pH electrode, because it is challenging to get a good seal around an electrode and therefore the KCl solution can evaporate and/or create salt crystals around the pH electrode. The storage system 3050 shows a container 3051 that can be closed with a lid 3052 and where the container holds the wireless sensing device 120 in a substance 3053, for example the substance 3053 can be a liquid 4M KCl solution for a pH sensing device 120. The lid 3052 can seal to the container 3051.

Figure 30K:
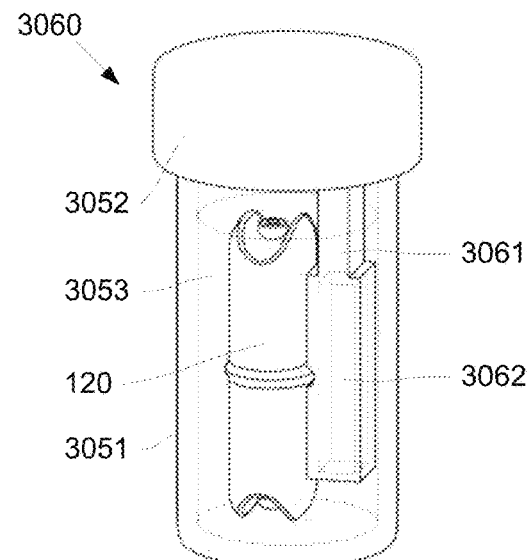

FIG. 30K illustrates another embodiment of a system 3060 for storing a wireless sensing device 120 when not in use. The storage system 3060 shows a container 3051 that can be closed with a lid 3052 and where the container holds the wireless sensing device 120 in a substance 3053, for example the substance 3053 can be a liquid 4M KCl solution for a pH sensing device 120. The lid 3052 can have a member 3061 attached wherein metal or a magnet 3062 can magnetically attract the wireless sensing device 120 and whereby the removal of the lid 3052 can move the wireless sensing device 120 from the container 3051.

Figure 30L:
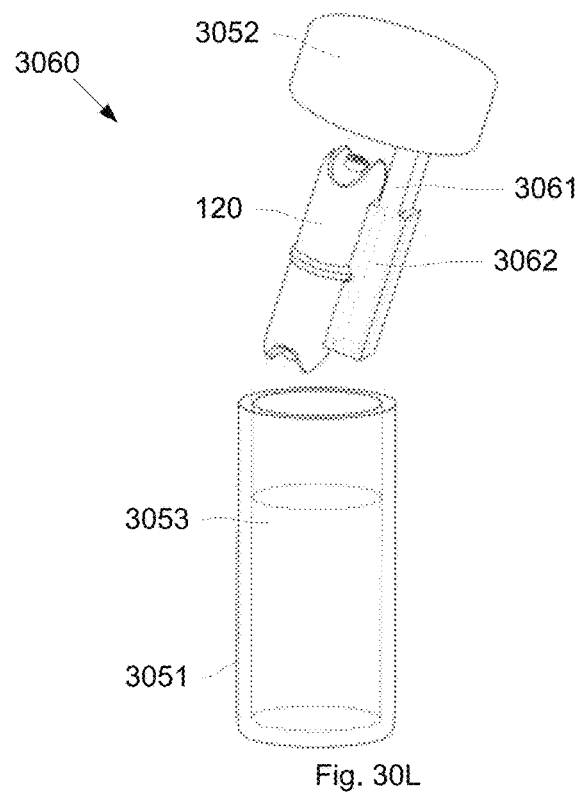

FIG. 30L illustrates a system 3060 for handling a wireless sensing device 120 when not in use, the storage system 3060 shows a container 3051 that can be closed with a lid 3052 and where the lid 3052 can have a member 3061 attached wherein metal or a magnet 3062 can magnetically attract the wireless sensing device 120 and whereby the removal of the lid 3052 can move the wireless sensing device 120 from the container 3051. FIG. 30L shows how the wireless sensing device is held by magnetic attraction to the member 3061 on the lid 3052 and thereby the user does not need to touch the sensing device 120 or the substance 3053 directly to remove the sensing device 120 from the container 3051 and substance 3053. The member 3061 can have many length in order to accommodate specific sensing device sizes or container sizes, it can be used to retract the sensing device 120 from a measurement setup by attracting the sensing device 120 from the container that holds the substance to be measured by use of magnetic attraction, as long as the magnetic attraction to the sensing device 120 from metal or magnet 3062 is stronger than other forces on the sensing device 120.

Figure 30M:
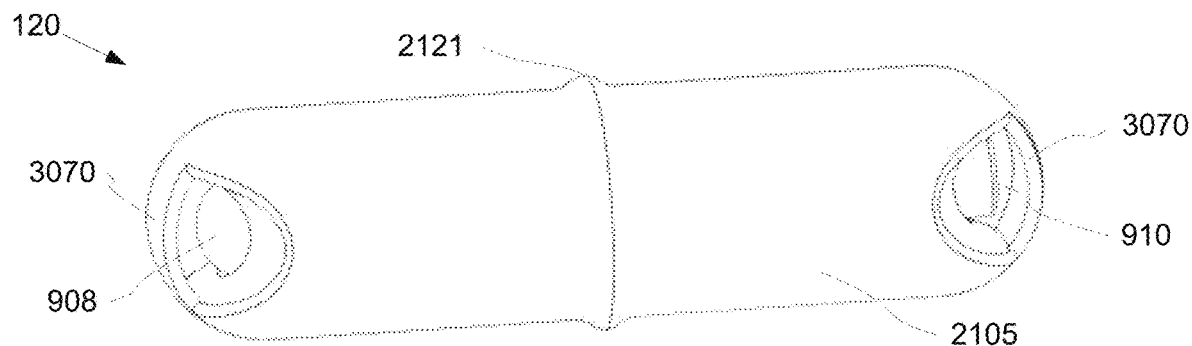

FIG. 30M illustrates a wireless sensing device 120 for measuring pH where the pH sensitive glass 908 is positioned behind a member 3070 that functions as a mechanical barrier against mechanical damage of the pH sensitive glass 908.

Figure 30N:
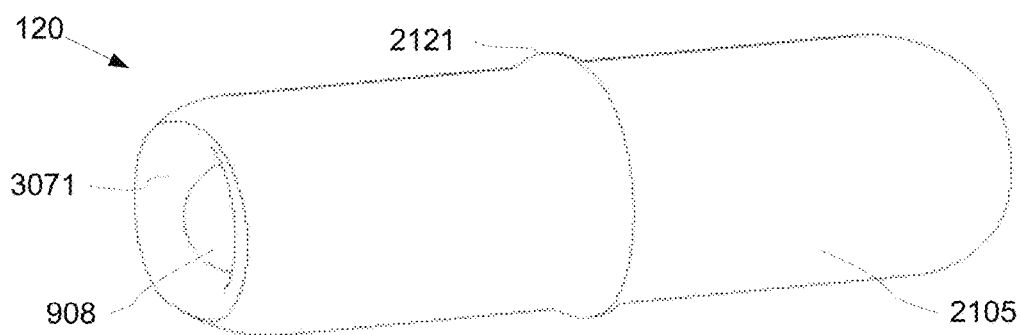

FIG. 30N illustrates a wireless sensing device 120 for measuring pH where the pH sensitive glass 908 is positioned in a recession 3071 in the casing 2105 such that the casing 2105 around the recess 3071 functions as a mechanical barrier against mechanical damage of the pH sensitive glass 908.

Figure 30P:
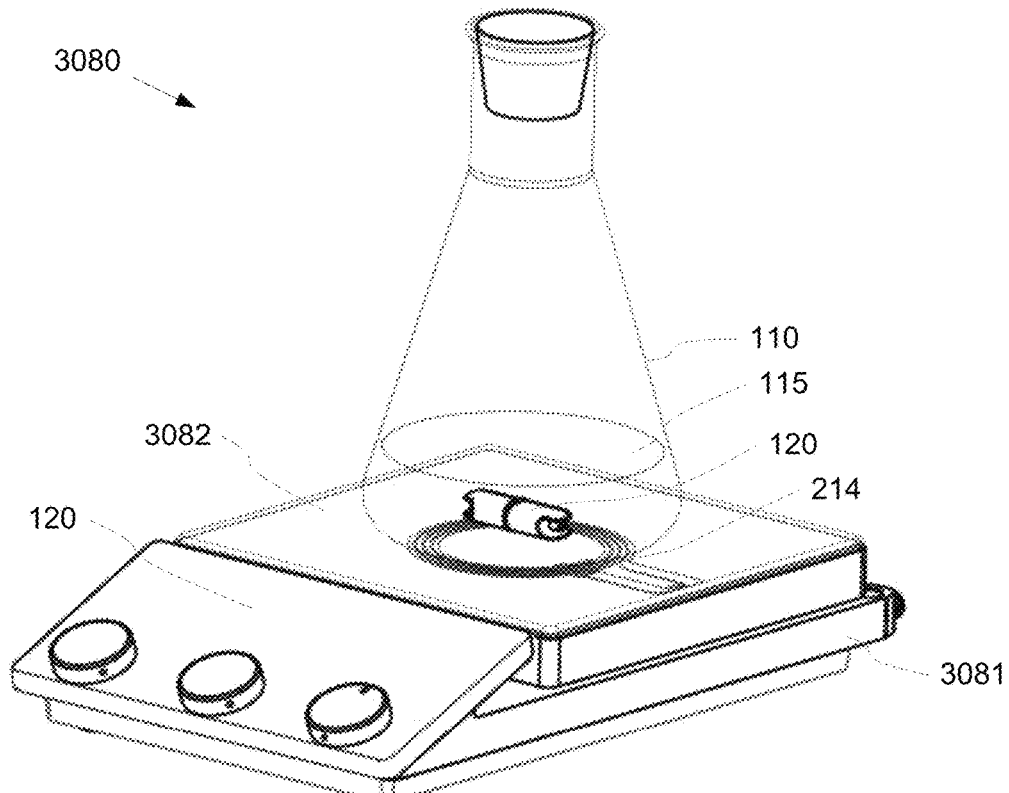

FIG. 30P illustrates a system 3080 for measuring pH in liquid 115 in a container using a wireless sensing device 120 where the sensing device 120 can measure pH and transmit the measurement wirelessly to be received by antenna 214 in instrument 3081. The instrument 3081 also powers the wireless sensing device 120 by providing wireless energy from antenna 214. Optionally the Instrument 3081 also is able to generate a varying magnetic field which can induce a stirring motion in the wireless sensing device 120 when the sensing device 120 contains a magnet. The measured values from the wireless sensing device 120 can be displayed on the screen 120 of the instrument 3081. The system 3080 can also be used where the sensing device 120 is configured to measure one or more of the following parameters: temperature, pH, sodium, ammonia, lithium, potassium, calcium, specific gravity, refractive index, viscosity, salinity, conductance, color, absorbance, fluorescence, pressure, electrochemical, conductivity, chemiluminescence, liquid level, rotation, acceleration, velocity, dissolved oxygen or $CO_2$.

FIG. 31A illustrates a container 3101 which can have a detachable lid 3102 which is connected to a rotation member 3103 where the rotation member 3103 is free to rotate in relation to the lid 3102 and where the rotation member includes a sensing member 3104, where the sensing member 3104 is able to measure a parameter of the substance 115 and wirelessly transmit the measurement to a receiver 210. The rotating member 3103 can contain a magnet or metal 3105 that can be activated with an external magnetic field generated from the receiver 210, whereby the rotating member 3103 as well as the sensing member 3104 rotates. There can be blades 3106 on the rotating member 3103 such that the substance 115 can be mixed even with slow rotation of rotating member 3103. The container 3101 can have ports 3107 with separate lids 3108 for accessing the substance 115 for example for extracting part of substance 115 or for adding compounds to substance 115 or for inserting measurement probes. The sensing device 3104 can be permanently attached to the rotating member 3103 or it can be removable from the rotating member 3103. The wireless receiver 210 can in one embodiment provide heating or cooling to the container 3101, where the heating or cooling can in one embodiment be regulated by the measurements received wirelessly from the sensing device 3104. The wireless receiver 210 can be a separate device from the device that generates the magnetic field for rotating the rotation member 3103. The rotation or the rotation member 3103 can be done by a mechanism attached to the lid 3102 by a direct mechanical link or by magnetic force. If the rotation of the rotation member 3103 is done by a mechanical link, then the magnet or metal 3105 can be eliminated from the rotation member 3103. The sensing member 3104 can be a type that measures the rotation of the sensing member 3104. The sensing device 3104 can be powered by a one-time use battery or a rechargeable battery or it can have no battery and be powered by wireless energy like for example a RFID wireless receiver operating at 13.56 MHz or another frequency. Instead of the wireless receiver being part of 210, then the wireless receiver can be in the lid 3102 or the wireless receiver can be an external device such as a smartphone or PC. In the embodiment where the sensing device 3104 is powered by wireless energy the source of the wireless energy can be a separate device from the device that receives the wireless measurement data from the sensing device 3104.

FIG. 31B illustrates a container 3101 which can have a detachable lid 3102 which is connected to a rotation member 3103 where the rotation member 3103 is free to rotate in relation to the lid 3102 and where the rotation member includes a first sensing member 3104, where the first sensing member 3104 is able to measure a first parameter of the substance 115 and wirelessly transmit the measurement to a receiver 210 and where the rotation member 3103 includes a second sensing member 3110, where the second sensing member 3110 is able to measure a second parameter of the substance 115 and wirelessly transmit the measurement to a receiver 210. The rotating member 3103 can contain a magnet or metal that can be activated with an external magnetic field generated from the receiver 210, whereby the rotating member 3103 as well as the sensing members 3104 and 3110 rotates. There can be blades 3106 on the rotating member 3103 such that the substance 115 can be mixed even with slow rotation of rotating member 3103. The first sensing member 3104 or the second sensing member 3110 can be a type that measures the rotation of the sensing member. The first sensing member 3104 and the second sensing member 3110 can be electrically connected and thereby have a single wireless system for transmitting measured values to the receiver 210 or the first sensing member 3104 and the second sensing member 3110 can each have its own wireless system for transmitting measurements to the receiver 210. The rotation member 3103 can have one or multiple sensing members for measuring various parameters.

FIG. 31C illustrates a container 3101 which can have a detachable lid 3102 which is connected to a rotation member 3103 where the rotation member 3103 is free to rotate in relation to the lid 3102 and where the rotation member includes a first slot 3111 for a first sensing member 3104, where the first sensing member 3104 is able to measure a first parameter of the substance 115 and wirelessly transmit the measurement to a receiver 210 and where the rotation member 3103 includes a second slot 3112 for a second sensing member 3110, where the second sensing member 3110 is able to measure a second parameter of the substance 115 and wirelessly transmit the measurement to a receiver 210 and where the rotation member 3103 includes a third slot 3113 for a third sensing member, where the sensing members can be inserted and removed by a user for configuring a system to a specific user need. The rotating member 3103 can contain a magnet or metal that can be activated with an external magnetic field generated from the receiver 210, whereby the rotating member 3103 as well as the sensing members 3104 and 3110 rotates. There can be blades 3106 on the rotating member 3103 such that the substance 115 can be mixed even with slow rotation of rotating member 3103. There can be one or multiple slots in the rotation member 3103 for inserting sensing members into the rotation member 3103 for measuring various parameters. FIG. 31D illustrates a lid 3102 which is connected to a rotation member 3103 where the rotation member 3103 is free to rotate in relation to the lid 3102 and where the rotation member includes a first slot 3111 for a first sensing member 3104, where the first sensing member 3104 is able to measure a first parameter of the substance 115 and wirelessly transmit the measurement to a receiver 210 and where the rotation member 3103 includes a second slot 3112 for a second sensing member and where the rotation member 3103 includes a third slot 3113 for a third sensing member, where the sensing members can be inserted and removed by a user for configuring a system to a specific user need. The rotating member 3103 can contain a magnet or metal that can be activated with an external magnetic field generated from the receiver 210, whereby the rotating member 3103 as well as the sensing members 3104 rotates. There can be blades 3106 on the rotating member 3103 such that the substance 115 can be mixed even with slow rotation of rotating member 3103. There can be one or multiple slots in the rotation member 3103 for inserting sensing members into the rotation member 3103 for measuring various parameters.

Figure 32:
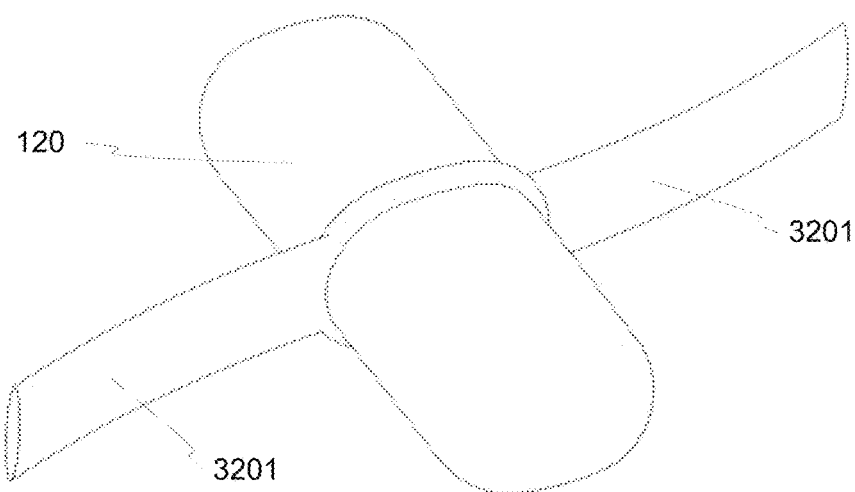
FIG. 32 illustrates an example sensing device configured with extra stirring members.

FIG. 32 illustrates a wireless sensing device 120 where there are blades 3201 attached to the exterior of the body such that when the sensing device 120 rotates the blades 3201 can provide stirring or mixing of a substance 115 that the sensing device 120 is submerged in.

Figure 33:
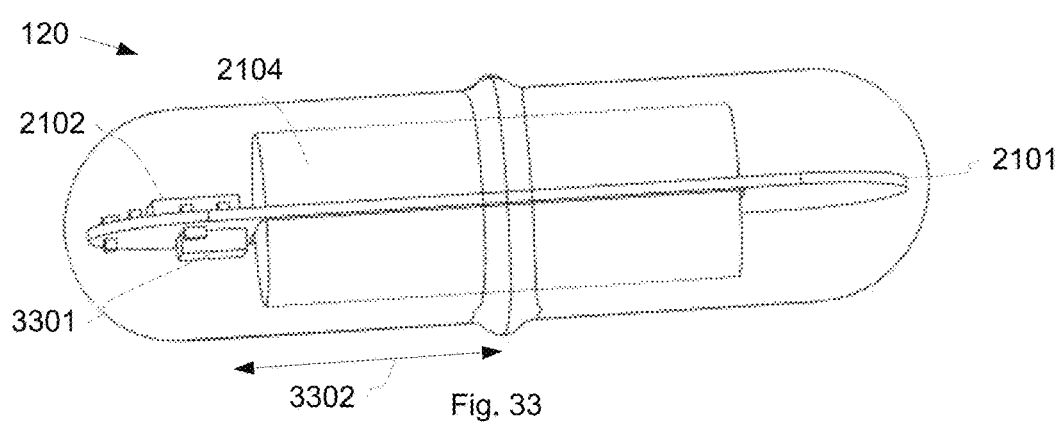
FIG. 33 illustrates an example sensing device configured to sense rotation of the wireless sensing device.

FIG. 33 illustrate an example of a wireless sensing device 120 configured to measure the rotation velocity of the sensing device 120. The sensing device 120 can include a circuit board 2101 supporting the integrated circuit 2102 and a sensing component 3301 in electrical communication with the integrated circuit 2102. The sensing component 3301 can be a gyroscope for measuring rotation or the sensing component 3301 can be an accelerometer that measures the centripetal force exposed to the sensing component 3301 when the sensing device 120 is rotated. For example, the sensing component 3301 can be a Freescale FXLN8372QR1 accelerometer that measures the centripetal force as the sensing device 120 is rotated when the sensing component 3301 distance 3302 from the center of rotation is known. The sensing device 120 can further include a metal member or a magnet 2104, enabling the sensing device 120 to agitate or mix the substance 115 in a container 110 when the sensing device 120 is exposed to an external magnetic field. The sensing component 3301 can measure acceleration or gyration in more than one axis and thereby detect movement in other than the rotation axis whereby abnormal behavior can be detected. The sensing device 120 can include a temperature sensor and other sensors for measuring other parameters. An antenna 2106 can be implemented on the circuit board 2101 or as a separate component to transmit the measured rotation or other parameters to a receiver wirelessly.

Figure 34:
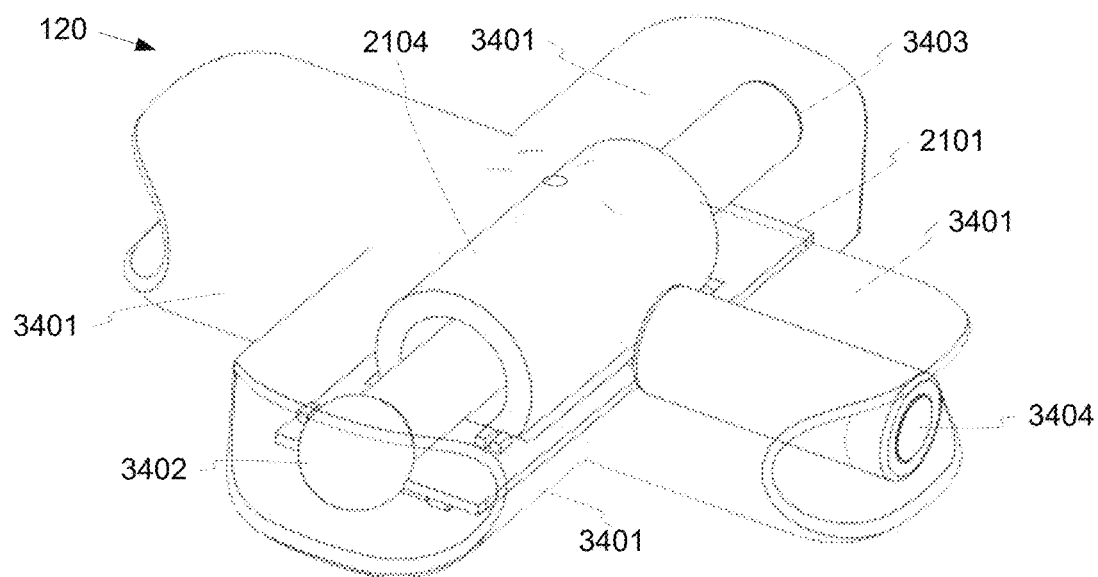
FIG. 34 illustrates an example sensing device configured to sense multiple parameters of a substance.

FIG. 34 illustrate an example of a wireless sensing device 120 configured to measure several parameters of a substance 115 wherein the sensing device 120 is submerged. The sensing device 120 is configured with 4 arms 3401 which can each contain a sensing element for sensing a parameter of the substance 115. For example, one sensing element can be a pH sensitive element 3402. Another sensing element can be a reference element 3403 for providing a reference for the pH sensitive element 3402, another sensing element can be a clark type sensor 3404 for sensing dissolved oxygen. The sensing device 120 can include a circuit board 2101 supporting one or more integrated circuit 2102 and providing electrical connection to the sensing elements 3402, 3403, 3404 and possibly a temperature sensor and possibly a rotation sensor. The sensing device 120 can further include a metal member or a magnet 2104, enabling the sensing device 120 to agitate or mix the substance 115 in a container 110 when the sensing device is exposed to an external magnetic field. An antenna 2106 can be implemented on the circuit board 2101 or as a separate component to transmit the measurements and other parameters to a receiver wirelessly. The sensing device 120 can have 3 or 4 or more arms 3401. The sensing elements can be located proximal to the exterior end from the axis of rotation of the arms 3401 or the sensing elements can be located other places on the sensing device. The sensing elements can be measuring different characteristic being any of pH, sodium, ammonia, lithium, potassium, calcium, specific gravity, refractive index, viscosity, salinity, conductance, color, absorbance, fluorescence, pressure, electrochemical, conductivity, chemiluminescence, liquid level, rotation, acceleration or velocity, dissolved oxygen or $CO_2$. There can be none, one or multiple sensing elements in each arm 3401. Each arm 3401 can be the same length and shape or they can be different lengths or different shapes.

Figure 35A:
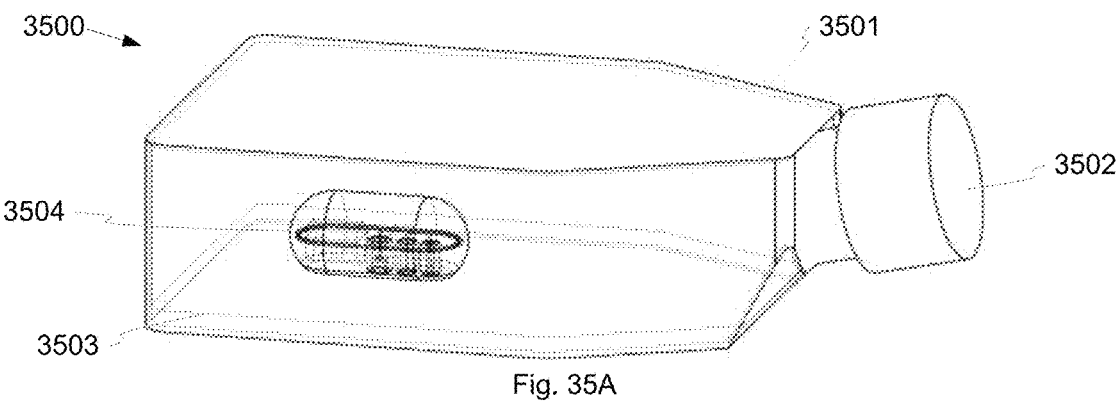
FIG. 35A through 35F illustrates an example sensing device configured for wireless sensing of multiple properties of a substance in a biological container.

FIG. 35A illustrates a system 3500 for measuring properties of a substance 3503 for growing cells in a container 3501, where the container 3501 is closed with a lid 3502. In the container 3501 a wireless sensing device 3504 is located that can measure properties of the substance 3503 or the air or gas in the container 3501 and transmit the measurements wireless to a receiver outside the container 3501. The sensing device 3504 can contain a battery or it can be powered by wireless energy or both. The sensing device 3504 can float on the substance 3503 or it can be standing on the bottom of the container 3501 or the sensing device 3504 can be built into the container 3501. The sensing device 3504 can measure parameters such as pH of the substance 3503, dissolved oxygen in the substance 3503, $CO_2$ in the substance 3503, turbidity of the substance 3503, conductivity of the substance 3503, $CO_2$ in the gas surrounding the substance 3503, temperature or other parameters, the sensing device 3504 can contain a camera and possibly a light source for imaging the substance 3503 and possibly imaging cells in the substance 3503. The lid 3502 can be a type that create a hermetical seal to the container 3501 or it can be a type that can have venting of gas between the inside and the outside of the container 3501 directly or through a membrane or filter or vents.

Figure 35B:
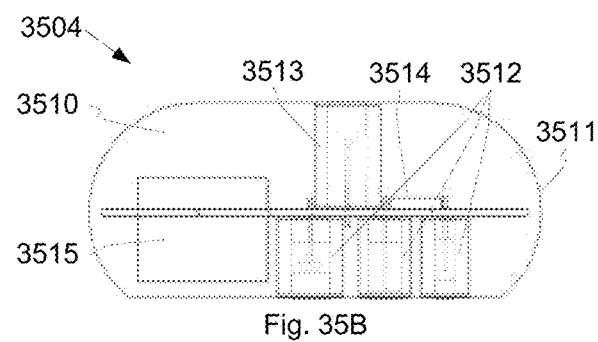

FIG. 35B illustrates an example of a wireless sensing device 3504 configured to measure several parameters of a substance 3503 which the sensing device 3504 is in contact with. The sensing device 3504 can include a circuit board 3511 which can hold an integrated circuit 3514 and which can have several sensor elements 3512 in electrical contact with the circuit board 3511, where the sensing elements 3512 are configured to measure parameters of the substance 3503. The sensing device 3504 can further include one or more sensing elements 3513 for measuring the gas or air above the substance 3503. A casing 3510 can encapsulate the circuit board 3511, and other internal components. Many types of encapsulations may be used for the casing 3511, such as plastics, glass, rubber, or other materials that can provide a barrier between the substance 3503 and electronics internal to the sensing device 3504. For example, the casing 3510 can be constructed from EFEP from Daikon™, which is a fluoropolymer with a relatively low processing temperature point. The sensing device 3504 can further include a ballast 3515 such as a magnet or a battery or any other type of material that is of higher density than the casing 3510 and whereby the ballast 3515 can assure that the sensing device 3504 is oriented such that the sensing elements 3512 are in contact with the substance 3503. An antenna for transmitting measurements wirelessly can be part of the circuit board 3511 or it can be a separate part in the sensing device 3504. The sensing device 3510 can be coated or not coated to limit cell growth on the sensing device 3504. If the sensing device 3504 includes a camera for monitoring the substance 3503 or cells in the substance 3503 then the optical window between the camera and the substance may be retracted such that it is not in direct contact with the substance 3503 or it may be in direct contact with the substance 3503 depending on if the issue of cell growth on the window is to be avoided.

Figure 35C:
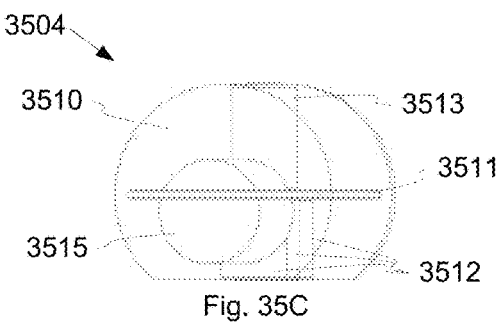

FIG. 35C shows a different view of the sensing device 3504 in FIG. 35B, where the ballast 3515 is shown to be in the lower portion of the sensing device 3504 such that the sensing device 3504 can orient itself such that the sensing elements 3512 can be in contact with the substance 3503 and such that the sensing element 3513 can be in contact with the air or gas above the substance 3503. The casing 3510 is shown surrounding the ballast. In some configuration of the sensing device 3504 the ballast 3515 may not need to be a separate member.

Figure 35D:
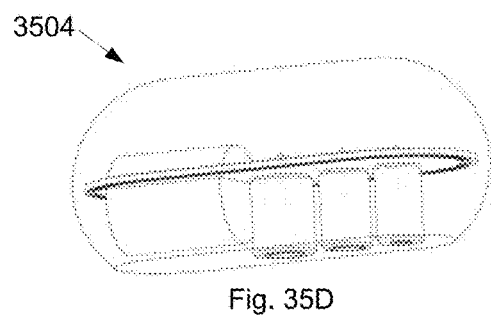

FIG. 35D illustrates an example of a wireless sensing device 3504 where the bottom side is mostly flat.

Figure 35E:
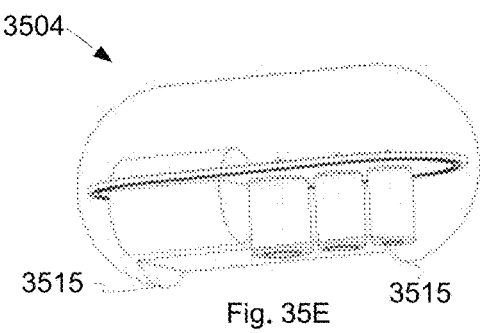

FIG. 35E illustrates an example of a wireless sensing device 3504 where the bottom side can have members 3515 protruding for standing on a bottom surface of a container 3501.

Figure 35F:
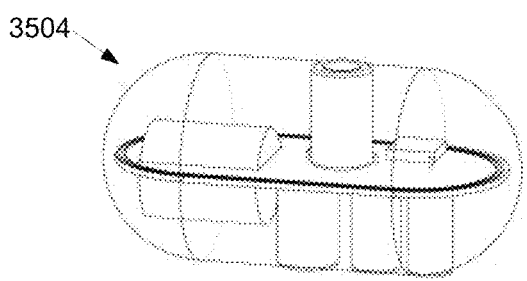

FIG. 35F illustrates an example of a wireless sensing device 3504 where the bottom side is mostly round. The shape of the sensing device 3504 can have many forms when it is able to self orient such that the sensing elements 3512 are in contact with the substance 3503.

FIG. 36A illustrates a system 3600 for transferring a wireless sensing device 120, for example if a wireless sensing device 120 needs to be moved out of a container 110 or into a container 110. By using system 3600 to transfer or handle a wireless sensing device 120 then direct touching of the wireless sensing device 120 can be avoided which can be advantageous in cases where the wireless sensing device 120 can be contaminated or where the wireless sensing device 120 may have been exposed to toxic material or where the wireless sensing device 120 may be hot or slippery. Another reason to use a system 3600 may be if access to a container 110 is limited or where the liquid level is too high to easily reached a wireless sensing device 120 by hand directly or where the liquid in a container 110 is hot or cold or in other ways uncomfortable to handle by hand directly. The system 3600 consists of a region 3601 that can attract a magnet 2104 in a wireless sensing device 120 and where the attraction of the magnet 2104 in the wireless sensing device 120 can be enabled or disabled by the pressing or activation of a mechanical member 3604. The system 3600 may have mechanical members or protrusion 3602 that confines the movement of a wireless sensing device 120. The system 3600 may have a mechanical member 3603 that connects the region 3601 and the area where the mechanical activation member 3604 is located. The mechanical member 3603 may be tube shaped. The mechanical member 3603 may have an area 3611 distal to the region 3601 where a person can hold the system 3600.

FIG. 36B illustrates another embodiment of a system 3600 for transferring a wireless sensing device 120. The hand 3610 of a person is shown to indicate a possible way that the system 3600 would be held. The region 3601 where a wireless sensing device 120 can be magnetically attracted has protruding mechanical members 3605 for confining the movement of the wireless sensing device 120. The figure also illustrates a surface 3602 for confining the region 3601 where a wireless sensing device 120 can be located. Also shown is a mechanical member 3603 for connecting the region 3601 to the area where a person may hold the system 3600. Mechanical activation member 3604 is shown to be possible to activate by the thumb of a person's hand 3610 providing activation force.

FIG. 36C illustrates the internal mechanism of a system 3600 for transferring a wireless sensing device 120. The activation member 3604 can be connected to a magnetically attractive member 3606 with a mechanical member 3607 such that by activating or pressing the activation member 3604 partly or fully into the mechanical member 3603 then the magnetically attractive member 3606 can be moved into the region 3601 and thereby the magnet 2104 in a wireless sensing device 120 can make the wireless sensing device 120 attracted to the region 3601. The movement of activation member 3604 can be counter acted by a spring 3608 such that the magnetically attractive member 3606 can be moved out of region 3601 upon release of activation member 3604. The magnetically attractive member 3606 can be any type of magnet or metal that is attracted by a magnet.

FIG. 36D illustrates another state of the system 3600 depicted in FIG. 36C. The figure shows the activation member 3604 pressed into the mechanical member 3603 such that the magnetically attractive member 3606 can be moved into the region 3601 and thereby a wireless sensing device 120 can be attracted to the region 3601. The spring 3608 can be compressed.

FIG. 36E illustrates a system 3600 for transferring a wireless sensing device 120 where the system has a feature 3609 that can work as a lid for a storage container 3051 such that when a wireless sensing device 120 needs to be stored in for example a KCl solution 3053 then the feature 3609 can function as a partial or full lid for the container 3051.

Figure 36F:
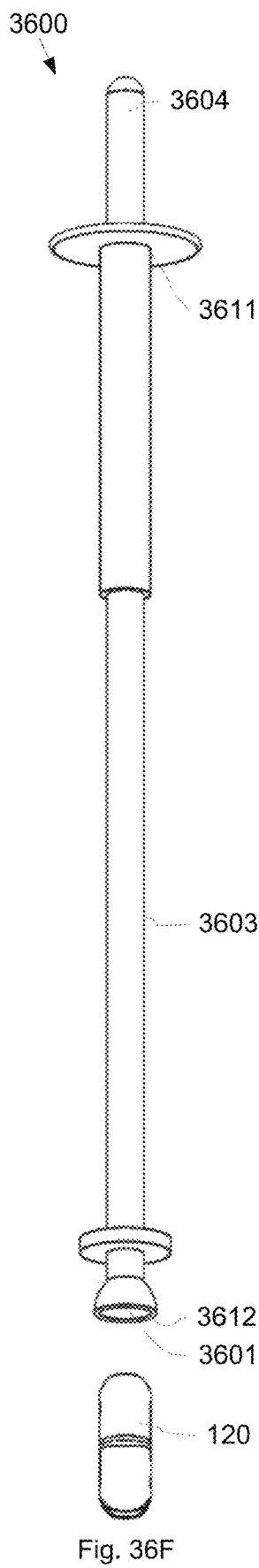

FIG. 36F illustrates another embodiment of a system 3600 for transferring a wireless sensing device 120. The region 3601 where a wireless sensing device 120 can be magnetically attracted is surrounded by a mechanical structure 3612 that guides the sensing device 120 such that the end of a sensing device 120 can be attracted to area 3601 and the sensing device 120 can extend away from area 3601 in a manner where the long axis of the sensing device 120 is somewhat in line with the mechanical member 3603.

Figure 36G:
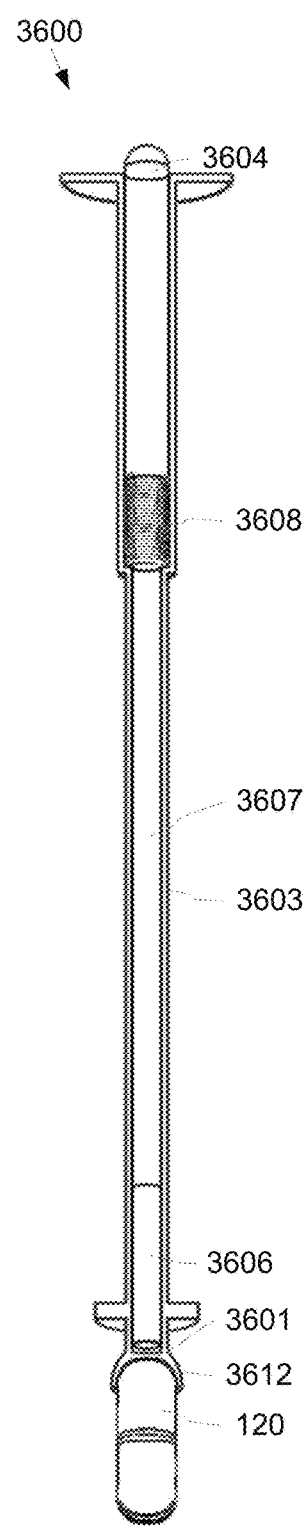

FIG. 36G is a cut through illustration of another state of the system 3600 depicted in FIG. 36F. The figure shows the activation member 3604 pressed into the mechanical member 3603 such that the magnetically attractive member 3606 is moved in proximity of the region 3601 and thereby a wireless sensing device 120 is attracted to the region 3601. The spring 3608 can be compressed.

Figure 36H:
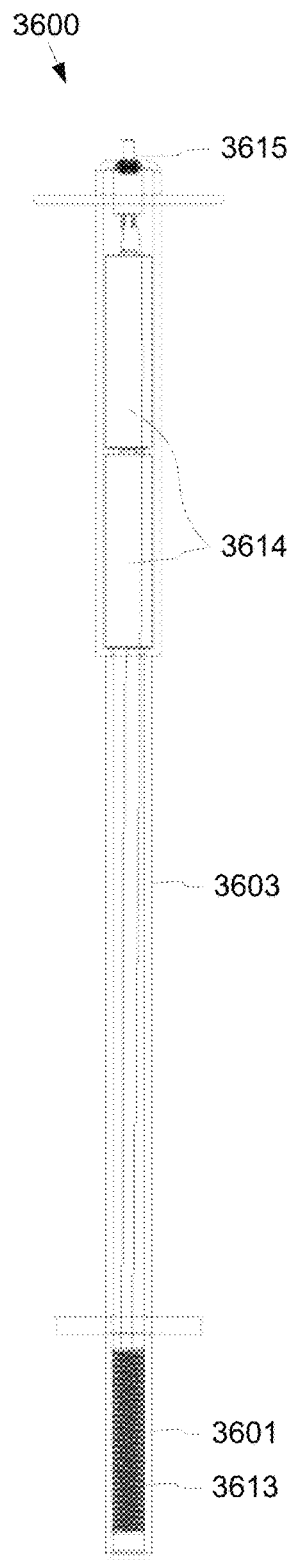

FIG. 36H illustrates another embodiment of a system 3600 for transferring a wireless sensing device 120. The magnetic attraction can be accomplished by an electromagnet 3613 embedded in region 3601. The electromagnet 3613 can be powered by one or more batteries 3614 by closing an electrical switch 3615. The device can function such that a the wireless sensing device 120 can be attracted to region 3601 upon closing of an electrical switch 3615 such that power flows from the batteries 3614 to the electromagnet 3613 or it can be configured such that the electromagnet 3613 can be a permanent electromagnet which normally has a magnetic field when no power is applied and therefore attracts a sensing device 120 to region 3601 but when the electrical switch 3615 is closed and power flows from the batteries 3614 to the electromagnet 3613 then the magnetic field can be neutralized and the sensing device 120 can be released from region 3601. The device illustrated in FIG.

36H may contain additional components such as power regulation circuitry or charging accommodation in the case that the batteries 3614 are rechargeable. The outer areas of the transfer device of system 3600 may be made of a plastic material like for example PTFE, COC, COP, PEEK or Polypropylene or other plastic materials, depending on the use situation and what chemical exposure the system can see then a material can be selected that is inert to the specific environment, other materials may be ceramic or non-magnetic stainless steel or other non magnetic materials. The system 3600 may also be used to transfer or handling of traditional non sensing magnetic stir bars or other magnetic items. The system 3600 can be designed in other ways such that the activation of the magnetic attraction to a wireless sensing device 120 may happen by other means than having a mechanical member pressed into a structure for example pressing a lever or rotating a mechanical member. The transferring device can attract and move the sensing device 120 in a manner where the long axis of the sensing device 120 is pointing away from the activation member 3604 or switch 3615, but many other configurations and orientations are possible.

Figure 37A:
FIG. 37A through 37D illustrates an example configuration of a sensing devices configured to measure temperature and other parameters.

FIG. 37A illustrates a wireless sensing device 120, such as a stir bar, that can be configured to measure the temperature of a substance. The sensing device 120 can have a circuit board 2101 supporting an integrated circuit 2102 and a temperature sensing element 2103 readable by the integrated circuit 2102. The circuit board 2101 may have an embedded antenna (not shown) for communication and power. The sensing device 120 may contain a magnet 2104 or a metal that is magnetically affected such as iron. The wireless sensing device may be enclosed in an enclosure 2105 which may be made of glass where the one end 3703 of the enclosure 2105 may be formed before the internal components are implemented and where the other end 3704 is closed and formed after the internal components are implemented. FIG. 37A illustrates an example of the sensing device 120 before the end 3704 is closed or sealed. In case of the enclosure 2105 being glass then the closing and forming of the glass is a high temperature event which can damage the internal components of the sensing device 120, therefore there may be a need to have the circuit board 2101 shortened such that it is further away from the end 3704 that is closed by use of high heat. A thermal barrier 3702 can limit the heat that exposes the internal components of sensing device 120 when the end 3704 of the sensing device 120 is formed or closed with heat. Such a barrier 3702 can be made of for example high temperature ceramic fibers. The internal cavity 3701 of the sensing device 120 may be filled with or partly filled with a polymer in order to secure the internal components of sensing device 120 from moving around in the internal space and to enhance the thermal connection from the temperature sensing element 2103 and the environment. The polymer can be for example a thermally conducting polymer like Wakefield-Vette PL-BT-603-50M such that the temperature sensing element 2103 has a good thermal connection to the enclosure 2105 and thereby a good thermal connection to the surrounding environment which would enhance the accuracy and speed at which the temperature of the environment can be measured. The antenna may for the wireless sensing device 120 may be a separate member that is not embedded in the circuit board 2101.

Figure 37B:
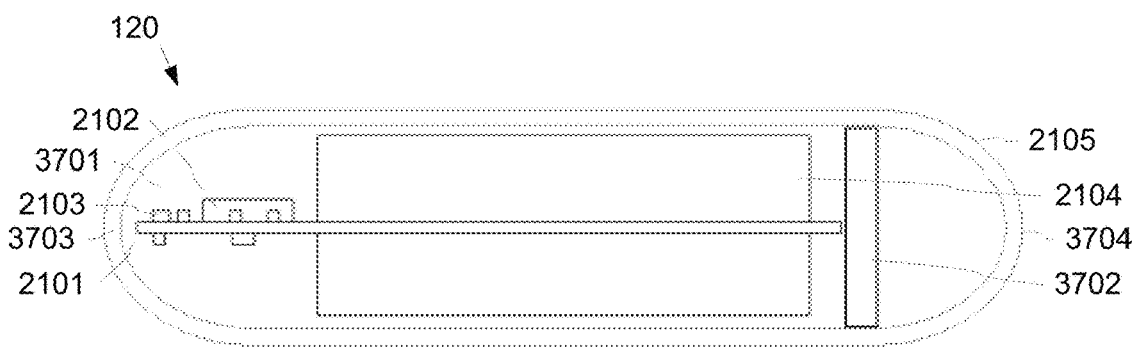

FIG. 37B shows the sensing device 120 from FIG. 37A after the end 3704 is closed or sealed. When the enclosure 2105 is made of glass it can be made to be a hermetical seal of the internal components of the sensing device 120 from the outer environment and prevent liquid of the outer environment from entering inside the sensing device 120. Other materials can also be used to create a seal such as ceramics, polymers, metals and other materials. The method of closing an end of the enclosure 2105 using heat can also be used if the enclosure 2105 is made of high temperature polymers such as COC, COP, PTFE, PEEK, PTFE and other polymers as well as lower temperature polymers such as polypropylene and other polymers as well as if it is made of ceramics or any combination of materials where the closing of the enclosure 2105 requires heat that could damage the internal components of the sensing device 120.

Figure 37C:
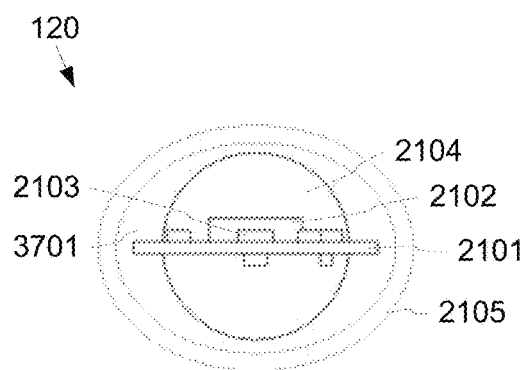

FIG. 37C illustrates the sensing device 120 in FIG. 37B viewed from the 3703 end.

Figure 37D:
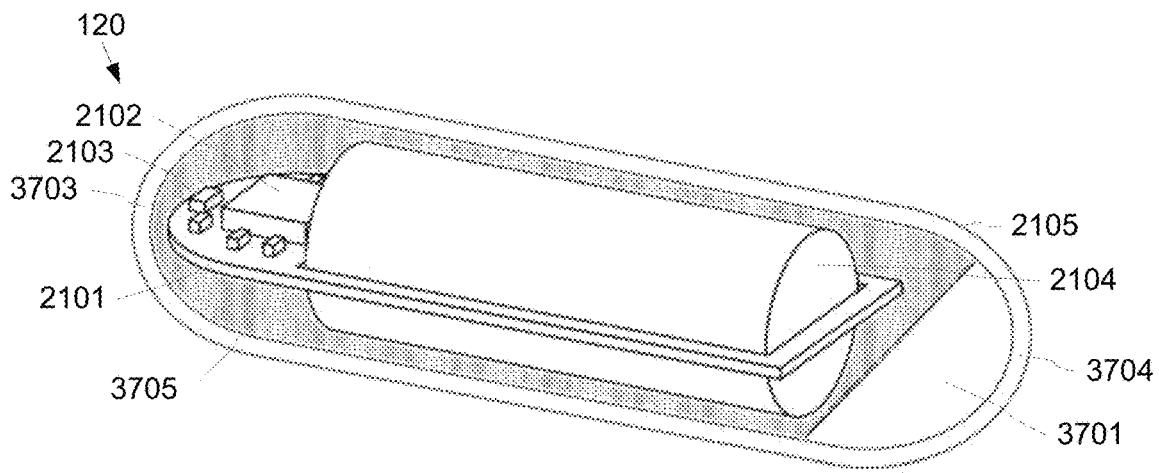

FIG. 37D illustrates another configuration of the sensing device 120 in FIG. 37B where part of the internal cavity 3701 is filled with a polymer material 3705 such as epoxy or silicone or thermally conductive polymer. The use of a polymer to fill the internal cavity can be used to manipulate the center of gravity of the sensing device 120, for example if one portion of the sensing device is filled with polymer then the sensing device would orient itself such that the heavier portion of the sensing device would orient down when possible, this can be used to provide optimal orientation of the sensing device when it comes to antenna orientation and sensor orientation, this can be particularly helpful if the shape of the sensing device does not in itself provide orientation of the sensing device, for example the outer shape of the sensing device could be round. Other materials than polymers or combination of materials can be used to fill or partly fill the cavity of the sensing device 120.

FIG. 38A illustrates an overhead stirring system 3800. The system 3800 consists of a motor 3802 that is connected to a mixing rod 2402 to mix a liquid 115 in a container 110 by rotating rod 2402 and mixing blades 2405. The mixing rod 2402 can contain sensors which readings can be wirelessly transmitted to a receiving antenna 3803 located around or proximal to the rod 2402. The outside 3804 of the container 110 may be heated or cooled such that the temperature of the liquid 115 can be effected. The temperature of the liquid 115 may be measured by a temperature sensor in the rod 2402 and transmitted wirelessly to antenna 3803. An external control system may use the wireless temperature measurements to control the temperature of the liquid 115. The heating or cooling of the container 110 may happen by inserting the container 110 in a temperature controlled water bath or by having heating or cooling elements proximal to the external surface 3804 of the container 110. The stirring system 3800 may be used to dissolve solid compounds.

FIG. 38B shows a cut through view of a mixing rod 2402 with mixing blades 2405 of FIG. 38A. The rod 2402 can contain a circuit board 3810 supporting an integrated circuit 2102 and a temperature sensing element 2103 readable by the integrated circuit 2102. The circuit board 3804 may also contain a gyro sensor 3805 for sensing rotation. The circuit board 3810 may be connected to a pH electrode 3806 and a reference electrode 3807 for measuring pH of the liquid 115. The circuit board may be connected to an antenna 3808 for transmitting sensor data wirelessly as well as for powering the internal electronics in rod 2402. The sensing rod 2402 and mixing blades 2405 may be made from stainless steel or PTFE plastic or other materials or combinations of materials however in order to avoid blocking the wireless signal to and from antenna 3808 then any material 3809 covering antenna 3808 must be a material that does not significantly attenuate the wireless signal such a material could be PTFE or most other types of plastic, glass or ceramics. Any internal cavities in rod 2402 can be filled with a polymer like epoxy or a thermally conductive polymer like Wakefield-Vette PL-BT-603-50M or a combination thereof. The rod 2402 may be configured to measure fewer or more parameters such as any of temperature, pH, sodium, ammonia, lithium, potassium, calcium, dissolved oxygen, $CO_2$, specific gravity, refractive index, viscosity, salinity, conductance, color, absorbance, fluorescence, pressure, electrochemical, conductivity, chemiluminescence, liquid level, rotation, acceleration or velocity The stirring system 3800 may be configured such that the stirring function stops when a certain measured parameter of the liquid 115 is achieved. The stirring system 3800 may be configured such that a user is alerted when a certain measured parameter of the liquid 115 is reached.

Figure 39:
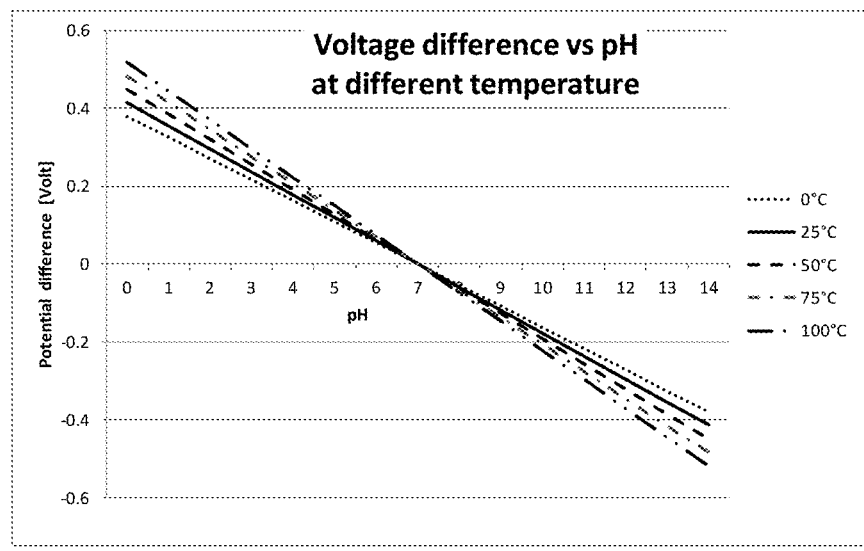
FIG. 39 illustrates the relationship between the voltage difference between a pH electrode and a reference electrode due to pH at different temperatures.

FIG. 39 is a graph that illustrates the relationship between the voltage difference between a pH electrode and a reference electrode due to pH at different temperatures. pH readings are done by measuring the voltage difference between a pH sensor and a reference sensor and then multiplying the number by a factor and add an offset to get a pH reading, where the factor is typically around 0.5916V per pH units and the offset is 7 pH units at 25° C. temperature. The multiplication factor for calculating pH based on a voltage difference can be influenced by temperature by about 0.34% per ° C. at room temperature so the pH reading can be more accurate if compensated for temperature. A pH sensor can drift over time so when accurate measurements are needed then the pH sensor should be calibrated, this can be done by submerging the sensor in one or more solutions of known pH and calculating one or more calibration factors that can be applied to correct the pH calculation. One method for example to correct a pH reading is by doing a piecewice linear correction but other methods can also be used. Calibration factors can be stored in the wireless sensing device and applied to the pH calculation in the wireless sensing device or the calibration factors can be transferred to the wireless receiver where the wireless receiver calculates the pH. If calibration of a pH sensor shows that the multiplication factor for calculating pH based on a voltage difference from the expected factor or if the calibration shows that the offset is different from 7 by a certain amount then the pH sensor or the reference sensor can be assumed to be unusable and the wireless sensing device can be marked as broken by having a certain value stored in the memory of the wireless sensing device or by other means. A pH probe can be used without correcting for temperature when the temperature of the environment and or sample is known or if the error is acceptable or if working close to 7 pH units. By stirring a wireless sensing device with pH measurement then the pH reading can be more responsive since there is rapid fluid exchange at the pH and reference sensor. A pH sensor and reference sensor should be stored in a solution, for example potassium chloride when not used such that the pH sensing surface and the reference surface does not dry out otherwise the sensor can be damaged or it can take an extended time to rehydrate the sensor to get acceptable function.

The wireless sensing device can be designed for communicating with a wireless receiver at a frequency of 13.56 MHz or at another frequency, for example 125 KHz or 135 KHz or 140 KHz or 433 MHz or any frequency in between approximately 10 KHz and 500 MHz, the wireless sensing device can also communicate at higher frequencies above 500 MHz like 860 MHz to 960 MHz or 2.45 GHz or other frequencies above 500 MHz but there may be attenuation from the substance that it is submerged in. The wireless sensing device can also communicate at frequencies lower than 10 KHz but it may require larger antennas. The wireless sensing device can be designed to receive communication at a first frequency and to send communication at a second frequency. The wireless sensing device can be designed to be powered with wireless energy at a first frequency and receive communication at a second frequency and to send communication at a third frequency where one or more of the first and second and third frequency may be the same or different frequencies. The wireless frequency that powers a wireless sensing device can be any of the same frequencies that are used for communication. The wireless signal protocol that is used to communicate and power a wireless sensing device can be RFID. The wireless signal protocol that is used to communicate and power a wireless sensing device can be any of the RFID protocols like ISO 15693 or ISO 14443 or Mifare or any of the ISO 18000 standards and ISO 18000 sub standards like part 1, 2, 3, 4, 5, 6, 7, 61, 62, 63 or 64 or any other standard or non-standard RFID protocols.

A submersible device can mean a sensing device or a wireless sensing device.

Each of the individual variations or embodiments described and illustrated herein can have discrete components and features which may be readily separated from or combined with the features of any of the other variations or embodiments. Modifications may be made to adapt a particular situation, material, composition of matter, process, process act(s) or step(s) to the objective(s), spirit or scope of the disclosure.

Methods recited herein may be carried out in any order of the recited events that is logically possible, as well as the recited order of events. Moreover, additional steps or operations may be provided, or steps or operations may be eliminated to achieve the desired result.

Furthermore, where a range of values is provided, every intervening value between the upper and lower limit of that range and any other stated or intervening value in that stated range is encompassed within the disclosure. Any optional feature of the variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present disclosure (in which case what is present herein shall prevail). The referenced items are provided solely for their disclosure prior to the filing date of the present application. Nothing herein is to be construed as an admission that the present disclosure is not entitled to antedate such material by virtue of prior disclosure.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of elements, or use of a "negative" limitation. Unless defined otherwise, all technical and scientific terms used herein have the same meaning as commonly understood by one of ordinary skill in the art to which this invention belongs.

U.S. patent application Ser. No. 15/882,909, filed Jan. 29, 2018, International Application No. PCT/US2017/042435, filed Jul. 17, 2017, and U.S. Provisional Application No. 62/362,737, filed Jul. 15, 2016, are incorporated by reference herein in their entireties.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure.

We claim:

1. A method for determining pH of a first liquid in a container and agitating the same first liquid, comprising:
    positioning the container on a receiver instrument, wherein the receiver instrument comprises a wireless receiver;
    positioning a submersible device in the first liquid, wherein the submersible device comprises a pH sensor and a reference sensor and a temperature sensor and a wireless transmitter, and wherein the wireless transmitter is in communication with the wireless receiver,
    measuring pH of the first liquid by determining a voltage potential difference between the pH sensor and the reference sensor;
    measuring a temperature of the first liquid with the temperature sensor;
    communicating data to the receiver instrument;
    agitating the first liquid, wherein the submersible device comprises a first magnet, and wherein the receiver instrument comprises a magnetic field creator, and wherein the magnetic field creator creates and alters a magnetic field exerting a magnetic force on the first magnet, and wherein the agitating the first liquid comprises moving the submersible device in the first liquid with the magnetic force on the first magnet.

2. The method of claim 1, wherein the magnetic field creator comprises a permanent magnet and a motor, wherein the motor is mechanically attached to the permanent magnet, further comprising rotating the permanent magnet with the motor.

3. The method of claim 1, wherein the magnetic field creator comprises one or more electromagnets.

4. The method of claim 1, further comprising:
    setting a target pH of the first liquid with one or more controls on the receiving instrument;
    where the receiver instrument controls an introduction of a second liquid into the first liquid until a specified pH level of the first liquid is reached by a pump;
    displaying to a user an amount of second liquid pumped into the first liquid.

5. The method of claim 1 where the submersible device is powered by wireless energy and where the submersible device does not contain a battery.

6. The method of claim 1, wherein the submersible device communicates with the receiver instrument using RFID communication and where the RFID communication powers the submersible device.

7. The method of claim 1, wherein the submersible device communicates with the receiver instrument using 13.56 MHz frequency.

8. The method of claim 1 where the pH is calculated based on the voltage potential difference between the pH sensor and the reference sensor and where the pH calculation is compensated based on the first liquid temperature from the temperature sensor, where the calculation of the pH is performed in the receiver instrument.

9. The method of claim 1 where the pH is calculated based on the voltage potential difference between the pH sensor and the reference sensor and where the pH calculation is compensated based on the first liquid temperature from the temperature sensor, where the calculation of the pH is performed in the submersible device.

10. The method of claim 1 where the submersible device comprises the pH sensor, the reference sensor, the temperature sensor, a magnet, and a circuit board and where the circuit board comprises an antenna embedded in the circuit board and where the circuit board has at least one integrated circuit for measuring the voltage potential difference between the pH sensor and the reference sensor and where the same or an additional integrated circuit can measure the temperature sensor and where the same or an additional integrated circuit has the wireless transmitter.

11. The method of claim 1 where the submersible device comprises a hollow magnet.

12. The method of claim 1 where the pH sensor comprises a glass electrode that is sensitive to hydrogen ions.

13. The method of claim 1 where the reference sensor comprises one of the following:
    a porous frit with a potassium chloride gel electrolyte and a gel electrolyte containing silver and silver chloride in contact with a silver electrode;
    a porous frit with a potassium chloride and silver and silver chloride electrolyte in contact with the porous frit and silver electrode;
    a potassium chloride hard gel electrolyte in contact with a silver and silver chloride electrolyte which is in contact with a silver electrode;
    a porous frit in contact with an electrolyte which is in contact with an electrode;
    a porous frit in contact with a first electrolyte which is in contact with a second electrolyte which is in contact with an electrode;
    a PTFE membrane in contact with an electrolyte which is in contact with an electrode;
    a PTFE membrane in contact with a first electrolyte which is in contact with a second electrolyte which is in contact with an electrode.

14. The method of claim 1 where the submersible device can be completely immersed into the first liquid, and wherein the submersible device does not require any wires to function; and wherein said submersible device measures at least one liquid characteristic, said at least one liquid characteristic being any of temperature, pH, sodium, ammonia, lithium, potassium, calcium, dissolved oxygen, $CO_2$, specific gravity, refractive index, viscosity, salinity, conductance, color, absorbance, fluorescence, pressure, electrochemical, conductivity, chemiluminescence, liquid level, rotation, acceleration or velocity.

15. The method of claim 1 where the receiver instrument can also heat the first liquid.

16. A method for determining pH of a first liquid in a container, comprising:
    positioning the container at a receiver instrument, wherein the receiver instrument comprises a wireless receiver;
    positioning a submersible device in the first liquid, wherein the submersible device comprises a pH sensor and a reference sensor and a temperature sensor and a wireless transmitter, and wherein the wireless transmitter is in communication with the wireless receiver;
    measuring pH of the first liquid by determining a voltage potential difference between the pH sensor and the reference sensor, where the pH sensor comprises a glass electrode that is sensitive to hydrogen ions and where the reference sensor comprises a porous frit with gel electrolyte and an electrode;

measuring a temperature of the first liquid with the temperature sensor;

communicating data to the receiver instrument;

powering the submersible device with wireless energy such that the submersible device does not contain a battery;

calculating the pH based on the voltage potential difference between the pH sensor and the reference sensor and compensating the pH calculation based on the first liquid temperature from the temperature sensor.

17. The method of claim 16 where the first liquid is agitated by the submersible device and wherein the submersible device comprises a first magnet, and wherein the receiver instrument comprises a magnetic field creator, and wherein the magnetic field creator creates and alters a magnetic field exerting a magnetic force on the first magnet, and wherein the agitating the first liquid comprises moving the submersible device in the first liquid with the magnetic force on the first magnet.

18. The method of claim 16, wherein the submersible device communicates with the receiver using RFID communication at 13.56 MHz frequency and where the RFID communication powers the submersible device.

* * * * *